US009145372B2

(12) United States Patent
Lowe, III

(10) Patent No.: US 9,145,372 B2
(45) Date of Patent: Sep. 29, 2015

(54) PYRIDAZINE DERIVATIVES, COMPOSITIONS AND METHODS FOR TREATING COGNITIVE IMPAIRMENT

(75) Inventor: John A. Lowe, III, Stonington, CT (US)

(73) Assignee: AGENEBIO, INC., Baltimore, MD (US)

( * ) Notice: Subject to any disclaimer, the term of this patent is extended or adjusted under 35 U.S.C. 154(b) by 0 days.

(21) Appl. No.: 13/885,569

(22) PCT Filed: Nov. 15, 2011

(86) PCT No.: PCT/US2011/060854
§ 371 (c)(1),
(2), (4) Date: May 15, 2013

(87) PCT Pub. No.: WO2012/068161
PCT Pub. Date: May 24, 2012

(65) Prior Publication Data
US 2013/0237545 A1    Sep. 12, 2013

Related U.S. Application Data

(60) Provisional application No. 61/413,971, filed on Nov. 15, 2010.

(51) Int. Cl.
C07D 403/00 (2006.01)
C07D 405/00 (2006.01)
C07D 409/00 (2006.01)
C07D 401/00 (2006.01)
C07D 251/00 (2006.01)
A61K 31/50 (2006.01)
C07D 237/24 (2006.01)
C07D 413/04 (2006.01)
C07D 401/04 (2006.01)
C07D 403/04 (2006.01)
C07D 413/14 (2006.01)

(52) U.S. Cl.
CPC .............. *C07D 237/24* (2013.01); *A61K 31/50* (2013.01); *C07D 401/04* (2013.01); *C07D 403/04* (2013.01); *C07D 413/04* (2013.01); *C07D 413/14* (2013.01)

(58) Field of Classification Search
USPC .................................. 544/238, 241; 514/247
See application file for complete search history.

(56) References Cited

U.S. PATENT DOCUMENTS

| 5,387,585 | A | 2/1995 | Borer et al. |
| 6,689,816 | B2 | 2/2004 | Fogel |
| 6,743,789 | B2 | 6/2004 | Masciadri et al. |
| 7,381,725 | B2 | 6/2008 | Fletcher et al. |
| 7,498,361 | B2 | 3/2009 | Fogel |
| 7,642,267 | B2 | 1/2010 | Li et al. |
| 8,510,055 | B2 | 8/2013 | Gallagher et al. |
| 2003/0125333 | A1 | 7/2003 | Bryant et al. |
| 2006/0079507 | A1 | 4/2006 | Knust et al. |
| 2006/0167032 | A1 | 7/2006 | Galer et al. |
| 2006/0235021 | A1 | 10/2006 | Blackaby |
| 2007/0112017 | A1 | 5/2007 | Barlow et al. |
| 2009/0143385 | A1 | 6/2009 | Buettelmann et al. |
| 2010/0075954 | A1 | 3/2010 | Knust et al. |
| 2010/0081723 | A1 | 4/2010 | Jonas et al. |
| 2012/0035139 | A9 | 2/2012 | Xu et al. |
| 2013/0237530 | A1 | 9/2013 | Lowe |
| 2014/0057903 | A1 | 2/2014 | Gallagher et al. |

FOREIGN PATENT DOCUMENTS

| GB | 2352630 | | 2/2001 |
| GB | 2352631 | | 2/2001 |
| GB | 2352632 | | 2/2001 |
| WO | WO9925353 | | 5/1999 |
| WO | WO0027849 | | 5/2000 |
| WO | WO0162726 | | 8/2001 |
| WO | WO0240487 | | 5/2002 |
| WO | WO02269948 | | 9/2002 |
| WO | WO03025122 | | 3/2003 |
| WO | WO 2004014865 | A1 * | 2/2004 |
| WO | WO2004048551 | | 6/2004 |
| WO | WO2007018660 | | 2/2007 |
| WO | WO2007019312 | | 2/2007 |
| WO | WO 2010036553 | A1 * | 4/2010 |
| WO | WO2012068161 | | 5/2012 |

OTHER PUBLICATIONS

Van Niel, M.B., et al., J. Med. Chem. vol. 48, 6004-6011. Published 2005.*
Achermann et al., "Discovery of the imidazo[1,5-α][1,2,4]-triazolo[1,5-d][1,4] benzodiazepine scaffold as a novel, potent and selective GABAA α5 inverse agonist series," Aug. 2009, Bioorganic & Medicinal Chemistry Letters, vol. 19, pp. 5746-5752.
Adams et al., "Hippocampal dependent learning ability correlates with N-methyl-D-aspartate (NMDA) receptor levels in CA3 neurons of young and aged rats," J. Comp. Neurol., 432:230-243 (2001).
Akbarian et al., "Gene Expression for Glutamic Acid Decarboxylase Is Reduced Without Loss of Neurons in Prefrontal Cortex of Schizophrenics," Arch. Gen. Psychiatry 52:258-266, 1995.
Albert, "The ageing brain: normal and abnormal memory," Philos. Trans. R. Soc. Lond. B. Biol. Sci., 352:1703-1709 (1997).

(Continued)

*Primary Examiner* — Paul Zarek
*Assistant Examiner* — George W Kosturko
(74) *Attorney, Agent, or Firm* — Ropes & Gray LLP; Karen Mangasarian; Yang Xu

(57) ABSTRACT

This invention relates to pyridazine derivatives, compositions comprising therapeutically effective amounts of those pyridazine derivatives and methods of using those derivatives or compositions in treating central nervous system (CNS) disorders with cognitive impairment that are responsive to agonists of α5 subunit containing GABA$_A$ receptor, e.g., age-related cognitive impairment, Mild Cognitive Impairment (MCI), dementia, Alzheimer's Disease (AD), prodromal AD, post traumatic stress disorder (PTSD), schizophrenia and cancer-therapy-related cognitive impairment.

61 Claims, 15 Drawing Sheets

(56) References Cited

OTHER PUBLICATIONS

Figure 1A:
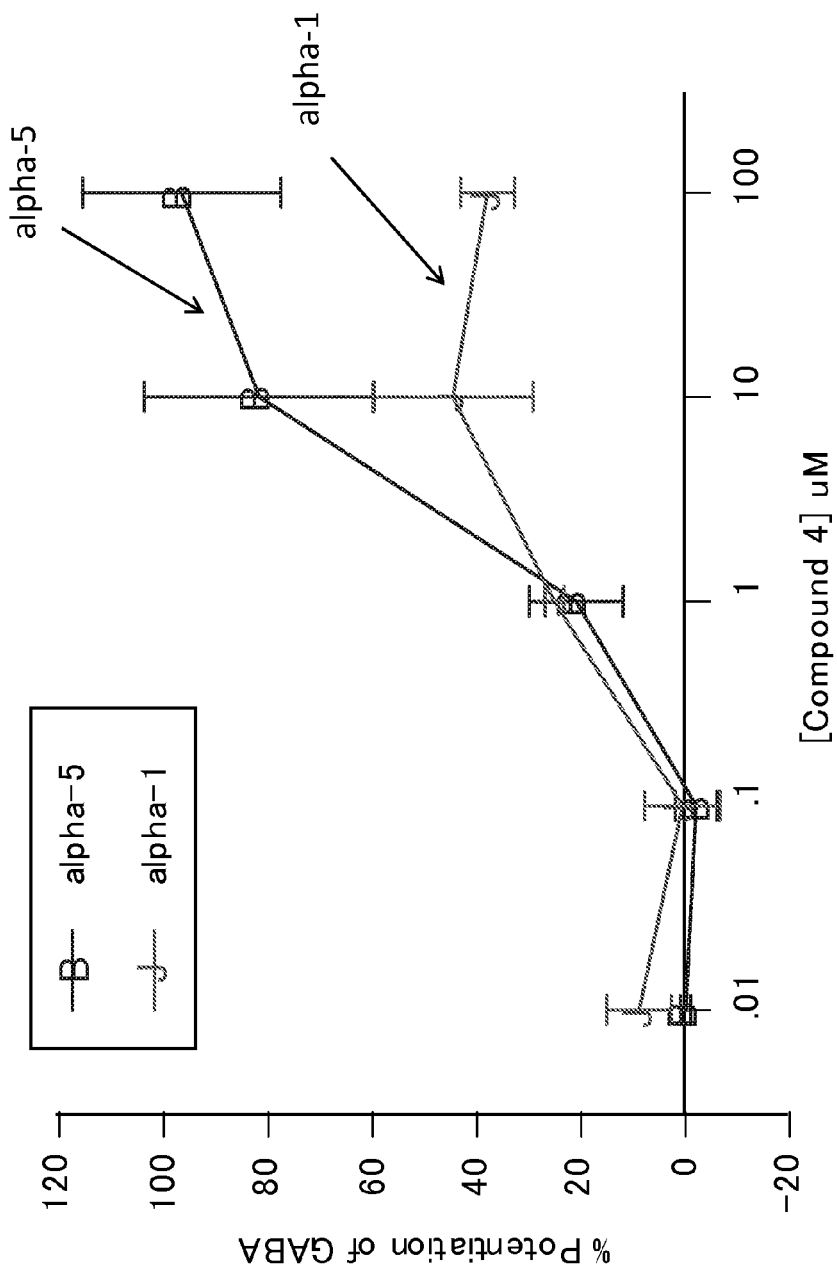

Ashe et al., "Probing the biology of Alzheimer's disease in mice", Neuron., 2010, 66(5): 631-645.
Bakker et al (2008) Pattern separation in the human hippocampal CA3 and dentate gyrus. Science 319: 1640-1642.
Ballard et al., "RO4938581, a novel cognitive enhancer acting at GABAA α5 subunit-containing receptors", Psychopharmacology, 2009, 202: 207-223.
Barnes et al., "Region-specific age effects on AMPA sensitivity: electrophysiological evidence for loss of synaptic contacts in hippocampal field CA1," Hippocampus, 2:457-468 (1992).
Bartus et al., "The cholinergic hypothesis of geriatric memory dysfunction," Science, 17:408-414 (1982).
Bassett et al., "Familial risk for Alzheimer's disease alters fMRI activation patterns", Brain., 2006, 129(5): 1229-1239.
Baxter et al., "Neurobiological substrates of behavioral decline: models and data analytic strategies for individual differences in aging," Neurobiol. Aging, 17:491-495 (1996).
Berezhnoy et al., "Pharmacological Properties of DOV 315,090, an ocinaplon metabolite", BMC Pharmacology, 2008, 8:11: 1-10.
Berntsen, "The Unbidden Past: Involuntary Autobiographical Memories as a Basic Mode of Remembering," Current Directions in Psychological Science 19(3) 138-142, 2010.
Berton et al., "Acamprosate Enhances N-Methyl-D-Apartate Receptor-Mediated Neurotransmission But Inhibits Presynaptic GABAB Receptors in Nucleus Accumbens Neurons," Alcohol Clin Exp Res, Feb. 1998, 22(1): 183-191.
Blalock et al., Gene Microarrays in Hippocampal Aging: Statistical Profiling Identifies Novel Processes Correlated with Cognitive Impairment, J. Neurosci., 2003, 23(9): 3807-3819.
Bookheimer et al., "Patterns of Brain Activation in People at Risk for Alzheimer's Disease", N Engl J Med., 2000, 343(7): 450-456.
Brewer et al., "Optimized survival of hippocampal neurons in B27-supplemented Neurobasal, a new serum-free medium combination," J. Neuroscience Res. 35:567-576 (1993).
Busche et al., "Clusters of Hyperactive Neurons Near Amyloid Plaques in a Mouse Model of Alzheimer's Disease", Science, 2008, 321: 1686-1689.
Carling et al., "7-(1,1-Dimethylethyl)-6-(2-ethyl-2H-1,2,4- triazol-3-ylmethoxy)-3-(2-fluorophenyl)-1,2,4-triazolo[4,3-b]pyridazine: A Functionally Selective γ-Aminobutyric AcidA (GABAA) α2/α3-Subtype Selective Agonist That Exhibits Potent Anxiolytic Activity but Is Not Sedating in Animal Models", Journal of Medicinal Chemistry, 2005, 48(23): 7089-7092.
Celone et al., "Alterations in Memory Networks in Mild Cognitive Impairment and Alzheimer's Disease: An Independent Component Analysis", J. Neurosci., 2006, 26(40): 10222-10231.
Chambers "An Orally Bioavailable, Functionally Selective Inverse Agonist at the Benzodiazepine Site of GABAA r5 Receptors with Cognition Enhancing Properties," J. Med. Chem., 47:5829-5832 (2004).
Chambers et al., "Identification of a novel, selective GABA(A) alpha5 receptor inverse agonist which enhances cognition," J. Med. Chem., 46:2227-2240 (2003).
Chappell et al., "A re-examination of the role of basal forebrain cholinergic neurons in spatial working memory," Neuropharmacology, 37: 481-488, (1998).
Colombo et al., "Spatial memory is related to hippocampal subcellular concentrations of calcium-dependent protein kinase C isoforms in young and aged rats," Proc. Natl. Acad. Sci. USA, 94:14195-14199 (1997).
De Hoz et al., "Spatial learning with unilateral and bilateral hippocampal networks", European Journal of Neuroscience, 2005, 22: 745-754.
Dickerson BC et al. (2004) Medial temporal lobe function and structure in mild cognitive impairment. Ann Neurol. 56:27-35.
Dickerson et al., "Increased hippocampal activation in mild cognitive impairment compared to normal aging and AD", Neurology, 2005, 65: 404-411.
Dietrich et al., "Clinical Patterns and Biological Correlates of Cognitive Dysfunction Associated with Cancer Therapy," The Oncologist 2008;13:1285-1295.
Ellison et al., "Beyond the "C" in MCI: Noncognitive Symptoms in Amnestic and Non-amnestic Mild Cognitive Impairment," CNS Spectr. 13:66-72, 2008.
Folstein et al., ""Mini-mental state". A practical method for grading the cognitive state of patients for the clinician," J Psychiatric Res., 12:189-198 (1975).
Gallagher et al., "Relationship of age-related decline across several behavioral domains," Neurobiol. Aging, 10:691-708 (1989).
Gallagher et al., "Severity of spatial learning impairment in aging: development of a learning index for performance in the Morris water maze," Behav. Neurosci., 107 (4):618-626 (1993).
Gallagher, "Animal models of memory impairment," Philos. Trans. R. Soc. Lond. B. Biol.Sci., 352:1711-1717 (1997).
Giusti et al., "Imidazenil: A New Partial Positive Allosteric Modulator of γ-Aminobutyric Acid (GABA) Action at GABAA Receptors1", The Journal of Pharmacology and Experimental Therapeutics, 1993, 266(2): 1018-1028.
Goldin et al., "Maintenance of Xenopus laevis and Oocyte Injection", Methods in Enzymology, 1992, 207: 266-279.
Goodacre et al., "Imidazo[1,2-a]pyrimidines as Functionally Selective and Orally Bioavailable GABAAα2/α3 Binding Site Agonists for the Treatment of Anxiety Disorders", J. Med. Chem., 2006, 49: 35-38.
Guidotti et al., "GABAergic dysfunction in schizophrenia: new treatment strategieson the horizon," Psychopharmacology (2005) 180: 191-205.
Haberman et al., "Rapid encoding of new information alters the profile of plasticity-related mRNA transcripts in the hippocampal CA3 region", PNAS, 2008, 105(30): 10601-10606.
HARVEYet al., "Stress—restress evokes sustained iNOS activity and altered GABA levels and NMDA receptors in rat hippocampus", Psychopharmacology, 2004, 175: 494-502.
Hashimoto et al., "Alterations in GABA-related transcriptome in the dorsolateral prefrontal cortex of subjects with schizophrenia", Molecular Psychiatry, 2008, 13: 147-161.
Hashimoto et al., "Gene Expression Deficits in a Subclass of GABA Neurons in the Prefrontal Cortex of Subjects with Schizophrenia", J. Neurosci, 2003, 23(15): 6315-6326.
Helm et al., "GABAB receptor antagonist SGS742 improves spatial memory and reduces protein binding to the cAMP response element (CRE) in the hippocampus", Neuropharmacology, 2005, 48: 956-964.
HILLet al., "First Occurrence of Hippocampal Spatial Firing in a New Environment", Experimental Neurology, 1978, 62: 282-297.
Hughes et al., "Physiochemical drug properties associated with in vivo toxicological outcomes", Bioorganic & Medicinal Chemistry Letters, 2008, 18: 4872-4875.
International Union of Pure and Applied Chemistry—Organic Chemistry Division—Commission on Nomenclature of Organic Chemistry, "Rules for the Nomenclature of Organic Chemistry—Section E: Stereochemistry", Pure & Appl. Chem., 1976, 45: 11-30.
Jarrard, "On the role of the hippocampus in learning and memory in the rat," Behav. Neural. Biol. 60(1):9-26 (1993).
Kamenetz et al. (2003) APP processing and synaptic function. Neuron 37: 925-37.
Khan et al., "Topiramate attenuates exaggerated acoustic startle in an animal model of PTSD", Psychopharmacology, 2004, 172: 225-229.
Kim et al. "Transient Impairment of Hippocampus-dependent Learning and Memory in Relatively Low-Dose of Acute Radiation Syndrome is Associated with Inhibition of Hippocampal Neurogenesis," J. Radiat. Res., 49, 517-526 (2008).
Kluger et al., "Neuropsychological prediction of decline to dementia in nondemented elderly," J Geriatr Psychiatry Neurol., 12:168-179 (1999).
Kobayashi et al., "Behavioral phenotypes of amyloid-based genetically modified mouse models of Alzheimer's disease", Genes, Brain and Behavior, 2005, 4: 173-196.
Koh et al., "Treatment with selective GABAA α5 receptor agonists improves cognitive function in aged rats with memory impairment," Society for Neuroscience meeting, Nov. 16, 2010, Handout, 1 page.

(56) References Cited

OTHER PUBLICATIONS

Lein et al., "Defining a molecular atlas of the hippocampus using DNA microarrays and high-throughput in situ hybridization," J Neurosci., 24:3879-3889 (2004).
Leutgeb et al., "Independent Codes for Spatial and Episodic Memory in Hippocampal Neuronal Ensembles", Science, 2005, 309: 619-623.
Leutgeb. et al., "Pattern Separation in the Dentate Gyrus and CA3 of the Hippocampus", Science, 2007, 315: 961-966.
Liberzon et al., "Stress-Restress: Effects on ACTH and Fast Feedback", Psychoneuroendocrinology, 1997, 22(6): 443-453.
Lingford-Hughes et al., "Imaging the GABA-Benzodiazepine Receptor Subtype Containing the α5-Subunit In Vivo With [11C]Ro15 4513 Positron Emission Tomography", J. Cereb. Blood Flow Metab, 2002, 22(7): 878-889.
Lippa et al., "Selective anxiolysis produced by ocinaplon, a GABAA receptor modulator," PNAS 102(20):7380-7385, 2005.
Liu et al., "Synthesis and Pharmacological Properties of Novel 8-Substituted Imidazobenzodiazepines: High-Affinity, Selective Probes for α5-Containing GABAA Receptors1", J. Med. Chem., 1996, 39: 1928-1934.
Lodge et al., "A Loss of Parvalbumin-Containing Interneurons Is Associated with Diminished Oscillatory Activity in an Animal Model of Schizophrenia," J. Neurosci., 29:2344-2354, 2009.
Lupien et al., "Effects of stress throughout the lifespan on the brain, behaviour and cognition," Reviews, Jun. 2009, vol. 10, 434-445.
Maeda et al., "Visualization of α5 Subunit of GABAA/Benzodiazepine Receptor by [11C]Ro15-4513 Using Positron Emission Tomography", Synapse, 2003, 47: 200-208.
Meguro, "Subjective Memory Complaints are not Sine Qua Non as Diagnostic Criteria for MCI: the Tajiri Project", Acta Neurologica Taiwanica, 2006, 15(1): 55-57.
Miller et al (2008) Hippocampal activation in adults with mild cognitive impairment predicts subsequent cognitive decline. J. Neurol Neurosurg Psychiatry 79: 630-635.
Mirza et al., "NS11394 [3'-[5-(1-hydroxy-l-methyl-ethyl)-benzoimidazol-1-yl]-biphenyl-2-carbonitr ile], a unique subtype-selective GABAA receptor positive allosteric modulator: in vitro actions, pharmacokinetic properties and in vivo anxiolytic efficacy." J Pharmacol Exp Ther 327(3): 954-68, 2008.
Mondadori et al., "Enhanced brain activity may precede the diagnosis of Alzheimer's disease by 30 years," Brain. 129:2908-22, 2006.
Morris, Learning and Motivation 12:239-260 (1981) "Spatial Localization Does Not Require the Presence of Local Cues"
Nicolle et al., "In Vitro Autoradiography of Ionotropic Glutamate Receptors in Hippocampus and Striatum of Aged Long—Evans Rats: Relationship to Spatial Learning", Neuroscience, 1996, 74(3): 741-756.
Nicolle et al.,"Metabotropic Glutamate Receptor-Mediated Hippocampal Phosphoinositide Turnover Is Blunted in Spatial Learning-Impaired Aged Rats," J. Neurosci. 19:9604-9610, (1999).
Oler et al., "Age-Related Deficits in the Ability to Encode Contextual Change: A Place Cell Analysis", Hippocampus, 2000, 10: 338-350.
Palop et al., "Aberrant excitatory neuronal activity and compensatory remodeling of inhibitory hippocampal circuits in mouse models of Alzheimer's disease," Neuron 55: 697-711 (2007).
Petersen et al., "Mild cognitive impairment: clinical characterization and outcome," Arch. Neurol., 56: 303-308 (1999).
Petersen, "Mild Cognitive Impairment: Current Research and Clinical Implications", Seminars in Neurology, 2007, 27(1): 22-31.
Peterson et al., "Mild Cognitive Impairment: An Overview," CNS Spectr. 13:45-53, 2008.
Platt et al., "Contribution of alpha 1GABAA and alpha 5GABAA receptor subtypes to the discriminative stimulus effects of ethanol in squirrel monkeys," J. Pharmacol. Exp. Ther., 313:658-667 (2005).
Pym et al., "Selective labelling of diazepam-insensitive GABAA receptors in vivo using [3H]Ro 15-4513", British Journal of Pharmacology, 2005, 146: 817-825.
Qin et al., Evaluation of methods for oligonucleotide array data via quantitative real-time PCR. BMC Bioinformatics, 7:23 (2006).

Rapp et al., "Preserved neuron number in the hippocampus of aged rats with spatial learning deficits," Proc. Natl. Acad. Sci. 93:9926-9930, (1996).
Rapp et al., "An Evaluation of Spatial Information Processing in Aged Rats", Behavioral Neuroscience, 1987, 101(1): 3-12.
Rapp et al., "Memory systems in normal and pathological aging," Curr. Opin. Neurol., 7:294-298 (1994).
Reilly et al., "Effects of Acamprosate on Neuronal Receptors and Ion Channels Expressed in Xenopus Oocytes," Alcohol Clin Exp Res, Feb. 2008, 32(2): 188-196.
Robbins et al., "Cambridge Neuropsychological Test Automated Battery (CANTAB): a factor analytic study of a large sample of normal elderly volunteers," Dementia, 5:266-281 (1994).
Sankaranarayanan, "Genetically modified mice models for Alzheimer's disease," Curr Top Med Chem. 2006;6(6):609-27.
Small et al., "Imaging correlates of brain function in monkeys and rats isolates a hippocampal subregion differentially vulnerable to aging," Proc. Natl. Acad. Sci. USA., 101:7181-7186 (2004).
Smith et al., "Circuit-specific alterations in hippocampal synaptophysin immunoreactivity predict spatial learning impairment in aged rats," J. Neurosci., 20:6587-6593 (2000)
Soussain et al., "CNS complications of radiotherapy and chemotherapy," Lancet 2009; 374: 1639-51.
Steele et al., "Delay-Dependent Impairment of a Matching-to-Place Task With Chronic and Intrahippocampal Infusion of the NMDA-Antagonist D-AP5", Hippocampus, 1999, 9: 118-136.
Sternfeld, et al., "Selective, orally active gamma-aminobutyric acidA alpha5 receptor inverse agonists as cognitition enhancers,", J. Med. Chem., 47:2176-2179 (2004).
Sur et al., "Rat and Human Hippocampal α5 Subunit-Containing γ-Aminobutyric AcidA Receptors Have α5β3γ2 Pharmacological Characteristics", Molecular Pharmacology, 1998, 54: 928-933.
Szekeres et al., "3,4-Dihydronaphthalen-1(2H)-ones: novel ligands for the benzodiazepine site of alpha5-containing GABAA receptors," Bioorg. Med. Chem. Lett., 14:2871-2875 (2004).
Tanila et al., "Discordance of Spatial Representation in Ensembles of Hippocampal Place Cells", Hippocampus, 1997, 7: 613-623.
Thomaes et al., "Increased activation of the left hippocampus region in Complex PTSD during encoding and recognition of emotional words: A pilot study," Psychiatry Research: Neuroimaging 171 (2009) 44-53.
Tremolizzo et al., "An epigenetic mouse model for molecular and behavioral neuropathologies related to schizophrenia vulnerability", PNAS, 2002, 99(26): 17095-17100.
Van Niel et al., "A New Pyridazine Series of GABAA α5 Ligands", J. Med. Chem., 2005, 48: 6004-6011.
Vinkers et al," the inhibitory GABA system as a therapeutic target for cognitive symptoms in Schizophrenia: investigational agents in the pipeline," Expert Opin. Investig. Drugs (2010) 19(10):1217-1233.
Volk et al., "Decreased Glutamic Acid Decarboxylase67 Messenger RNA Expression in a Subset of Prefrontal Cortical γ-Aminobutyric Acid Neurons in Subjects With Schizophrenia", Arch Gen Psychiatry, 2000, 57: 237-245.
Walsh et al., "Ionic currents in cultured rat suprachiasmatic neurons," Neuroscience, 69:915-929 (1995).
Wang et al., "Magnetic Resonance Imaging of Hippocampal Subfields in Posttraumatic Stress Disorder," Arch. Gen. Psychiatry 67:296-303, 2010.
Whitehouse et al., "Alzheimer's disease and senile dementia: loss of neurons in the basal forebrain," Science, 215:1237-39 (1982).
Wilson et al. (2005) Age associated alterations of hippocampal place cells are subregion specific. J. Neuroscience 25(29): 6877-6886.
Wilson et al., "Cognitive Aging and the Hippocampus: How Old Rats Represent New Environments", J. Neurosci., 2004, 24(15): 3870-3878.
Wilson et al., "Place cell rigidity correlates with impaired spatial learning in aged rats", Neurobiology of Aging, 2003, 24: 297-305.
Winblad et al., "Mild cognitive impairment—beyond controversies, towards a consensus: report of the International Working Group on Mild Cognitive Impairment", Journal of Internal Medicine, 2004, 240-246.

(56) References Cited

OTHER PUBLICATIONS

Wisden et al., "The Distribution of 13 GABAA Receptor Subunit mRNAs in the Rat Brain. I. Telencephalon, Diencephalon, Mesencephalon," The Journal of Neuroscience, Mar. 1992, 12(3): 1040-1062.

Wishart et al., "Increased Brain Activation During Working Memory in Cognitively Intact Adults With the APOE ∈4 Allele", Am J Psychiatry, 2006, 163: 1603-1610.

Wood et al., "Hippocampal pathology in individuals at ultra-high risk for psychosis: A multi-modal magnetic resonance study," NeuroImage 52:62-63, 2010.

Woon et al., "Hippocampal volume deficits associated with exposure to psychological trauma and posttraumatic stress disorder in adults: A meta-analysis," Progress in Neuro-Psychopharmacology & Biological Psychiatry 34 (2010) 1181-1188.

Wu et al., "A Model Based Background Adjustment for Oligonucleotide Expression Arrays," Journal of American Statistical Association, 99:909-917 (2004).

Yaffe et al., "Posttraumatice Stress Disorder and Risk of Dementia Among US Veterans," Arch. Gen. Psychiatry, 67(6):608-613, 2010.

Yang et al., "Cyclophosphamide impairs hippocampus-dependent learning and memory in adult mice: Possible involvement of hippocampal neurogenesis in chemotherapy-induced memory deficits," Neurobiology of Learning and Memory 93 (2010) 487-494.

Yehuda et al., "Longitudinal Assessment of Cognitive Performance in Holocaust Survivors with and without PTSD", Biol Psychiatry, 2006, 60: 714-721.

Yoon et al., "GABA Concentration Is Reduced in Visual Cortex in Schizophrenia and Correlates with Orientation-Specific Surround Suppression", J. Neurosci., 2010, 30(10): 3777-3781.

Young et al., "Using the Matrics to guide development of a preclinical cognitive test battery for research in schizophrenia", Pharmacol Ther., 2009, 122(2): 150-202.

Zierhut et al., "The role of hippocampus dysfunction in deficient memory encoding and positive symptoms in schizophrenia," Psychiatry Research: Neuroimaging 183 (2010) 187-194.

Zoran et al., "Specific muscle contacts induce increased transmitter release and neuritic arborization in motoneuronal cultures," Dev Biol., 179:212-22 (1996).

\* cited by examiner

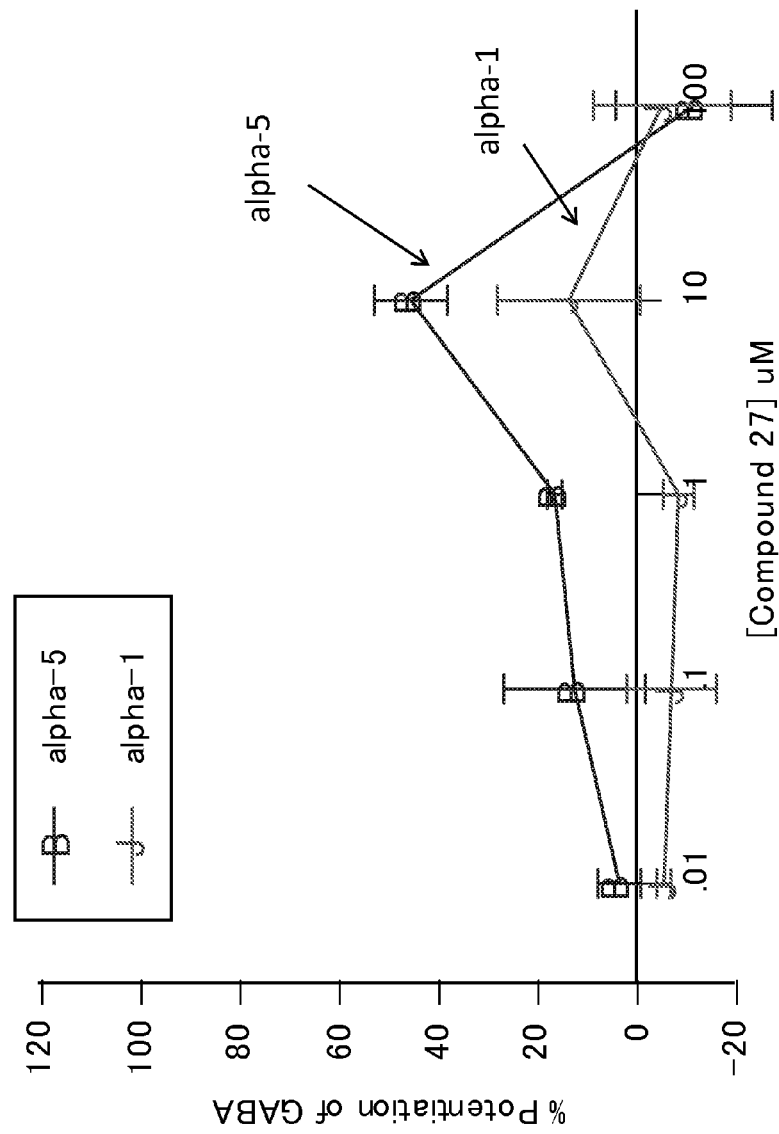

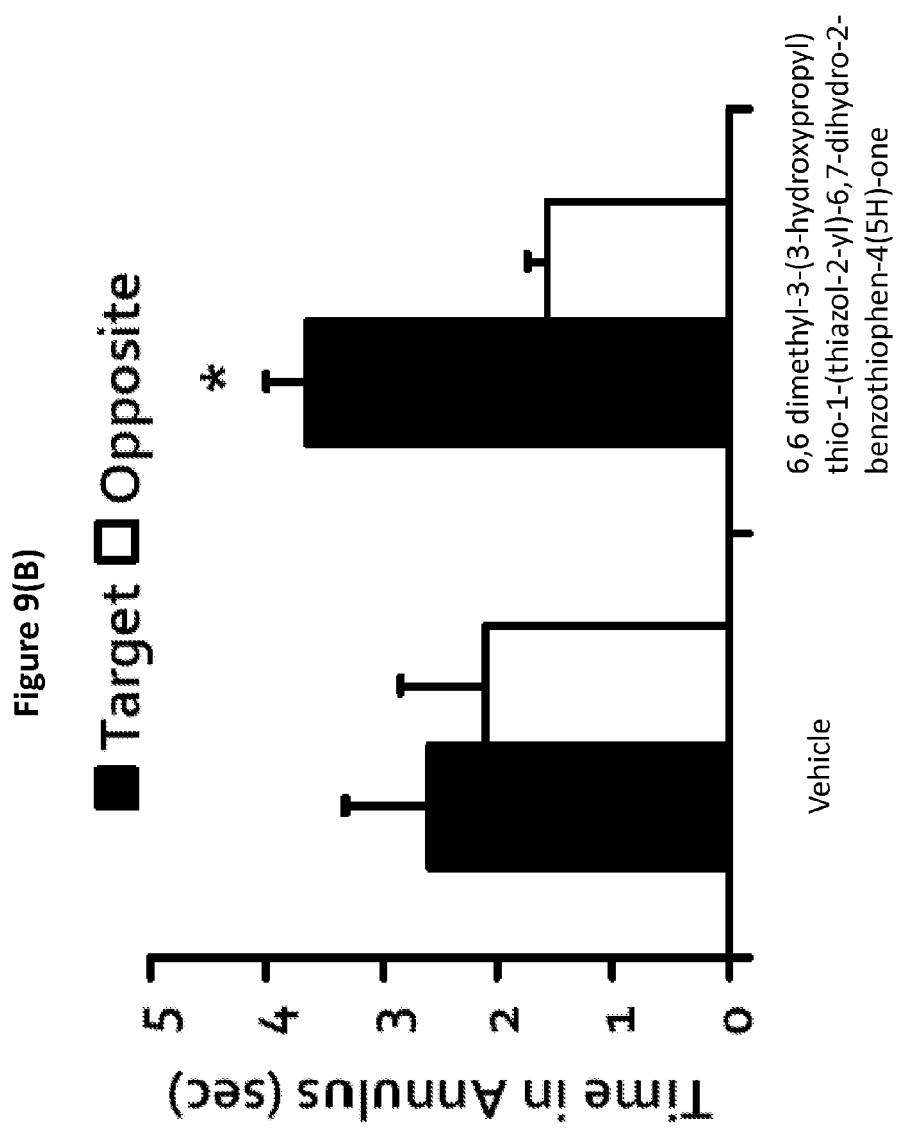

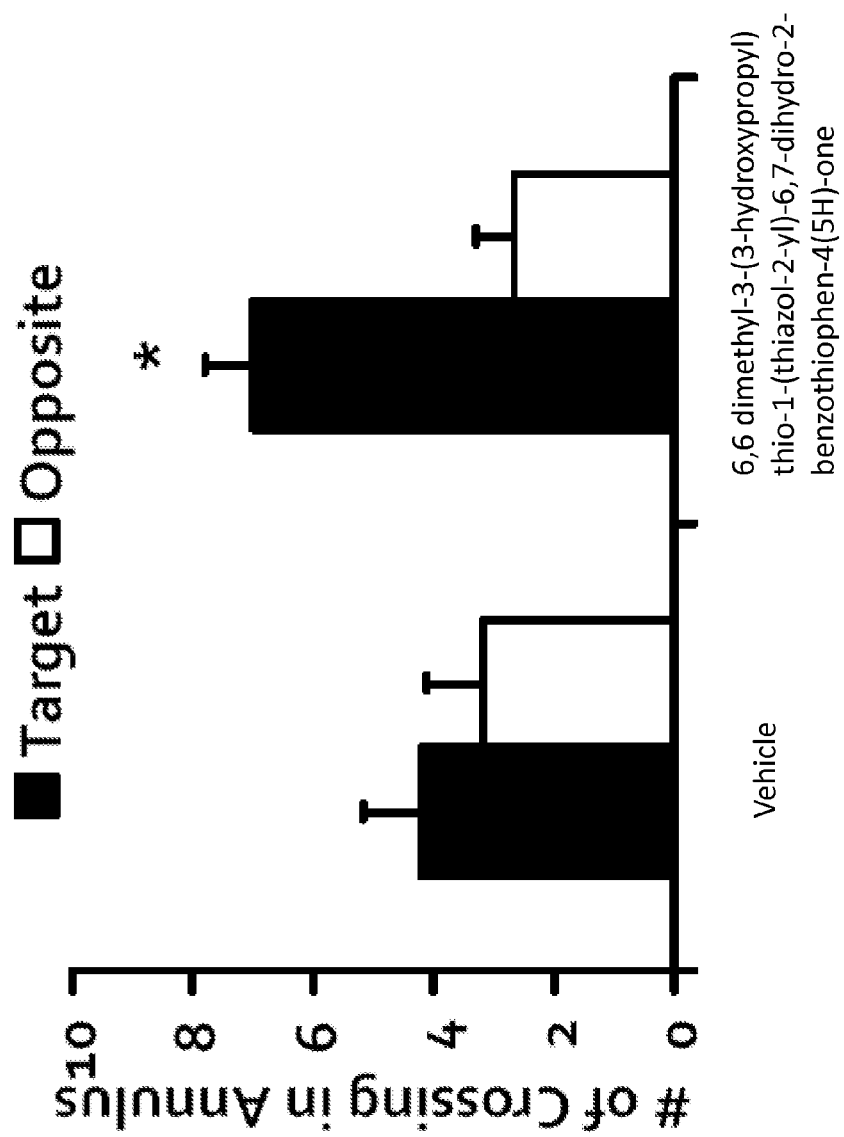

PYRIDAZINE DERIVATIVES, COMPOSITIONS AND METHODS FOR TREATING COGNITIVE IMPAIRMENT

CROSS-REFERENCE TO RELATED APPLICATIONS

This application is a national stage application under 35 U.S.C. §371 of International Application PCT/US2011/060854, filed on Nov. 15, 2011, which application claims priority from U.S. Provisional Patent Application 61/413,971, filed Nov. 15, 2010. The disclosure of each of these referenced applications is incorporated by reference herein in its entirety. International Application PCT/US2011/060854 was published under PCT Article 21(2) in English.

FIELD OF THE INVENTION

This invention relates to compounds, compositions and methods for treating central nervous system (CNS) disorders with cognitive impairment that are responsive to agonists of α5 subunit containing $GABA_A$ receptor, e.g., age-related cognitive impairment, Mild Cognitive Impairment (MCI), dementia, Alzheimer's Disease (AD), prodromal AD, post traumatic stress disorder (PTSD), schizophrenia and cancer-therapy-related cognitive impairment.

BACKGROUND OF THE INVENTION $GABA_A$ receptors ($GABA_A$ R) are pentameric assemblies from a pool of different subunits ($\alpha$1-6, $\beta$1-3, $\gamma$1-3, $\delta$, $\epsilon$, $\pi$, $\theta$) that forms a Cl– permeable channel that is gated by the neurotransmitter γ-aminobutyric acid (GABA). Various pharmacological effects, including anxiety disorders, epilepsy, insomnia, pre-anesthetic sedation, and muscle relaxation, are mediated by different $GABA_A$ subtypes.

Various studies have demonstrated that reduced GABA signaling is linked to various CNS disorders with cognitive impairment. In particular, the α5-containing $GABA_A$ Rs, which are relatively sparse in the mammalian brain, play a role in modifying learning and memory. Previous studies demonstrated a reduction of hippocampal expression of the α5 subunit of the $GABA_A$ receptor in rats with age-related cognitive decline (see International Patent Publication WO 2007/019312). Such results suggest that upregulation of α5-containing $GABA_A$ R function may be effective in the treatment of CNS disorders with cognitive impairment, e.g., age-related cognitive impairment, Mild Cognitive Impairment (MCI), dementia, Alzheimer's Disease (AD), prodromal AD, PTSD, schizophrenia and cancer-therapy-related cognitive impairment.

Thus, there is a need for agonists of α5-containing $GABA_A$ R that are useful in therapeutic preparations for the treatment of CNS disorders with cognitive impairment.

SUMMARY OF THE INVENTION

The present invention addresses the aforementioned need by providing compounds of Formula I:

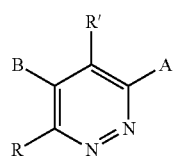

I or a pharmaceutically acceptable salt thereof, wherein:
R' is —COOH, —C(O)NR¹R², or a 5-membered heterocyclic or heteroaryl ring having 1-3 heteroatoms selected from N, NH, O, SO, and $SO_2$; wherein the 5-membered heterocyclic or heteroaryl ring has 0-3 substituents selected independently from J;

$R^1$ and $R^2$ are independently selected from:
  H—,
  (C1-C12)-aliphatic-,
  (C3-C10)-cycloalkyl-,
  (C3-C10)-cycloalkenyl-,
  (C6-C10)-aryl-,
  (C5-C10)-heteroaryl-, and (C3-C10)-hetero cyclo-;
  or $R^1$ and $R^2$ may be taken together with the nitrogen atom to which they are attached to form a 3- to 10-membered aromatic or non-aromatic ring having 0-3 substituents independently selected from J, and having 0-3 additional heteroatoms independently selected from N, O, S, SO, or $SO_2$;
  wherein each of $R^1$ and $R^2$ is independently substituted at each substitutable position with 0-3 substituents independently selected from J;

R is H, halogen or (C1-C12)-aliphatic-, wherein said (C1-C12)-aliphatic group is substituted with 0-3 substituents independently selected from J;

A and B are each independently selected from:
  (C6-C10)-aryl-,
  (C5-C10)-heteroaryl-, and
  (C3-C10)-heterocyclo-;

wherein A and B are each independently substituted with 0-5 substituents independently selected from J;

each J is independently selected from:
  halogen, —$OR^3$, —$NO_2$, —CN, —$CF_3$, —$OCF_3$, —$R^3$, oxo, thioxo, 1,2-methylenedioxy, 1,2-ethylenedioxy, =N($R^3$), =N(O$R^3$), —N($R^3$)$_2$, —S$R^3$, —SO$R^3$, —SO$_2R^3$, —SO$_2$N($R^3$)$_2$, —SO$_3R^3$, —C(O)$R^3$, —C(O)C(O)$R^3$, —C(O)CH$_2$C(O)$R^3$, —C(S)$R^3$, —C(S)O$R^3$, —C(O)O$R^3$, —C(O)C(O)O$R^3$, —C(O)C(O)N($R^3$)$_2$, —OC(O)$R^3$, —C(O)N($R^3$)$_2$, —OC(O)N($R^3$)$_2$, —C(S)N($R^3$)$_2$, —(CH$_2$)$_{0-2}$NHC(O)$R^3$, —N($R^3$)N($R^3$)CO$R^3$, —N($R^3$)N($R^3$)C(O)O$R^3$, —N($R^3$)N($R^3$)CON($R^3$)$_2$, —N($R^3$)SO$_2R^3$, —N($R^3$)SO$_2$N($R^3$)$_2$, —N($R^3$)C(O)O$R^3$, —N($R^3$)C(O)$R^3$, —N($R^3$)C(S)$R^3$, —N($R^3$)C(O)N($R^3$)$_2$, —N($R^3$)C(S)N($R^3$)$_2$, —N(COR$^3$)COR$^3$, —N(O$R^3$)$R^3$, —C(=NH)N($R^3$)$_2$, —C(O)N(O$R^3$)$R^3$, —C(=NO$R^3$)$R^3$, —OP(O)(O$R^3$)$_2$, —P(O)($R^3$)$_2$, —P(O)(O$R^3$)$_2$, and —P(O)(H)(O$R^3$);

each $R^3$ is independently selected from:
  H—,
  (C1-C12)-aliphatic-,
  (C3-C10)-cycloalkyl-,
  (C3-C10)-cycloalkenyl-,
  [(C3-C10)-cycloalkyl]-(C1-C12)-aliphatic-,
  [(C3-C10)-cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, and
  (C5-C10)-heteroaryl-(C1-C12)-aliphatic-;
  or two $R^3$ groups bound to the same atom may be taken together with the atom to which they are bound to form a 3- to 10-membered aromatic or non-aromatic ring having 1-3 heteroatoms independently selected from N, O, S, SO, and $SO_2$, wherein said ring is optionally fused to a (C6-C10)aryl, (C5-C10)heteroaryl, (C3-C10)cycloalkyl, or a (C3-C10)heterocyclyl;

provided that said compound of formula I is not:

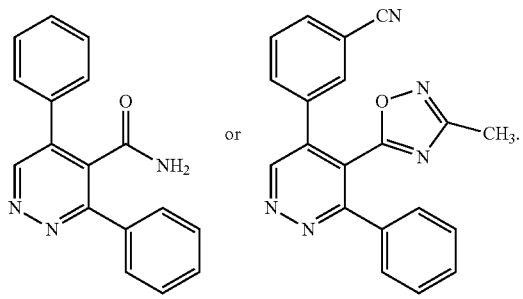 [SMILES: NC(=O)c1c(-c2ccccc2)cnnc1-c1ccccc1 ; "or" ; Cc1noc(-c2c(-c3cccc(C#N)c3)cnnc2-c2ccccc2)n1]

Compounds of Formula I can be used to treat the conditions described herein, such as through activity as $GABA_A$ α5 receptor agonists.

The present invention also provides compositions that comprise the above compounds or a pharmaceutically acceptable salt thereof.

In another aspect of the invention, there is provided a method for treating CNS disorder with cognitive impairment in a subject in need or at risk thereof, the method comprising the step of administering to said subject a therapeutically effective amount of a $GABA_A$ α5 receptor agonist or a pharmaceutically acceptable salt thereof. In certain embodiments of the invention, the $GABA_A$ α5 receptor agonist or a pharmaceutically acceptable salt thereof is administered every 12 or 24 hours.

DETAILED DESCRIPTION OF THE FIGURES

Figure 1C:
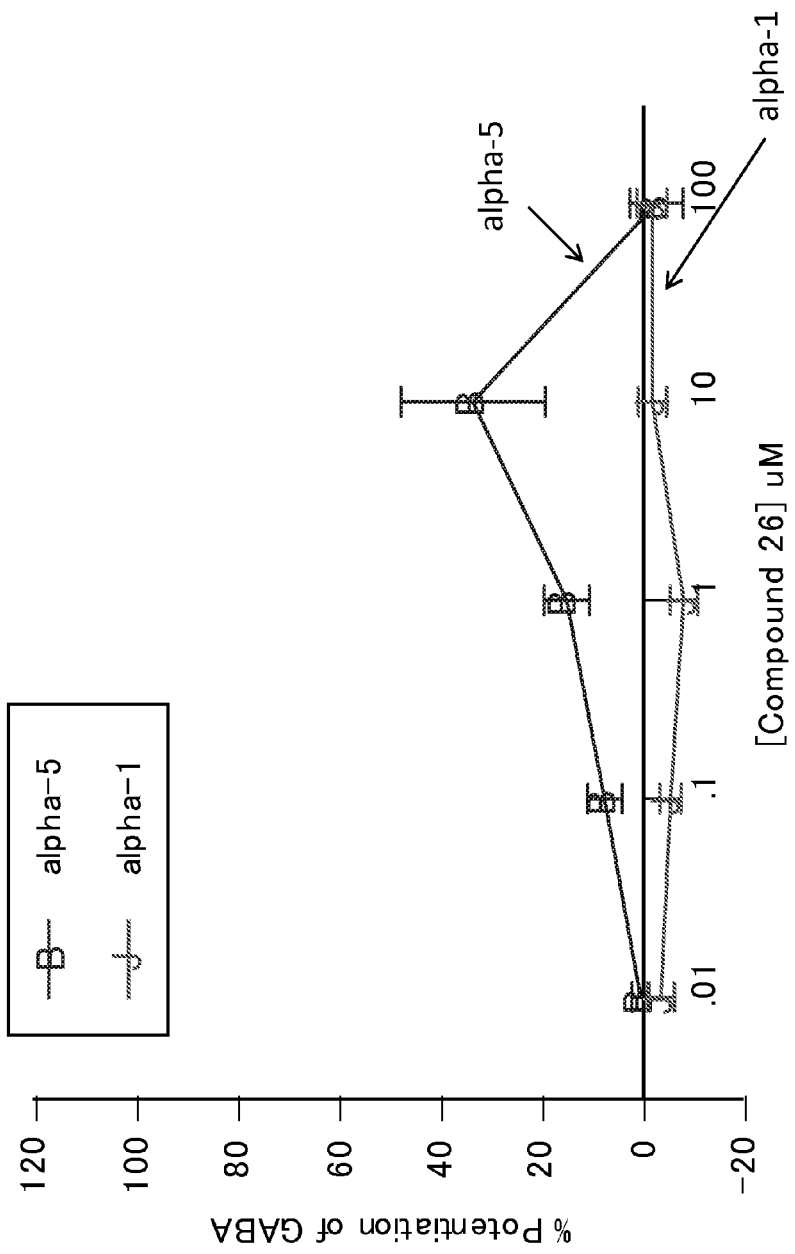
Figure 1D:
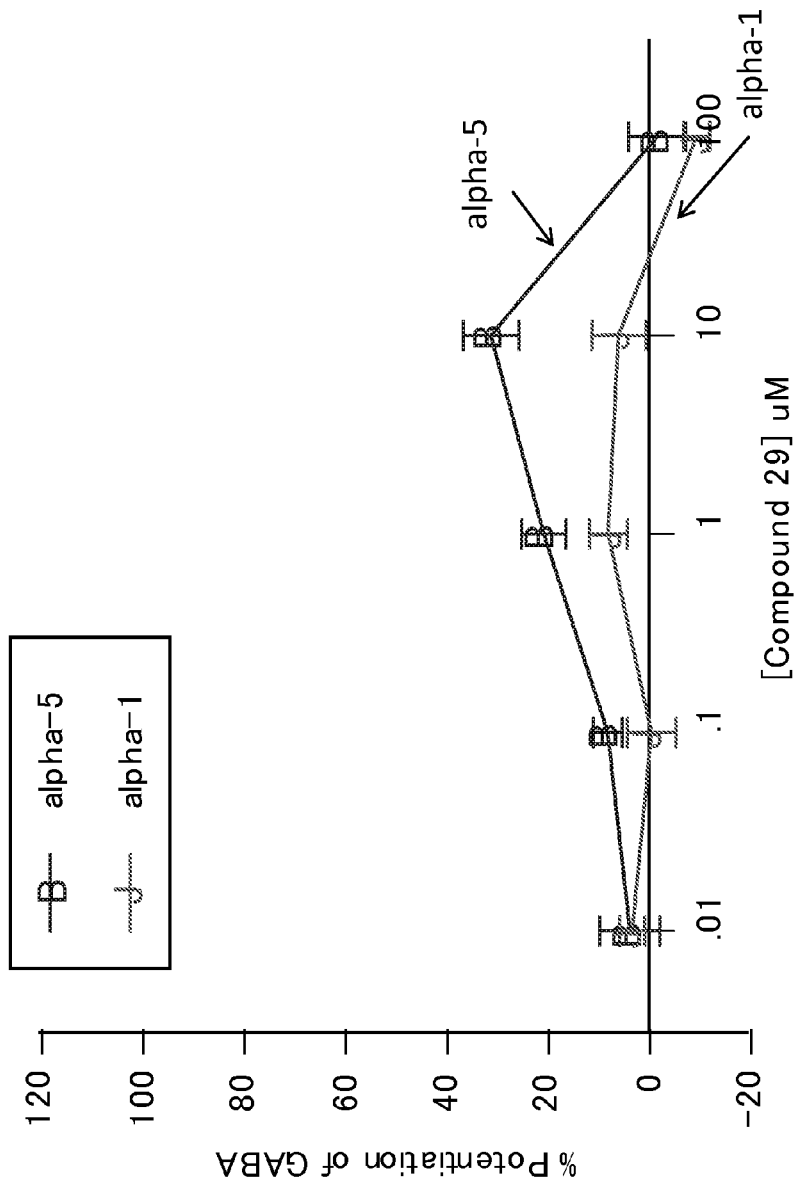

FIGS. 1(A)-(D) are graphs showing functional selectivity data, as demonstrated by the potentiation of GABA EC50 concentration in *Xenopus oocytes* containing $GABA_A$ α5 receptors (α5β3γ2) vs. α1 receptors (α1β2γ2), in the presence of test compounds. FIG. 1(A) shows the functional selectivity data for compound 4; FIG. 1(B) shows the functional selectivity data for compound 27; FIG. 1(C) shows the functional selectivity data for compound 26; and FIG. 1(D) shows the functional selectivity data for compound 29.

Figure 2:
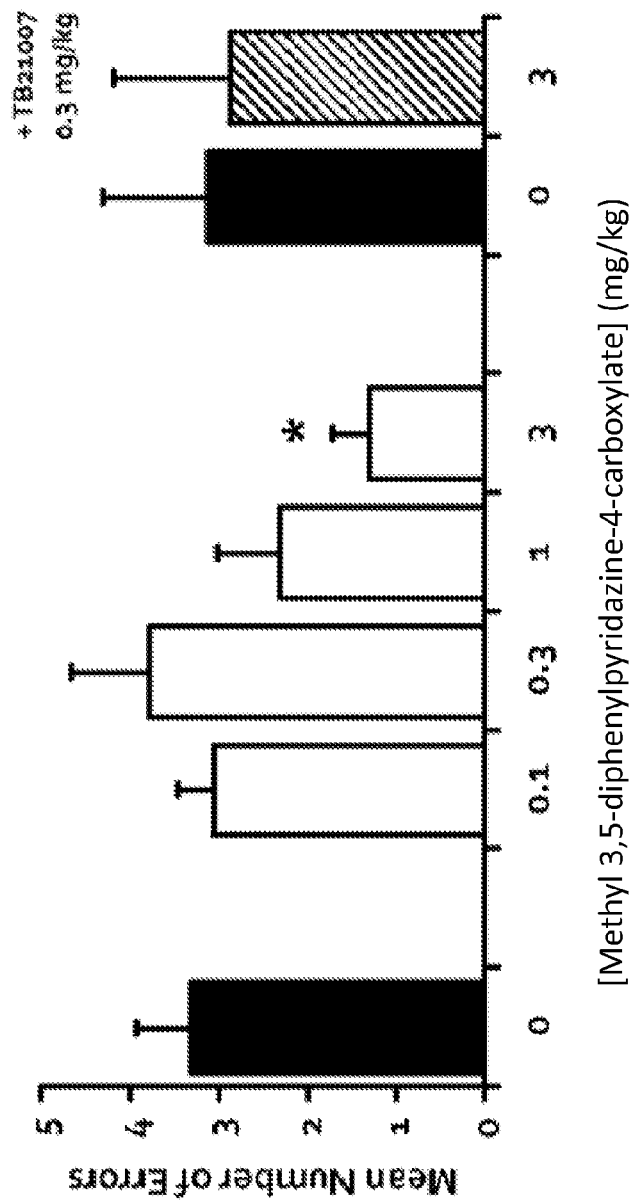

FIG. 2 is a graph depicting the effects of administering methyl 3,5-diphenylpyridazine-4-carboxylate on the spatial memory retention of ten aged-impaired (AI) rats in an eight-arm Radial Arm Maze (RAM) test. The black bars refer to rats treated with vehicle alone; open bars refer to rats treated with methyl 3,5-diphenylpyridazine-4-carboxylate at different doses; hatched bar refers to rats treated with the combination of TB21007 and methyl 3,5-diphenylpyridazine-4-carboxylate.

Figure 3:
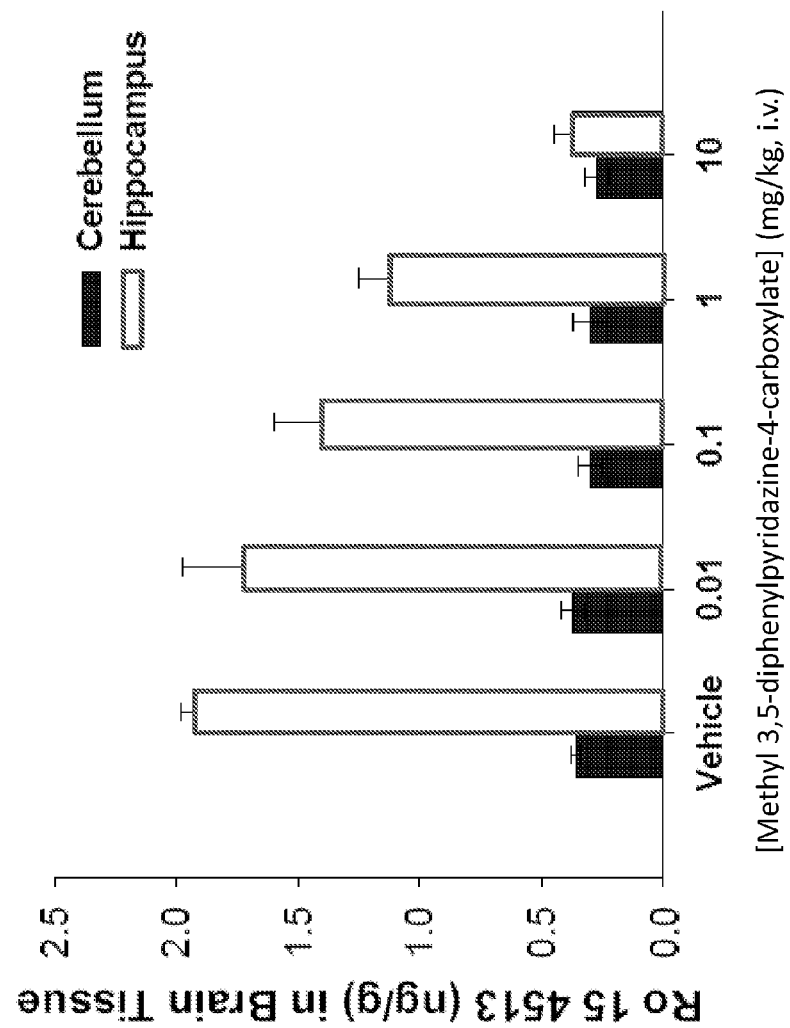

FIG. 3 is a graph showing the effect of methyl 3,5-diphenylpyridazine-4-carboxylate (administered intravenously) on the binding of Ro154513 in the hippocampus and cerebellum. Methyl 3,5-diphenylpyridazine-4-carboxylate blocked the binding of Ro154513 in the hippocampus but did not affect binding of Ro15413 in the cerebellum.

Figure 4:
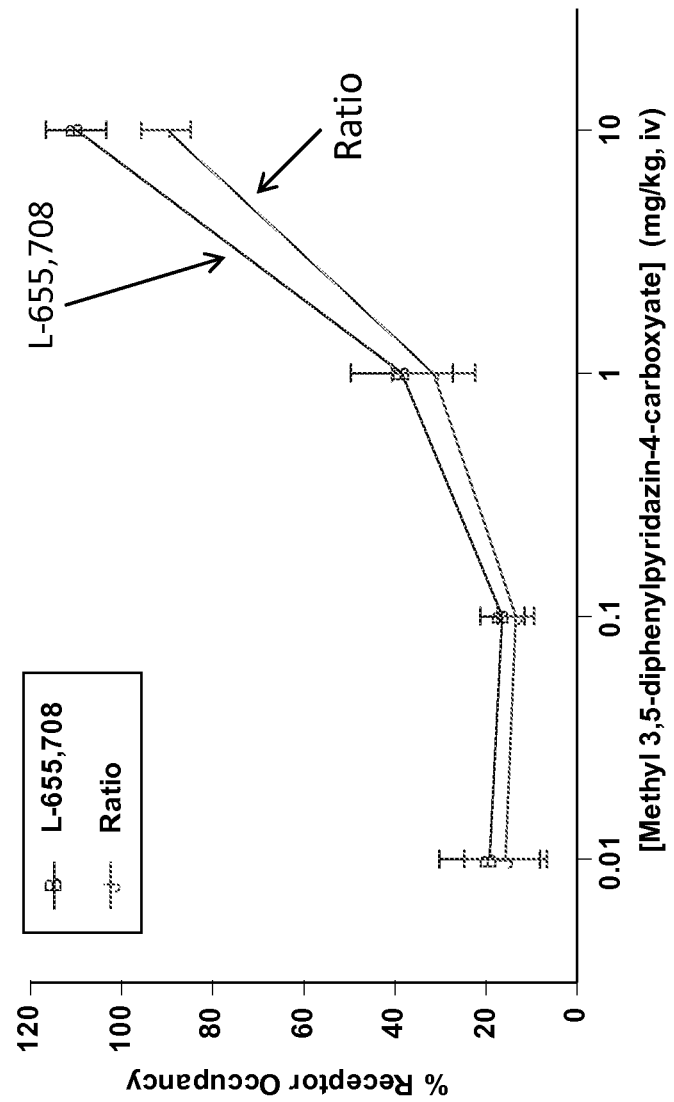

FIG. 4 is a graph showing dose-dependent $GABA_A$ α5 receptor occupancy by methyl 3,5-diphenylpyridazine-4-carboxylate administered intravenously, with receptor occupancy determined either by the ratio between hippocampus (a region of high $GABA_A$ α5 receptor density) exposure of RO 15-4513 and cerebellum (a region with low $GABA_A$ α5 receptor density) exposure of RO 15-4513, or by using the $GABA_A$ α5 selective compound L-655,708 (10 mg/kg, i.v.) to define full occupancy.

Figure 5:
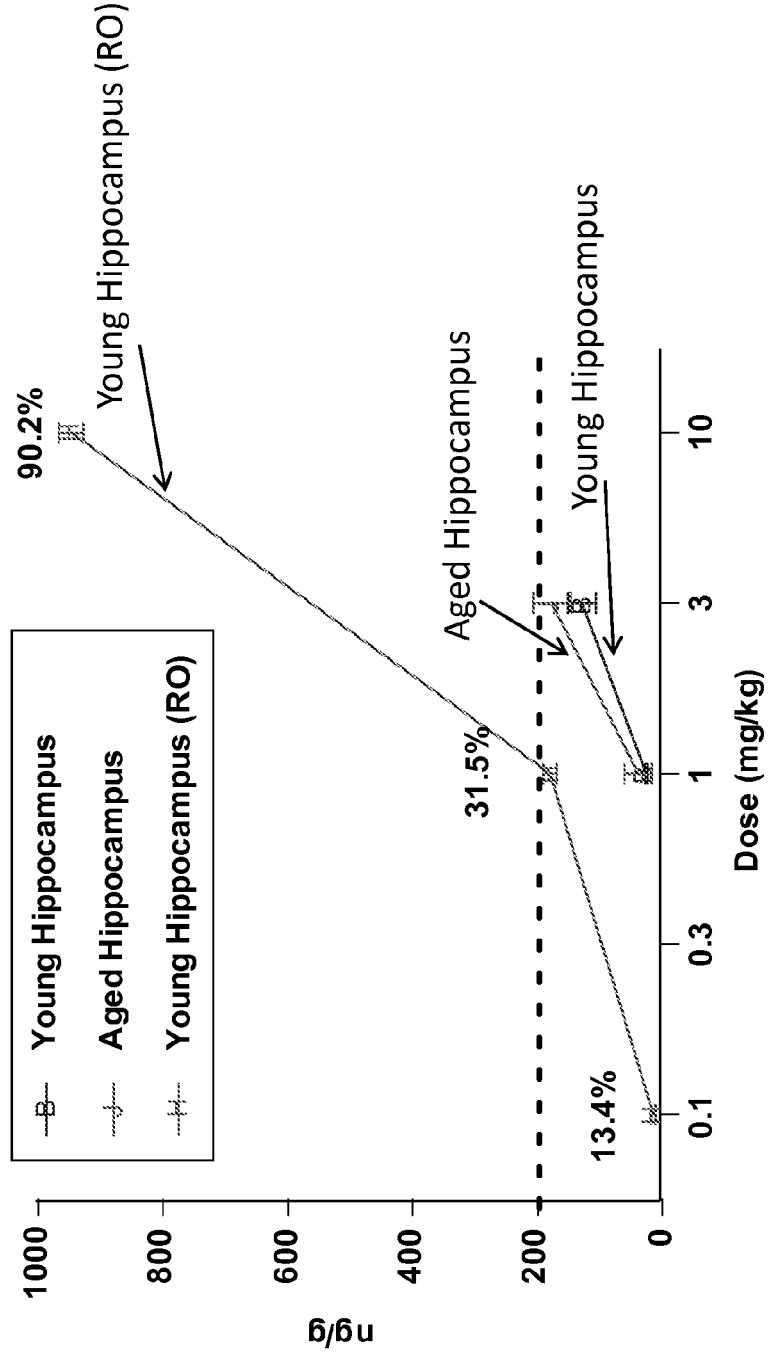

FIG. 5 is a graph showing exposure occupancy relationships for methyl 3,5-diphenylpyridazine-4-carboxylate in hippocampus. Methyl 3,5-diphenylpyridazine-4-carboxylate occupies about 32% of $GABA_A$ α5 receptors at exposures which are behaviorally active in aged-impaired rats.

Figure 6A:
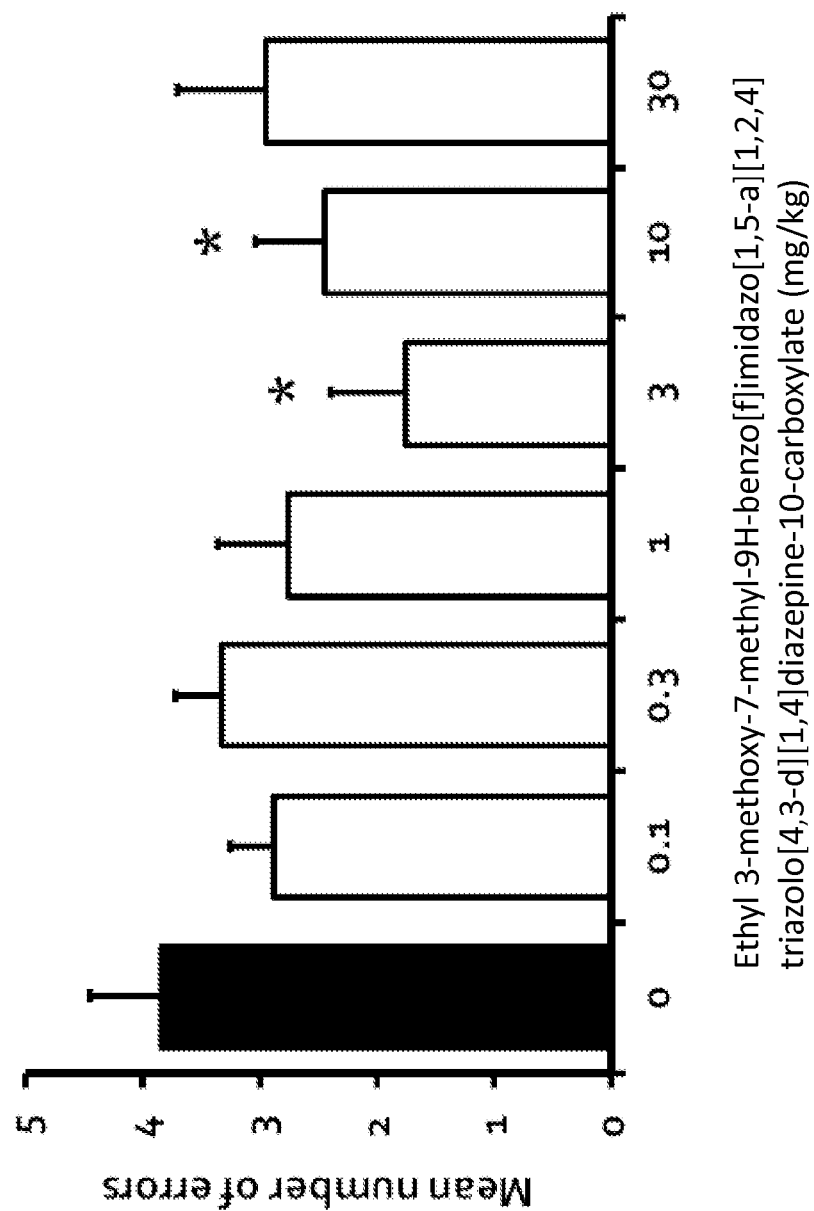
Figure 6B:
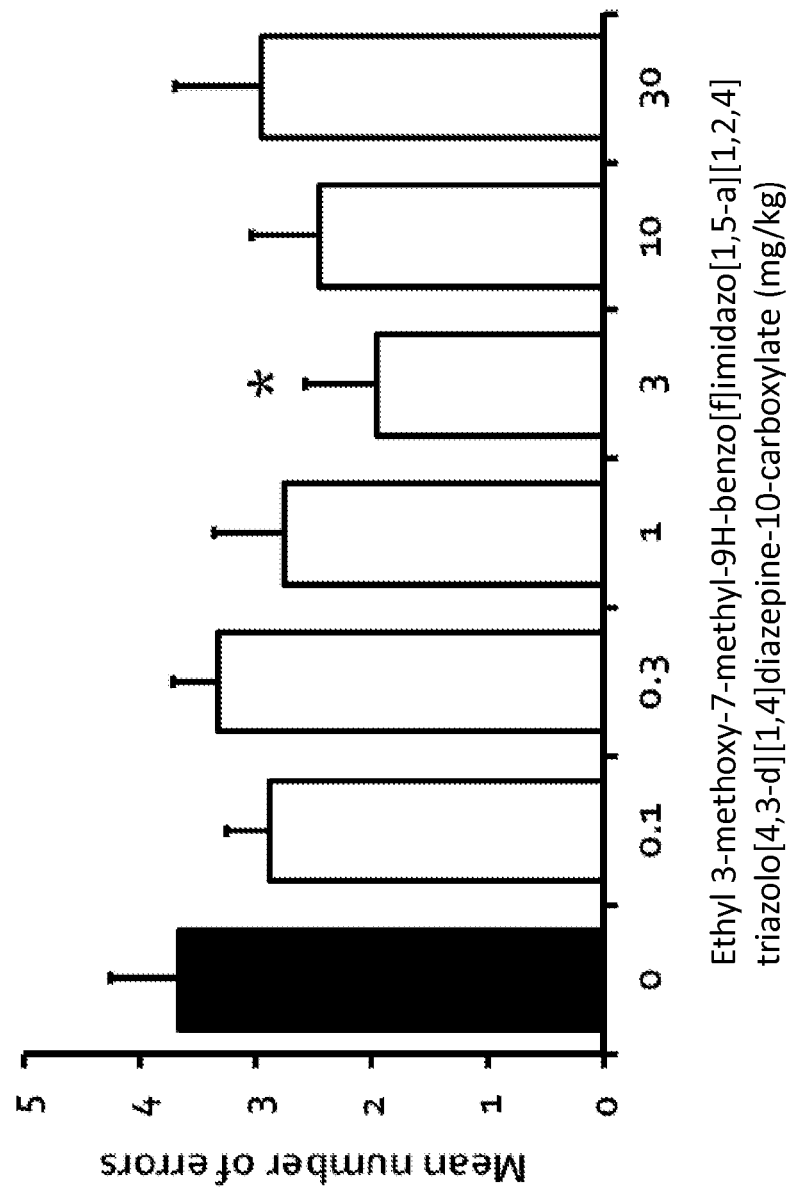

FIGS. 6(A)-(B) are graphs depicting the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in an eight-arm Radial Arm Maze (RAM) test. FIG. 6(A) shows the effect of ethyl 3-methoxy-7-methyl-9H-benzo Wimidazo[1,5-a][1,2,4]triazolo[4,3-d][1,4]diazepine-10-carboxylate on the spatial memory retention of ten aged-impaired (AI) rats in the RAM test, where the vehicle control was tested 3 times, and the different doses of ethyl 3-methoxy-7-methyl-9H-benzo[f]imidazo[1,5-a][1,2,4]triazolo[4,3-d][1,4]diazepine-10-carboxylate were tested twice; FIG. 6(B) shows the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in the RAM test, where the vehicle control was tested 5 times, the 3 mg/kg dose of ethyl 3-methoxy-7-methyl-9H-benzo[f]imidazo[1,5-a][1,2,4]triazolo[4,3-d][1,4]diazepine-10-carboxylate was tested 4 times, and the other doses of ethyl 3-methoxy-7-methyl-9H-benzo[f]imidazo[1,5-a][1,2,4]triazolo[4,3-d][1,4]diazepine-10-carboxylate were tested twice. In both FIGS. 6(A) and 6(B), black bars refer to rats treated with vehicle alone and open bars refer to rats treated with ethyl 3-methoxy-7-methyl-9H-benzo[f]imidazo[1,5-a][1,2,4]triazolo[4,3-d][1,4]diazepine-10-carboxylate at different doses.

Figure 7:
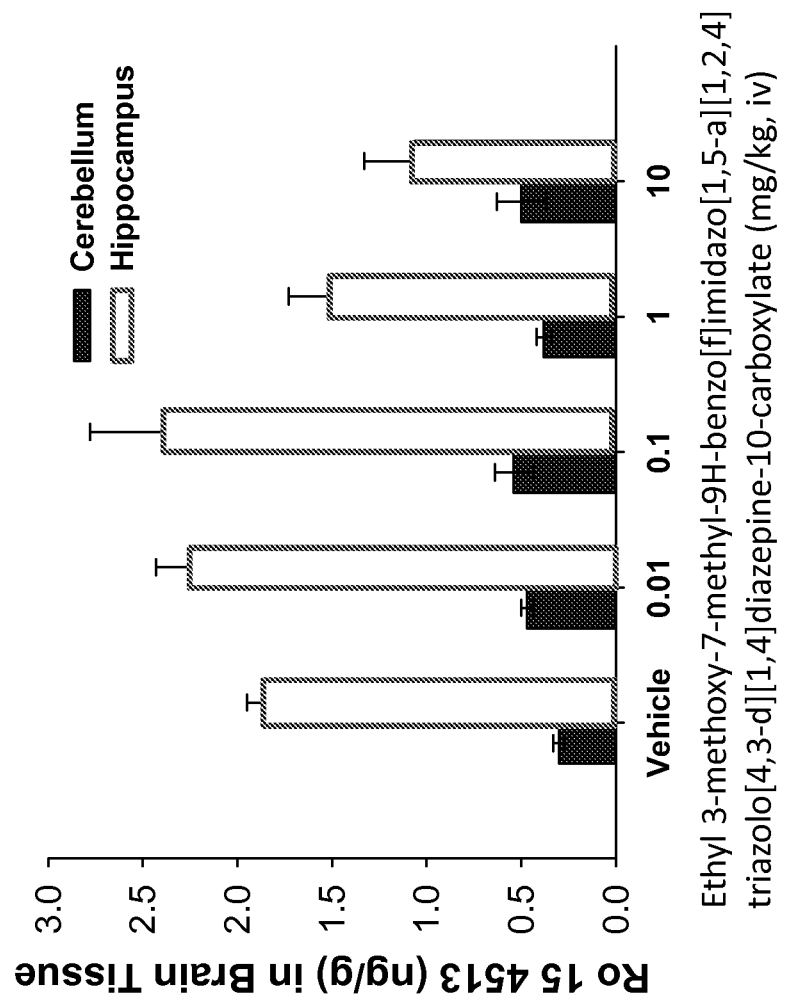

FIG. 7 is a graph showing the effect of ethyl 3-methoxy-7-methyl-9H-benzo[f]imidazo[1,5-a][1,2,4]triazolo[4,3-d][1,4]diazepine-10-carboxylate (administered intravenously) on the binding of Ro154513 in the hippocampus and cerebellum. Ethyl 3-methoxy-7-methyl-9H-benzo[f]imidazo[1,5-a][1,2,4]triazolo[4,3-d][1,4]diazepine-10-carboxylate blocked the binding of Ro154513 in the hippocampus but did not affect binding of Ro15413 in the cerebellum.

Figure 8:
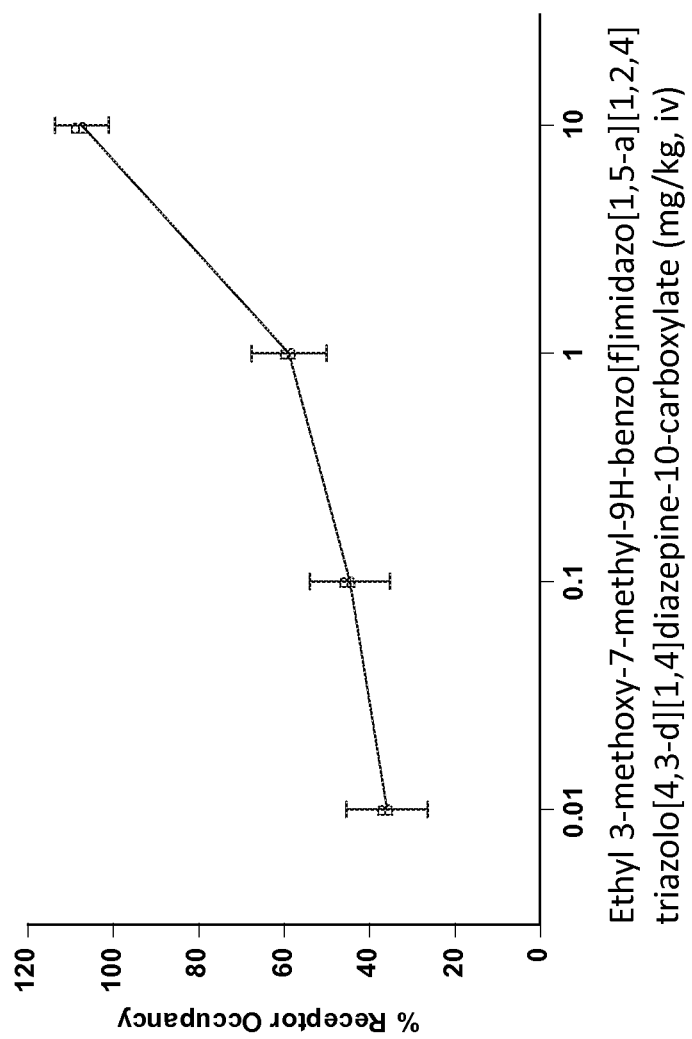

FIG. 8 is a graph showing dose-dependent $GABA_A$ α5 receptor occupancy by ethyl 3-methoxy-7-methyl-9H-benzo[f]imidazo[1,5-a][1,2,4]triazolo[4,3-d][1,4]diazepine-10-carboxylate administered intravenously, as calculated by the ratio between hippocampus (a region of high $GABA_A$ α5 receptor density) exposure of RO 15-4513 and cerebellum (a region with low $GABA_A$ α5 receptor density) exposure of RO 15-4513 to define full occupancy.

Figure 9A:
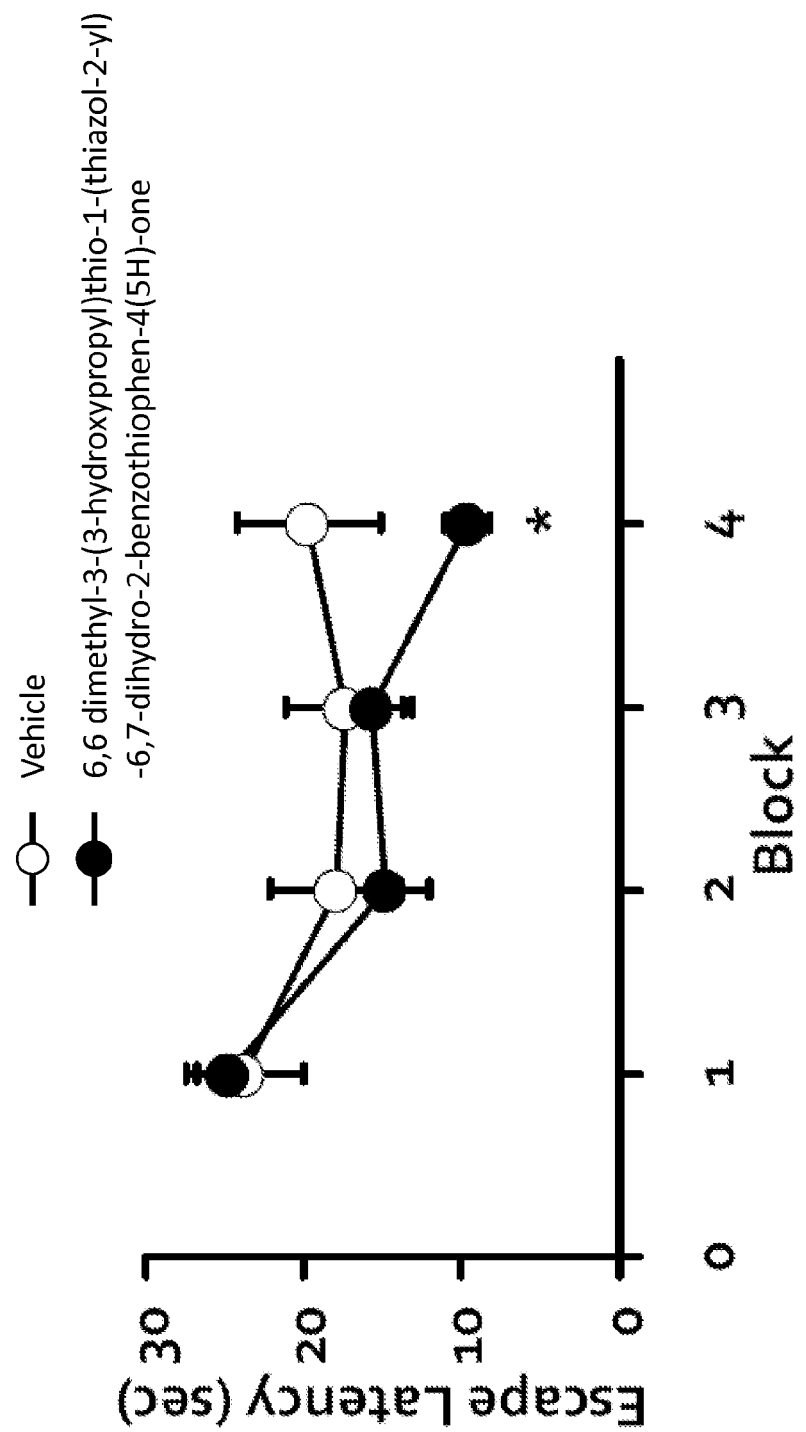

FIG. 9(A)-(C) are graphs showing the effect of 6,6 dimethyl-3-(3-hydroxypropyl)thio-1-(thiazol-2-yl)-6,7-dihydro-2-benzothiophen-4(5H)-one, as compared to vehicle dimethyl sulfoxide (DMSO), in aged-impaired rats using a Morris water maze behavioral task. FIG. 9(A) shows the escape latency (i.e., the average time in seconds rats took to find the hidden platform in the water pool) during training in rats received 6,6 dimethyl-3-(3-hydroxypropyl)thio-1-(thiazol-2-yl)-6,7-dihydro-2-benzothiophen-4(5H)-one and rats received vehicle DMSO; FIG. 9(B) shows the amount of time spent in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO; FIG. 9(C) shows number of crossing in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO.

DETAILED DESCRIPTION OF THE INVENTION

(1) Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The term "agent" is used herein to denote a chemical compound (such as an organic or inorganic compound (including, such as, a compound of the present invention), a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents that are known with respect to structure, and those that are not known with respect to structure. The $\alpha 5$-containing $GABA_A$ R agonist activity of such agents may render them suitable as "therapeutic agents" in the methods and compositions of this invention.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). See Folstein et al., *J Psychiatric Res* 12: 189-98, (1975); Robbins et al., *Dementia* 5: 266-81, (1994); Rey, L'examen clinique en psychologie, (1964); Kluger et al., *J Geriatr Psychiatry Neurol* 12:168-79, (1999).

In animal model systems, cognitive function may be measured in various conventional ways known in the art, including using a Morris Water Maze (MWM), Barnes circular maze, elevated radial arm maze, T maze or any other mazes in which the animals use spatial information. Other tests of cognitive function in animals include prepulse inhibition, latent inhibition, object recognitions test, delayed non-match to sample test, reaction time tasks, attentional set shifting, cross-maze set shifting task, social interaction task, and social recognition test.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Promoting" cognitive function refers to affecting impaired cognitive function so that it more closely resembles the function of an aged-matched normal, unimpaired subject, or the function of a young adult subject. Cognitive function may be promoted to any detectable degree, but in humans preferably is promoted sufficiently to allow an impaired subject to carry out daily activities of normal life at the same level of proficiency as an aged-matched normal, unimpaired subject or as a young adult subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Cognitive impairment" refers to cognitive function in subjects that is not as robust as that expected in an age-matched normal subject (i.e. subjects with mean scores for a given age in a cognitive test). In some cases, cognitive function is reduced by about 5%, about 10%, about 30%, or more, compared to cognitive function expected in an age-matched normal subject.

"Age-related cognitive impairment" refers to cognitive impairment in aged subjects, wherein their cognitive function is not as robust as that expected in an age-matched normal subject or as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI) (including amnestic MCI and non-amnestic MCI), Age-Associated Memory Impairment (AAMI), and Age-related Cognitive Decline (ARCD).

"Mild Cognitive Impairment" or "MCI" refers to a condition characterized by low-level cognitive deficit causing no problems in normal activities of daily living. A clinical characterization of MCI may comprise: presence of a cognitive complaint in at least one cognitive domain expressed by subject or informant, objective evidence of impairment on neuropsychological testing of at least 1.5 standard deviations below norms matched for age, and activities of daily living remaining intact. The cognitive deficit in subjects with MCI may involve any cognition area or mental process including memory, language, association, attention, perception, problem solving, executive function and visuospatial skills. See, e.g., Winbald et al., *J. Intern. Med.* 256:240-240, 2004; Meguro, *Acta. Neural. Taiwan.* 15:55-57, 2008; Ellison et al., *CNS Spectr.* 13:66-72, 2008, Petersen, *Semin. Neural.* 27:22-31, 2007. MCI is further subdivided into amnestic MCI (aMCI) and non-amnestic MCI, characterized by the impairment (or lack thereof) of memory in particular. MCI is defined as aMCI if memory is found to be impaired given the age and education level of the subject. If, on the other hand, the memory of the subject is found to be intact for age and education, but other non-memory cognitive domains are impaired, such as language, executive function, or visuospatial skills, MCI is defines an non-amnestic MCI. aMCI and non-amnestic MCI can both be further subdivided into single or multiple domain MCI. aMCI-single domain refers to a condition where memory, but not other cognitive areas are impaired. aMCI-multiple domain refers to a condition where memory and at least one other cognitive area are impaired. Non-amnestic MCI is single domain or multiple domain dependent on whether nor not more than one non-memory cognitive area is impaired. See, e.g., Peterson and Negash, *CNS Spectr.* 13:45-53, 2008.

"Age-Associate Memory Impairment (AAMI)" refers to a decline in memory due to aging. A patient may be considered to have AAMI if he or she is at least 50 years old and meets all of the following criteria: a) the patient has noticed a decline in memory performance, b) the patient performs worse on a standard test of memory compared to young adults, and c) all other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline, is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

"Dementia" refers to a condition characterized by severe cognitive deficit that interferes in normal activities of daily living. Subjects with dementia also display other symptoms such as impaired judgment, changes in personality, disorientation, confusion, behavior changes, trouble speaking, and motor deficits. There are different types of dementias, such as Alzheimer's disease (AD), vascular dementia, dementia with Lewy bodies, and frontotemporal dementia.

Alzheimer's disease (AD) is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

Vascular dementia is caused by strokes. Symptoms overlap with those of AD, but without the focus on memory impairment.

Dementia with Lewy bodies is characterized by abnormal deposits of alpha-synuclein that form inside neurons in the brain. Cognitive impairment may be similar to AD, including impairments in memory and judgment and behavior changes.

Frontotemporal dementia is characterized by gliosis, neuronal loss, superficial spongiform degeneration in the frontal cortex and/or anterior temporal lobes, and Picks' bodies. Symptoms include changes in personality and behavior, including a decline in social skills and language expression/comprehension.

"Post traumatic stress disorder (PTSD)" refers to an anxiety disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses produce anxiety and can have significant impact, both chronic and acute, on a patient's quality of life and physical and emotional health. PTSD is also associated with impaired cognitive performance, and older individuals with PTSD have greater decline in cognitive performance relative to control patients.

"Schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. While abnormalities in the brain are proposed to underlie the full spectrum of psychopathology in schizophrenia, currently available antipsychotics are largely ineffective in treating cognitive impairments in patients.

"Cancer therapy-related cognitive impairment" refers to cognitive impairment that develops in subjects that are treated with cancer therapies such as chemotherapy and radiation. Cytotoxicity and other adverse side-effects on the brain of cancer therapies result in cognitive impairment in such functions as memory, learning and attention.

"Treating" a condition or patient refers to taking steps to obtain beneficial or desired results, including clinical results. Beneficial or desired clinical results include, but are not limited to, alleviation, amelioration, or slowing the progression, of one or more symptoms associated with age-related cognitive impairment, Mild Cognitive Impairment (MCI), dementia, Alzheimer's Disease (AD), prodromal AD, PTSD, schizophrenia and cancer therapy-related cognitive impairment.

"Treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of an aged-matched normal, unimpaired subject, or the function of a young adult subject. Treatment of cognitive impairment in humans may improve cognitive function to any detectable degree, but is preferably improved sufficiently to allow the impaired subject to carry out daily activities of normal life at the same level of proficiency as an aged-matched normal, unimpaired subject or as a young adult subject.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or Formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity). Preferably, a compound or an agent is administered orally, e.g., to a subject by ingestion. In some embodiments, the orally administered compound or agent is in an extended release or slow release Formulation, or administered using a device for such slow or extended release.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of cognitive impairment or other symptoms of the CNS disorder (such as age-related cognitive impairment, Mild Cognitive Impairment (MCI), dementia, Alzheimer's Disease (AD), prodromal AD, PTSD, schizophrenia and cancer therapy-related cognitive impairment), and the therapeutics or combination of therapeutics selected for administration, and the mode of administration. The skilled worker can readily determine the effective amount for a given situation by routine experimentation.

The compounds of the present invention also include prodrugs, analogs or derivatives. The term "prodrug" is art-recognized and is intended to encompass compounds or agents which, under physiological conditions, are converted into a $\alpha 5$-containing $GABA_A$ R agonist. A common method for making a prodrug is to select moieties which are hydrolyzed or metabolized under physiological conditions to provide the desired compound or agent. In other embodiments, the prodrug is converted by an enzymatic activity of the host animal to a $GABA_A$ $\alpha 5$ receptor agonist.

An "$\alpha 5$-containing $GABA_A$ R agonist" or a "$GABA_A$ $\alpha 5$ receptor agonist" as used herein refer to a compound that up-regulates the function of $\alpha 5$-containing $GABA_A$ R, i.e., a compound that increase GABA-gated $Cl^-$ currents. In some embodiments, $\alpha 5$-containing $GABA_A$ R agonist as used herein refers to a positive allosteric modulator, which potentiates the activity of GABA.

"Analog" is used herein to refer to a compound which functionally resembles another chemical entity, but does not share the identical chemical structure. For example, an analog is sufficiently similar to a base or parent compound such that it can substitute for the base compound in therapeutic applications, despite minor structural differences. i.e., be a $GABA_A$ $\alpha 5$ receptor agonist.

"Derivative" is used herein to refer to the chemical modification of a compound. Chemical modifications of a compound can include, for example, replacement of hydrogen by an alkyl, acyl, or amino group. Many other modifications are also possible.

The term "aliphatic" as used herein means a straight chained or branched alkyl, alkenyl or alkynyl. It is understood that alkenyl or alkynyl embodiments need at least two carbon atoms in the aliphatic chain. Aliphatic groups typically contains from 1 (or 2) to 12 carbons, such as from 1 (or 2) to 4 carbons.

The term "aryl" as used herein means a monocyclic or bicyclic carbocyclic aromatic ring system. For example, aryl as used herein can be a C5-C10 monocyclic or C8-C12 bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin.

The term "heterocyclic" as used herein means a monocyclic or bicyclic non-aromatic ring system having 1 to 3 heteroatom or heteroatom groups in each ring selected from O, N, NH, S, SO, or $SO_2$ in a chemically stable arrangement. For example, heterocyclic as used herein can be a C5-C10 monocyclic or C8-C12 bicyclic non-aromatic ring system having 1 to 3 heteroatom or heteroatom groups in each ring selected from O, N, NH, S, SO, or $SO_2$ in a chemically stable arrangement. In a bicyclic non-aromatic ring system embodiment of "heterocyclyl", one or both rings may contain said heteroatom or heteroatom groups. In another bicyclic "heterocyclyl" embodiment, one of the two rings may be aromatic. In yet another heterocyclic ring system embodiment, a non-aromatic heterocyclic ring may optionally be fused to an aromatic carbocycle.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein means a monocyclic or bicyclic aromatic ring system having 1 to 3 heteroatom or heteroatom groups in each ring selected from O, N, NH or S in a chemically stable arrangement. For example, heteroaryl as used herein can be a C5-C10 monocyclic or C8-C12 bicyclic aromatic ring system having 1 to 3 heteroatom or heteroatom groups in each ring selected from O, N, NH or S in a chemically stable arrangement. In such a bicyclic aromatic ring system embodiment of "heteroaryl":

both rings are aromatic; and
one or both rings may contain said heteroatom or heteroatom groups.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "cycloalkyl or cycloalkenyl" refers to a monocyclic or fused or bridged bicyclic carbocyclic ring system that is not aromatic. For example, cycloalkyl or cycloalkenyl as used herein can be a C5-C10 monocyclic or fused or bridged C8-C12 bicyclic carbocyclic ring system that is not aromatic. Cycloalkenyl rings have one or more units of unsaturation. Preferred cycloalkyl or cycloalkenyl groups include cyclopropyl, cyclobutyl, cyclopentyl, cyclohexyl, cyclohexenyl, cycloheptyl, cycloheptenyl, norbornyl, adamantyl and decalinyl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

"Pharmaceutically acceptable salts" is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present invention. Such solvates include for example hydrates, alcoholates and the like. See, e.g., WO 01/062726.

Many of the compounds useful in the methods and compositions of this invention have at least one stereogenic center in their structure. This stereogenic center may be present in a R or a S configuration, said R and S notation is used in correspondence with the rules described in Pure Appl. Chem. (1976), 45, 11-30.

The invention also relates to all stereoisomeric forms such as enantiomeric and diastereoisomeric forms of the compounds or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the invention includes both mixture and separate individual isomers. Multiple substituents on a piperidinyl or the azepanyl ring can also stand in either cis or trans relationship to each other with respect to the plane of the piperidinyl or the azepanyl ring. Some of the compounds may also exist in tautomeric forms. Such forms, although not explicitly indicated in the formulae described herein, are intended to be included within the scope of the present invention. With respect to the methods and compositions of the present invention, reference to a compound or compounds is intended to encompass that compound in each of its possible isomeric forms and mixtures thereof unless the particular isomeric form is referred to specifically. See, e.g., WO 01/062726.

The invention provides compounds that upregulate the function α5-containing $GABA_A$ R, i.e., α5-containing $GABA_A$ R agonists (or α5-containing $GABA_A$ R positive allosteric modulators) that increase GABA-gated Cl⁻ currents.

The invention further provides pharmaceutical compositions comprising one or more compounds of the invention together with a pharmaceutically acceptable carrier or excipient.

The invention further provides methods for treating CNS disorders with cognitive impairment that are responsive to agonists of α5-containing $GABA_A$ receptor, e.g., age-related cognitive impairment, MCI, dementia, AD, prodromal AD, PTSD, schizophrenia and cancer therapy-related cognitive impairment. In certain embodiments, the method is a method of treating the cognitive impairment associated with age-related cognitive impairment, MCI, dementia, AD, prodromal AD, PTSD, schizophrenia and cancer therapy-related cognitive impairment.

The various CNS disorders with cognitive impairment (e.g., age-related cognitive impairment, MCI, dementia, AD, prodromal AD, PTSD, schizophrenia and cancer therapy-related cognitive impairment) may have a variety of etiologies. However, the symptom of cognitive impairment in each of the above-mentioned disorders may have overlapping causes. Thus, a composition or method of treatment that treats cognitive impairment in one CNS disorder may also treat cognitive impairment in another.

(2) Pyridazine Derivatives and Compositions

The present invention provides a compound of Formula I:

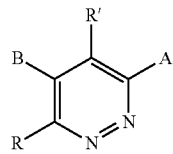

or a pharmaceutically acceptable salt thereof,
wherein:
R' is —COOH, —C(O)NR$^1$R$^2$, or a 5-membered heterocyclic or heteroaryl ring having 1-3 heteroatoms selected from N, NH, O, SO, and SO$_2$; wherein the 5-membered heterocyclic or heteroaryl ring has 0-3 substituents selected independently from J;
R$^1$ and R$^2$ are independently selected from:
H—,
(C1-C12)-aliphatic-,
(C3-C10)-cycloalkyl-,
(C3-C10)-cycloalkenyl-,
(C6-C10)-aryl-,
(C5-C10)-heteroaryl-, and
(C3-C10)-heterocyclo-;
or R$^1$ and R$^2$ may be taken together with the nitrogen atom to which they are attached to form a 3- to 10-membered aromatic or non-aromatic ring having 0-3 substituents independently selected from J, and having 0-3 additional heteroatoms independently selected from N, O, S, SO, or SO$_2$;
wherein each of R$^1$ and R$^2$ is independently substituted at each substitutable position with 0-3 substituents independently selected from J;
R is H, halogen or (C1-C12)-aliphatic-, wherein said (C1-C12)-aliphatic is substituted with 0-3 substituents independently selected from J;
A and B are independently selected from:
(C6-C10)-aryl-,
(C5-C10)-heteroaryl-, and
(C3-C10)-heterocyclo-;
wherein A and B are independently substituted with 0-5 substituents independently selected from J;
each J is independently selected from:
halogen, —OR$^3$, —NO$_2$, —CN, —CF$^3$, —OCF$_3$, —R$^3$, oxo, thioxo, 1,2-methylenedioxy, 1,2-ethylenedioxy, =N(R$^3$), =N(OR$^3$), —N(R$^3$)$_2$, —SR$^3$, —SOR$^3$, —SO$_2$R$^3$, —SO$_2$N(R$^3$)$_2$, —SO$_3$R$^3$, —C(O)R$^3$, —C(O)C(O)R$^3$, —C(O)CH$_2$C(O)R$^3$, —C(S)R$^3$, —C(S)OR$^3$, —C(O)OR$^3$, —C(O)C(O)OR$^3$, —C(O)C(O)N(R$^3$)$_2$, —OC(O)R$^3$, —C(O)N(R$^3$)$_2$, —OC(O)N(R$^3$)$_2$, —C(S)N(R$^3$)$_2$, —(CH$_2$)$_{0-2}$NHC(O)R$^3$, —N(R$^3$)N(R$^3$)COR$^3$, —N(R$^3$)N(R$^3$)C(O)OR$^3$, —N(R$^3$)N(R$^3$)CON(R$^3$)$_2$, —N(R$^3$)SO$_2$R$^3$, —N(R$^3$)SO$_2$N(R$^3$)$_2$, —N(R$^3$)C(O)OR$^3$, —N(R$^3$)C(O)R$^3$, —N(R$^3$)C(S)R$^3$, —N(R$^3$)C(O)N(R$^3$)$_2$, —N(R$^3$)C(S)N(R$^3$)$_2$, —N(COR$^3$)COR$^3$, —N(OR$^3$)R$^3$, —C(=NH)N(R$^3$)$_2$, —C(O)N(OR$^3$)R$^3$, —C(=NOR$^3$)R$^3$, —OP(O)(OR$^3$)$_2$, —P(O)(R$^3$)$_2$, —P(O)(OR$^3$)$_2$, and —P(O)(H)(OR$^3$);

each R$^3$ is independently selected from:
H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
or two R$^3$ groups bound to the same atom may be taken together with the atom to which they are bound to form a 3- to 10-membered aromatic or non-aromatic ring having 1-3 heteroatoms independently selected from N, O, S, SO, and SO$_2$, wherein said ring is optionally fused to a (C6-C10)aryl, (C5-C10)heteroaryl, (C3-C10)cycloalkyl, or a (C3-C10)heterocyclyl.

In some embodiments, the present invention provides a compound of Formula I:

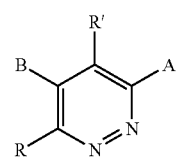

or a pharmaceutically acceptable salt thereof,
wherein:
R' is —C(O)NR$^1$R$^2$ wherein
R$^1$ and R$^2$ are independently selected from:
H—,
(C1-C12)-aliphatic-,
(C3-C10)-cycloalkyl-,
(C3-C10)-cycloalkenyl-,
(C6-C10)-aryl-,
(C5-C10)-heteroaryl-, and (C3-C10)-heterocyclo-;
or R$^1$ and R$^2$ may be taken together with the nitrogen atom to which they are attached to form a 3- to 10-membered aromatic or non-aromatic ring having 0-3 additional heteroatoms independently selected from N, O, S, SO, and SO$_2$;
wherein each of R$^1$ and R$^2$ is independently substituted at each substitutable position with 0-3 substituents independently selected from J;
or R' is a 5-membered heteroaryl ring having 1-3 heteroatoms selected from N, NH, O, SO, and SO$_2$; wherein the 5-membered heteroaryl ring has 0-2 substituents selected independently from J;
R is H, halogen or (C1-C12)-aliphatic-, wherein said C1-C12 aliphatic group is substituted with 0-3 substituents independently selected from J;
A and B are independently selected from:
(C6-C10)-aryl-,
(C5-C10)-heteroaryl-, and
(C3-C10)-heterocyclo-;
wherein A and B are independently substituted with 0-5 substituents independently selected from J;
each J is independently selected from:
halogen, —OR$^3$, —NO$_2$, —CN, —CF$^3$, —OCF$_3$, —R$^3$, oxo, thioxo, 1,2-methylenedioxy, 1,2-ethylenedioxy, =N(R$^3$), =N(OR$^3$), —N(R$^3$)$_2$, —SR$^3$, —SOR$^3$, —SO$_2$R$^3$, —SO$_2$N(R$^3$)$_2$, —SO$_3$R$^3$, —C(O)R$^3$, —C(O)

—C(O)R³, —C(O)CH₂C(O)R³, —C(S)R³, —C(S)OR³, —C(O)OR³, —C(O)C(O)OR³, —C(O)C(O)N(R³)₂, —OC(O)R³, —C(O)N(R³)₂, —OC(O)N(R³)₂, —C(S)N(R³)₂, —(CH₂)₀₋₂NHC(O)R³, —N(R³)N(R³)COR³, —N(R³)N(R³)C(O)OR³, —N(R³)N(R³)CON(R³)₂, —N(R³)SO₂R³, —N(R³)SO₂N(R³)₂, —N(R³)C(O)OR³, —N(R³)C(O)R³, —N(R³)C(S)R³, —N(R³)C(O)N(R³)₂, —N(R³)C(S)N(R³)₂, —N(COR³)COR³, —N(OR³)R³, —C(=NH)N(R³)₂, —C(O)N(OR³)R³, —C(=NOR³)R³, —OP(O)(OR³)₂, —P(O)(R³)₂, —P(O)(OR³)₂, and —P(O)(H)(OR³);

each R³ is independently selected from:
H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;

or two R³ groups bound to the same atom may be taken together with the atom to which they are bound to form a 3- to 10-membered aromatic or non-aromatic ring having 1-3 heteroatoms independently selected from N, O, S, SO, and SO₂, wherein said ring is optionally fused to a (C6-C10)aryl, (C5-C10)heteroaryl, (C3-C10)cycloalkyl, or a (C3-C10)heterocyclyl.

In certain embodiments, the compound of the present invention is not:

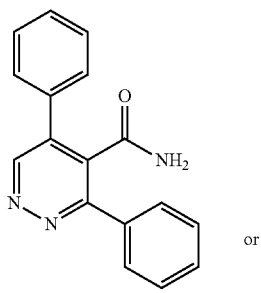

or

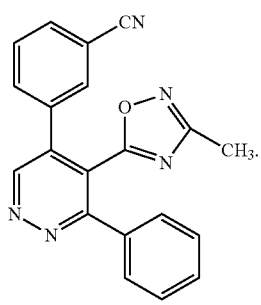

In a more specific embodiment, the invention provides a compound that has the Formula I-A:

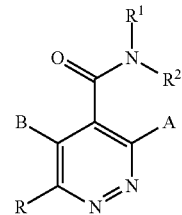

I-A or a pharmaceutically acceptable salt thereof, wherein the variables are as defined in any of the embodiments herein.

In certain embodiments for a compound of Formula I-A, at least one of R¹ and R² is hydrogen. For example, R¹ and R² are each independently hydrogen.

In some embodiments for a compound of Formula I-A, at least one of R¹ and R² is (C1-C12)-aliphatic- substituted at each substitutable position with 0-3 substituents independently selected from J. For example, R¹ and R² are each independently (C1-C12)-aliphatic- substituted at each substitutable position with 0-3 substituents independently selected from J. In one embodiment, R¹ and R² are each independently unsubstituted (C1-C4)-aliphatic groups, such as methyl, ethyl or allyl. In another embodiment, R¹ and R² are each independently (C1-C4)-alkyl, and wherein at least one of R¹ and R² is substituted with at least one (C6-C10)-aryl, such as phenyl. In yet another embodiment, R¹ and R² are each independently (C1-C4)-alkyl, and R¹ and R² are each independently substituted with at least one (C6-C10)-aryl, such as phenyl.

In other embodiments for a compound of Formula I-A, R¹ is H— and R² is (C1-C12)-aliphatic- substituted at each substitutable position with 0-3 substituents independently selected from J. For example, R¹ is H— and R² is unsubstituted (C1-C4)-alkyl, such as methyl or isopropyl. In another embodiment, R¹ is H— and R² is (C1-C12)-aliphatic- that is substituted with at least one (C6-C10)-aryl group, such as where R² is a phenyl-(C1-C4)-alkyl- group.

In another embodiment for a compound of Formula I-A, R¹ and R² taken together with the atom to which they are attached form a C5-C10 aromatic or non-aromatic ring. Examples of these rings include a 5-membered aromatic or non-aromatic ring. For example, R¹ and R² taken together with the atom to which they are attached form a pyrrolidine ring.

In another embodiment, this invention provides a compound that has the Formula I-B:

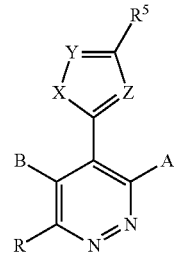

I-B or pharmaceutically acceptable salt thereof;

wherein X, Y and Z are each independently selected from —CR⁴—, —N(R⁴)—, —N=, —O— and —S—,
R⁴ and R⁵ are each independently selected from:
halogen, —OR³, —NO₂, —CN, —CF₃, —OCF₃, —R³, oxo, thioxo, 1,2-methylenedioxy, 1,2-ethylenedioxy, =N(R³), =N(OR³), —N(R³)₂, —SR³, —SOR³, —SO₂R³, —SO₂N(R³)₂, —SO₃R³, —C(O)R³, —C(O)C(O)R³, —C(O)CH₂C(O)R³, —C(S)R³, —C(S)OR³, —C(O)OR³, —C(O)C(O)OR³, —C(O)C(O)N(R³)₂, —OC(O)R³, —C(O)N(R³)₂, —OC(O)N(R³)₂, —C(S)N(R³)₂, —(CH₂)₀₋₂NHC(O)R³, —N(R³)N(R³)COR³, —N(R³)N(R³)C(O)OR³, —N(R³)N(R³)CON(R³)₂, —N(R³)SO₂R³, —N(R³)SO₂N(R³)₂, —N(R³)C(O)OR³, —N(R³)C(O)R³, —N(R³)C(S)R³, —N(R³)C(O)N(R³)₂, —N(R³)C(S)N(R³)₂, —N(COR³)COR³, —N(OR³)R³, —C(=NH)N(R³)₂, —C(O)N(OR³)R³, —C(=NOR³)R³, —OP(O)(OR³)₂, —P(O)(R³)₂, —P(O)(OR³)₂, and —P(O)(H)(OR³); and
the other variables in the Formula are as defined in any of the embodiments herein.

In certain embodiments for a compound of Formula I-B, X is —O—.

In other embodiments for a compound of Formula I-B, Z is —N=. In yet another embodiment for a compound of Formula I-B, X is —O— and Z is —N=.

In yet other embodiments for a compound of Formula I-B, Y is —CR⁴— or —N=. In certain embodiments for a compound of Formula I-B, Y is —CR⁴— and R⁴ is H or (C1-C12)-aliphatic. In one embodiment, Y is —CR⁴— and R⁴ is H. In another embodiment, Y is —CR⁴— and R⁴ is (C1-C4)-alkyl.

In some embodiments for a compound of Formula I-B, X, Y and Z are defined herein and R⁵ is (C1-C12)-aliphatic- or —C(O)OR³. For example, R⁵ is (C1-C4)-alkyl, such as methyl or ethyl. In other embodiments for a compound of Formula I-B, R⁵ is —C(O)OR³, wherein R³ is (C1-C12)aliphatic, such as (C1-C4)-alkyl-. In some embodiments, R⁵ is —C(O)OMe. In certain embodiments for a compound of Formula I-B, X is —O—, Z is —N=, Y is —CR⁴— or —N=, and R⁵ is (C1-C12)-aliphatic- or —C(O)OR³.

In another embodiment, this invention provides a compound that has the Formula I-C:

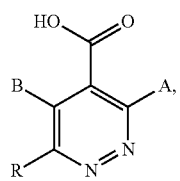

I-C or a pharmaceutically acceptable salt thereof, wherein A, B and R are as defined in any of the embodiments herein.

In another embodiment, this invention provides a compound that has the Formula I-D:

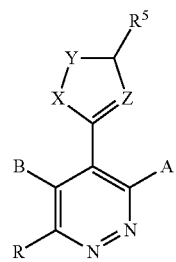

I-D or a pharmaceutically acceptable salt thereof;

wherein:
X, Y and Z are each independently selected from —C(R⁴)₂—, N(R⁴), N, O, and S; and
each of R⁴ and R⁵ are independently selected from:
halogen, —OR³, —NO₂, —CN, —CF₃, —OCF₃, —R³, oxo, thioxo, 1,2-methylenedioxy, 1,2-ethylenedioxy, =N(R³), =N(OR³), —N(R³)₂, —SR³, —SOR³, —SO₂R³, —SO₂N(R³)₂, —SO₃R³, —C(O)R³, —C(O)C(O)R³, —C(O)CH₂C(O)R³, —C(S)R³, —C(S)OR³, —C(O)OR³, —C(O)C(O)OR³, —C(O)C(O)N(R³)₂, —OC(O)R³, —C(O)N(R³)₂, —OC(O)N(R³)₂, —C(S)N(R³)₂, —(CH₂)₀₋₂NHC(O)R³, —N(R³)N(R³)COR³, —N(R³)N(R³)C(O)OR³, —N(R³)N(R³)CON(R³)₂, —N(R³)SO₂R³, —N(R³)SO₂N(R³)₂, —N(R³)C(O)OR³, —N(R³)C(O)R³, —N(R³)C(S)R³, —N(R³)C(O)N(R³)₂, —N(R³)C(S)N(R³)₂, —N(COR³)COR³, —N(OR³)R³, —C(=NH)N(R³)₂, —C(O)N(OR³)R³, —C(=NOR³)R³, —OP(O)(OR³)₂, —P(O)(R³)₂, —P(O)(OR³)₂, and —P(O)(H)(OR³);
and A, B and R are as defined in any of the embodiments herein.

In certain embodiments for a compound of Formula I-D, X is —O—.

In some embodiments for a compound of Formula I-D, Z is —N=. In other embodiments for a compound of Formula I-D, X is —O— and Z is —N=.

In yet other embodiments for a compound of Formula I-D, Y is —C(R⁴)₂. For example, Y is —C(R⁴)₂ and at least one R⁴ is H or (C1-C12)-aliphatic. In other embodiments, Y is —C(R⁴)₂ and each R⁴ is independently H. In another embodiment Y is —C(R⁴)₂, where at least one R⁴ is (C1-C4)-alkyl-.

In some embodiments for a compound of Formula I-D, X, Y and Z are as defined herein, and R⁵ is (C1-C12)-aliphatic- or —C(O)OR³. For example, R⁵ is (C1-C4)-alkyl, such as methyl or ethyl. In some embodiments for a compound of Formula I-D, R⁵ is —C(O)OR³, where R³ is (C1-C12)aliphatic, such as (C1-C4)-alkyl-. In some embodiments, R⁵ is —C(O)OMe. In certain embodiments for a compound of Formula I-D, X is —O—, Z is —N=, Y is —C(R⁴)₂, and R⁵ is (C1-C12)-aliphatic- or —C(O)OR³.

The following description applies to any of the embodiments of Formulae I, I-A, I-B, I-C and I-D described above.

In one aspect, the invention provides a compound, wherein A is (C6-C10)-aryl- or (C5-C10)-heteroaryl-, each of said aryl or heteroaryl being independently substituted with 0-5 substituents independently selected from J. In certain aspects, A is phenyl, substituted with 0-5 substituents independently selected from J. For example, A can be phenyl that is unsubstituted or substituted with at least one halogen or —OR³. In one embodiment, A is phenyl that is substituted with at least one F, Cl, or —OCH₃.

In another embodiment, A is a 5-membered or 6-membered heteroaryl substituted with 0-5 substituents independently selected from J, such as where A is pyrazolyl or pyridyl. Examples of these 5-membered or 6-membered heteroaryl groups are ones that are unsubstituted or substituted with at least one (C1-C12)-aliphatic, such as —CH₃.

In another aspect, the invention provides a compound, wherein B is (C6-C10)-aryl- or (C5-C10)-heteroaryl-, each of said aryl or heteroaryl being independently substituted with 0-5 substituents independently selected from J. In certain aspects, B is phenyl substituted with 0-5 substituents independently selected from J.

The invention also includes combinations of A and B as described above. In some embodiments, B is phenyl substituted with 0-5 substituents independently selected from J, and A is phenyl, pyrazolyl or pyridyl, substituted with 0-3 substituents independently selected from J. These combinations can in turn be combined with any or all of the values of X, Y, Z, R, R¹, R², R³, R⁴ and R⁵ described above.

In certain embodiments, the invention provides a compound of formula I, wherein B is phenyl; A is phenyl, pyrazolyl or pyridyl, substituted with 0-2 substituents independently selected from —OR³ where R³ is (C1-C4)alkyl- (such as —OMe), halogen (such as —Cl and —F), and (C1-C4) alkyl- (such as —Me); R is hydrogen; R' is selected from the group consisting of:
(1) —COOH;
(2) —C(O)NR¹R², wherein
   R¹ and R² are each independently (C1-C4)-aliphatic- (such as methyl, ethyl and allyl),
   or R¹ and R² are each independently (C1-C4)-alkyl (such as methyl), wherein at least one of R¹ and R² is substituted with at least one phenyl,
   or R¹ is H, and R² is (C1-C4)-alkyl (such as methyl and isopropyl),
   or R¹ and R² taken together with the nitrogen atom to which they are bound form a 5-membered non-aromatic ring (such as a pyrrolidine ring); and
(3) a 5-membered heterocyclic or heteroaryl ring having one nitrogen atom and one oxygen atom (such as oxazole or dihydrooxazole); wherein the 5-membered heterocyclic or heteroaryl ring has 0-2 substituents selected independently from (C1-C4)-alkyl- (such as methyl, ethyl and isopropyl) and —C(O)OR³ where R³ is (C1-C4)alkyl- (such as —COOMe).

In some embodiments, the invention provides a compound of formula I, wherein B is phenyl; A is phenyl substituted with 0 or 1 substituent selected from —OR³ where R³ is (C1-C4) alkyl- (such as —OMe) and halogen (such as —Cl); R is hydrogen; R' is selected from the group consisting of:
(1) —COOH;
(2) —C(O)NR¹R², wherein
   R¹ and R² are each independently (C1-C4)-alkyl- (such as methyl),
   or R¹ and R² are each independently (C1-C4)-alkyl (such as methyl), wherein at least one of R¹ and R² is substituted with one phenyl,
   or R¹ is H, and R² is (C1-C4)-alkyl (such as methyl and isopropyl); and
(3) a 5-membered heterocyclic or heteroaryl ring having one nitrogen atom and one oxygen atom (such as oxazole or dihydrooxazole), wherein the 5-membered heterocyclic or heteroaryl ring has 1 substituent selected from (C1-C4)-alkyl- (such as methyl and ethyl) and —C(O)OR³ where R³(C1-C4)alkyl- (such as —COOMe).

Examples of particular compounds of Formulas I, I-A, I-B, I-C and I-D include:

| Compound | Structure |
|---|---|
| 1 | (structure: 4,5-diphenyl pyridazine-4-carboxamide, NHCH) |
| 2 | (structure: 4,5-diphenyl pyridazine-4-carboxamide, NH(i-Pr)) |
| 3 | (structure: 4,5-diphenyl pyridazine-4-carboxamide, NH₂) |
| 4 | (structure: 4,5-diphenyl pyridazine-4-carboxamide, N(CH₃)₂) |
| 5 | (structure: 4,5-diphenyl pyridazine-4-carboxamide, N(CH₂Ph)₂) |
| 6 | (structure: 4,5-diphenyl pyridazine-4-carboxylic acid, OH) |

| Compound | Structure |
|---|---|
| 7 | 4,5-diphenyl-N,N-diethylpyridazine-4-carboxamide (3,4-diphenylpyridazine with N,N-diethylcarboxamide at 4-position) |
| 8 | (3,4-diphenylpyridazin-4-yl)(pyrrolidin-1-yl)methanone |
| 9 | N-benzyl-3,5-diphenylpyridazine-4-carboxamide |
| 10 | 3-(3-chlorophenyl)-5-phenyl-N,N-dimethylpyridazine-4-carboxamide |
| 11 | 3-(3-methoxyphenyl)-5-phenylpyridazine-4-carboxylic acid |
| 12 | 3-(3-methoxyphenyl)-5-phenyl-N,N-dimethylpyridazine-4-carboxamide |
| 13 | 3-(2,4-difluorophenyl)-5-phenylpyridazine-4-carboxylic acid |
| 14 | 3-(2,4-difluorophenyl)-5-phenyl-N,N-dimethylpyridazine-4-carboxamide |
| 15 | 5-phenyl-3-(pyridin-3-yl)pyridazine-4-carboxylic acid |
| 16 | 5-phenyl-3-(pyridin-3-yl)-N,N-dimethylpyridazine-4-carboxamide |

-continued

| Compound | Structure |
|---|---|
| 17 | 3-(1-methyl-1H-pyrazol-4-yl)-5-phenylpyridazine-4-carboxylic acid |
| 18 | 6-methyl-4-(1-methyl-1H-pyrazol-4-yl)-9-phenyl-5H-pyrazolo[3,4-c]pyridazin-5-one (tricyclic fused pyrazolo-pyridazinone) |
| 19 | N,N-diallyl-3,5-diphenylpyridazine-4-carboxamide |
| 20 | 4-(4-methyloxazol-2-yl)-3,5-diphenylpyridazine |
| 21 | 4-(4-methyl-4,5-dihydrooxazol-2-yl)-3,5-diphenylpyridazine |

-continued

| Compound | Structure |
|---|---|
| 22 | 4-(4-ethyloxazol-2-yl)-3,5-diphenylpyridazine |
| 23 | 4-(4-isopropyloxazol-2-yl)-3,5-diphenylpyridazine |
| 24 | 3-(3-methoxyphenyl)-4-(4-methyloxazol-2-yl)-5-phenylpyridazine |
| 25 | methyl 2-(3,5-diphenylpyridazin-4-yl)-4,5-dihydrooxazole-4-carboxylate |
| 26 | methyl 2-(3,5-diphenylpyridazin-4-yl)oxazole-4-carboxylate |

-continued

| Compound | Structure |
|---|---|
| 27 | Methyl 2-[3-(3-chlorophenyl)-5-phenylpyridazin-4-yl]oxazole-4-carboxylate |
| 28 | Methyl 2-[3-(3-methoxyphenyl)-5-phenylpyridazin-4-yl]-4,5-dihydrooxazole-4-carboxylate |
| 29 | Methyl 2-[3-(3-methoxyphenyl)-5-phenylpyridazin-4-yl]oxazole-4-carboxylate |
| 30 | Methyl 2-[5-phenyl-3-(pyridin-3-yl)pyridazin-4-yl]oxazole-4-carboxylate |
| 31 | 3-(3-chlorophenyl)-4-(4-methyloxazol-2-yl)-5-phenylpyridazine |
| 32 | 4-(4-methyloxazol-2-yl)-5-phenyl-3-(pyridin-3-yl)pyridazine |
| 33 | 5-(3-methyl-1,2,4-oxadiazol-5-yl)-3,4-diphenylpyridazine |
| 34 | 5-(3-ethyl-1,2,4-oxadiazol-5-yl)-3,4-diphenylpyridazine |
| 35 | 3-(3-chlorophenyl)-5-(3-methyl-1,2,4-oxadiazol-5-yl)-4-phenylpyridazine |

-continued

| Compound | Structure |
|---|---|
| 36 | (structure: phenyl-pyridazine with oxadiazole-CH3 and pyridin-3-yl substituents), and |
| 37 | (structure: phenyl-pyridazine with COOH and 3-chlorophenyl substituents) |

Those of skill in the art can readily recognize that the present invention allows for various combinations of moiety choices for variables in the generic structures.

Any embodiment given herein is also intended to represent unlabeled forms as well as isotopically labeled forms of the compounds, unless otherwise indicated. Isotopically labeled compounds have structures depicted by the Formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I, respectively. The invention includes various isotopically labeled compounds as defined herein, for example those into which radioactive isotopes, such as $^3$H, $^{13}$C, and $^{14}$C, are present. Such isotopically labeled compounds are useful in metabolic studies (preferably with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Any of the individual embodiments recited above, including those embodiments defining compounds 1-37, may define Formula I individually or be combined to produce a preferred embodiment of this invention.

In another embodiment, the present invention provides a pharmaceutical composition comprising a pharmaceutically acceptable carrier and a compound of Formulas I, I-A, I-B, I-C or I-D or pharmaceutically acceptable salt form thereof.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

(3) General Synthetic Methodology

The compounds of this invention may be prepared in general by methods known to those skilled in the art. Schemes 1-9 below illustrate synthetic routes to the compounds of the present invention. Other equivalent schemes, which will be readily apparent to the ordinary skilled organic chemist, may alternatively be used to synthesize various portions of the molecules as illustrated by the general schemes below.

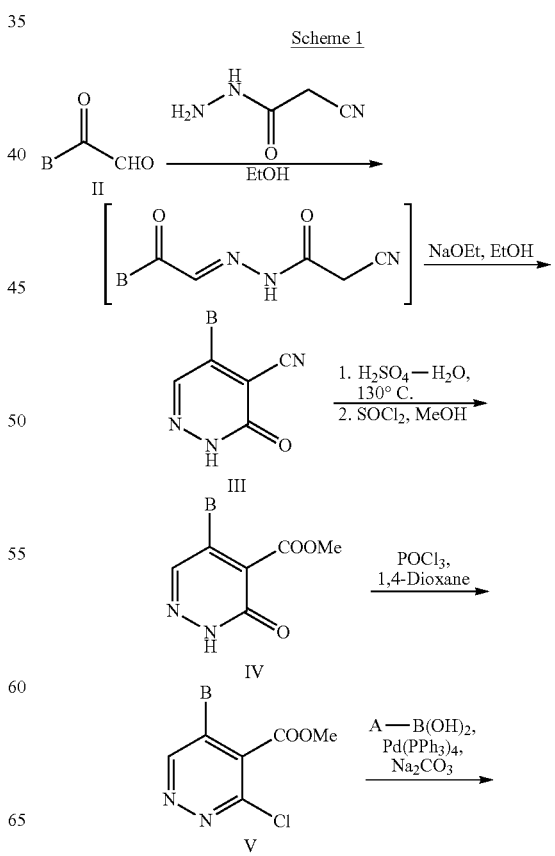

Scheme 1

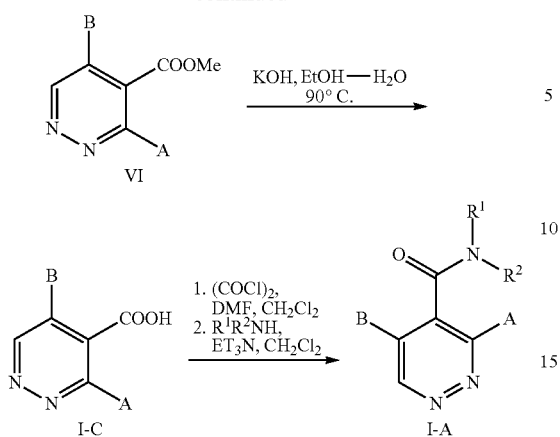

Scheme 1 above provides a general synthetic route for the preparation of compounds of Formula I-A and compounds of Formula I-C.

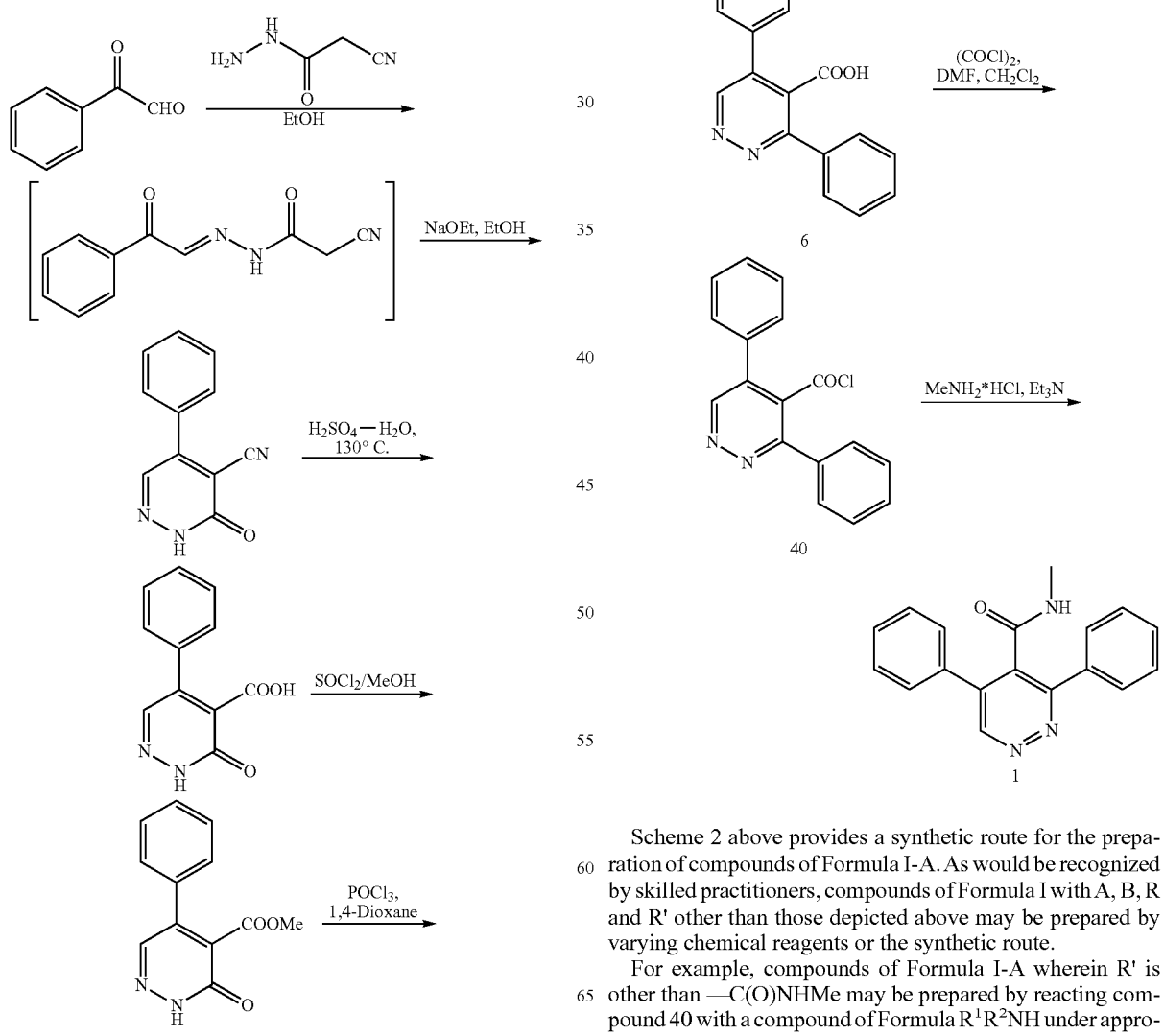

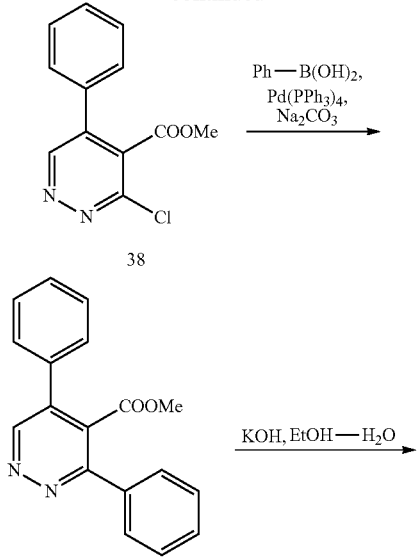

Scheme 2 above provides a synthetic route for the preparation of compounds of Formula I-A. As would be recognized by skilled practitioners, compounds of Formula I with A, B, R and R' other than those depicted above may be prepared by varying chemical reagents or the synthetic route.

For example, compounds of Formula I-A wherein R' is other than —C(O)NHMe may be prepared by reacting compound 40 with a compound of Formula $R^1R^2NH$ under appropriate basic conditions, as shown in Scheme 3.

Scheme 3

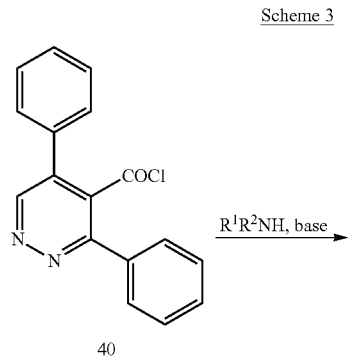

Similarly, compounds of Formula I-A wherein A is other than phenyl and R' is other than —C(O)NHMe may be prepared by reacting compound 38 with a boron reagent of formula A-B(Y)$_n$, wherein Y$_n$ is —(OH)$_2$, —(O-alkyl)$_2$, —F$_3$ or -(alkyl)$_2$, under appropriate Suzuki coupling reactions, as shown in Schemes 4.

Scheme 4

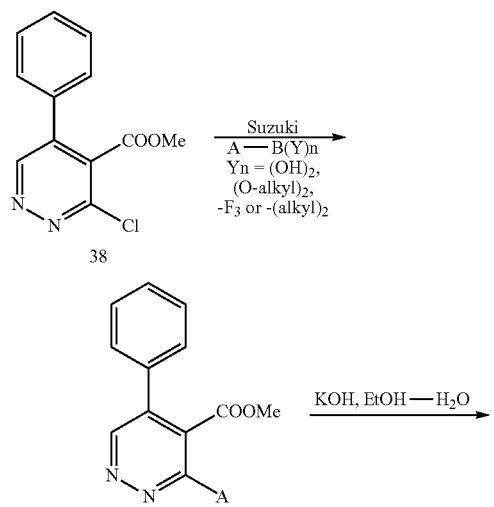

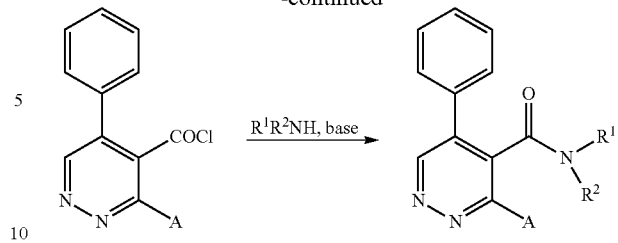

Scheme 5 below provides a general synthetic route for the preparation of compounds of Formula I-B and compounds of Formula I-D. As would be recognized by skilled practitioners, compounds of Formula I-B or Formula I-D with X, Y and Z, other than those depicted in Scheme 5, may be prepared by varying chemical reagents or the synthetic route.

Scheme 5

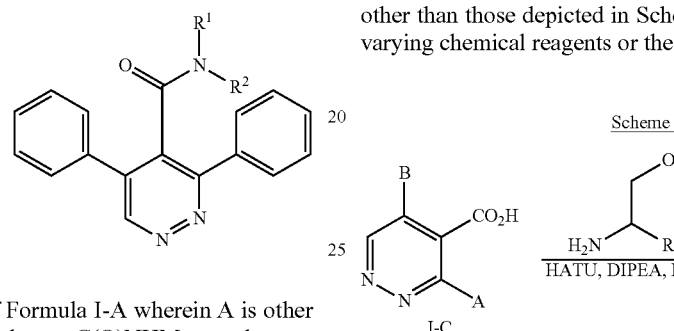

Scheme 6 below provides a synthetic route for the preparation of compounds of Formula I-D. As would be recognized by skilled practitioners, compounds of Formula I-D with R$^5$ other than those depicted above in Scheme 6 may be prepared by varying chemical reagents or the synthetic route.

Scheme 6

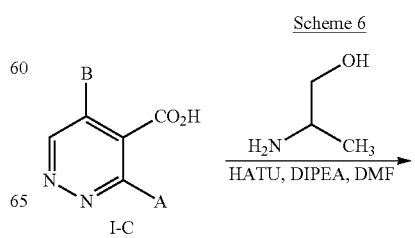

-continued

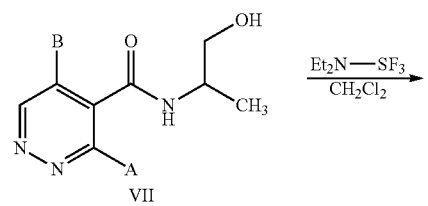

VII

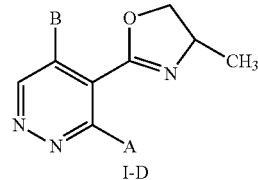

I-D (R is H, X is —O—, Z is —N=,
Y is —CH₂— and R⁵ is Me—)

Scheme 7

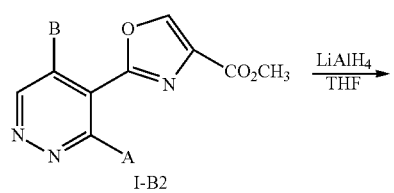

I-B2

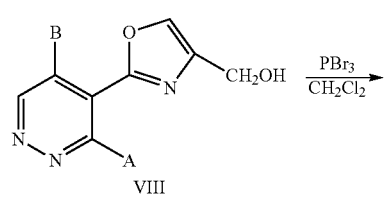

VIII

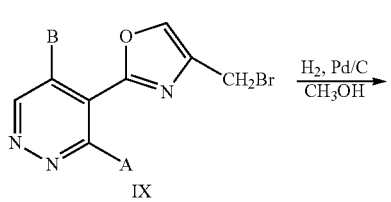

IX

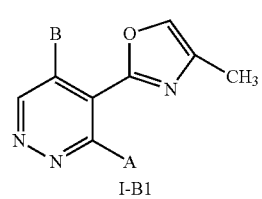

I-B1

Scheme 7 above provides a synthetic route for the preparation of compounds of Formula I-B1 (e.g., compounds of Formula I-B, wherein R is H, X is —O—, Z is —N=, Y is —CH=, and R⁵ is methyl), using a compound of Formula I-B2 (e.g., a compound of Formula I-B, wherein R is H, X is —O—, Z is —N=, Y is —CH=, and R⁵ is —COOMe) as the starting material.

Scheme 8

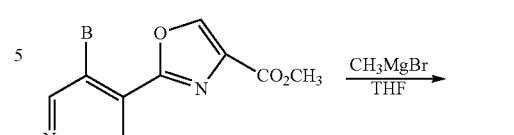

I-B2

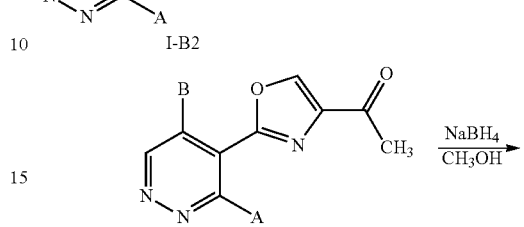

X

XI

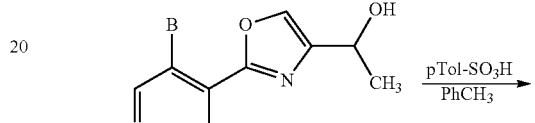

XII

I-B3

Scheme 8 above provides a synthetic route for the preparation of compounds of Formula I-B3 (e.g., compounds of Formula I-B, wherein R is H, X is —O—, Z is —N=, Y is —CH=, and R⁵ is ethyl), using the compound of Formula I-B2 as the starting material.

Scheme 9

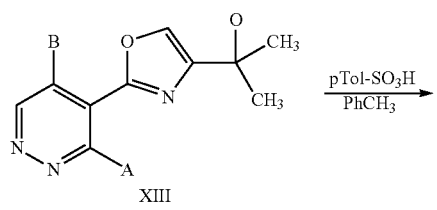

I-B2

XIII

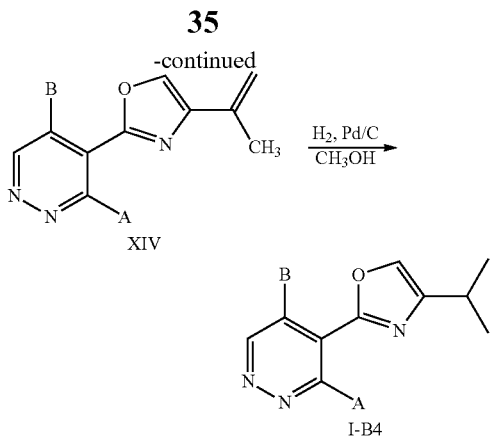

Scheme 9 above provides a synthetic route for the preparation of compounds of Formula I-B4 (e.g., compounds of Formula I-B, wherein R is H, X is —O—, Z is —N═, Y is —CH═, and $R^5$ is iso-propyl), using the compound of Formula I-B2 as the starting material. As would be recognized by skilled practitioners, compounds of Formula I-B with X, Y, Z and $R^5$ other than those depicted above in Schemes 7-9 may be prepared by varying chemical reagents or the synthetic route.

(4) Methods of Assessing Cognitive Impairment

Animal models serve as an important resource for developing and evaluating treatments for CNS disorders with cognitive impairment. Features that characterize cognitive impairment in animal models typically extend to cognitive impairment in humans. Efficacy in such animal models is, thus, expected to be predictive of efficacy in humans. The extent of cognitive impairment in an animal model for a CNS disorder, and the efficacy of a method of treatment for said CNS disorder may be tested and confirmed with the use of a variety of cognitive tests.

A Radial Arm Maze (RAM) behavioral task is one example of a cognitive test, specifically testing spacial memory (Chappell et al. *Neuropharmacology* 37: 481-487, 1998). The RAM apparatus consists of, e.g., eight equidistantly spaced arms. A maze arm projects from each facet of a center platform. A food well is located at the distal end of each arm. Food is used as a reward. Blocks can be positioned to prevent entry to any arm. Numerous extra maze cues surrounding the apparatus may also be provided. After habituation and training phases, spatial memory of the subjects may be tested in the RAM under control or test compound-treated conditions. As a part of the test, subjects are pretreated before trials with a vehicle control or one of a range of dosages of the test compound. At the beginning of each trial, a subset of the arms of the eight-arm maze is blocked. Subjects are allowed to obtain food on the unblocked arms to which access is permitted during this initial "information phase" of the trial. Subjects are then removed from the maze for a delay period, e.g., a 60 second delay, a 15 minute delay, a one-hour delay, a two-hour delay, a six hour delay, a 24 hour delay, or longer) between the information phase and the subsequent "retention test," during which the barriers on the maze are removed, thus allowing access to all eight arms. After the delay period, subjects are placed back onto the center platform (with the barriers to the previously blocked arms removed) and allowed to obtain the remaining food rewards during this retention test phase of the trial. The identity and configuration of the blocked arms vary across trials. The number of "errors" the subjects make during the retention test phase is tracked. An error occurs in the trial if the subjects entered an arm from which food had already been retrieved in the pre-delay component of the trial, or if it re-visits an arm in the post-delay session that had already been visited. A fewer number of errors would indicate better spatial memory. The number of errors made by the test subject, under various test compound treatment regimes, can then be compared for efficacy of the test compound in treating a CNS disorder with cognitive impairment.

Another cognitive test that may be used to assess the effects of a test compound on the cognitive impairment of a CNS disorder model animal is the Morris water maze. A water maze is a pool surrounded with a novel set of patterns relative to the maze. The training protocol for the water maze may be based on a modified water maze task that has been shown to be hippocampal-dependent (de Hoz et al., *Eur. J. Neurosci.*, 22:745-54, 2005; Steele and Morris, *Hippocampus* 9:118-36, 1999). The subject is trained to locate a submerged escape platform hidden underneath the surface of the pool. During the training trial, a subject is released in the maze (pool) from random starting positions around the perimeter of the pool. The starting position varies from trial to trial. If the subject does not locate the escape platform within a set time, the experimenter guides and places the subject on the platform to "teach" the location of the platform. After a delay period following the last training trial, a retention test in the absence of the escape platform is given to assess spatial memory. The subject's level of preference for the location of the (now absent) escape platform, as measured by, e.g., the time spent in that location or the number of crossings of that location made by the mouse, indicates better spatial memory, i.e., treatment of cognitive impairment. The preference for the location of the escape platform under different treatment conditions, can then be compared for efficacy of the test compound in treating a CNS disorder with cognitive impairment.

(5) Age-Related Cognitive Impairment

This invention provides methods and compositions for treating age-related cognitive impairment or the risk thereof using a α5-containing $GABA_A$ R agonist and analogs, derivatives, and pharmaceutically acceptable salts and solvates thereof. In certain embodiments, treatment comprises alleviation, amelioration or slowing the progression, of one or more symptoms associated with age-related cognitive impairment. In certain embodiments, treatment of age-related cognitive impairment comprises slowing the conversion of age-related cognitive impairment (including, but not limited to MCI, ARCD and AAMI) into dementia (e.g., AD). The methods and compositions may be used for human patients in clinical applications in the treating age-related cognitive impairment in conditions such as MCI, ARCD and AAMI or for the risk thereof. The dose of the composition and dosage interval for the method is, as described herein, one that is safe and efficacious in those applications.

In some embodiments, a subject to be treated by the methods and compositions of this invention exhibits age-related cognitive impairment or is at risk of such impairment. In some embodiments, the age-related cognitive impairment includes, without limitation, Age-Associated Memory Impairment (AAMI), Mild Cognitive Impairment (MCI) and Age-related Cognitive Decline (ARCD).

Animal models serve as an important resource for developing and evaluating treatments for such age-related cognitive impairments. Features that characterize age-related cognitive impairment in animal models typically extend to age-related cognitive impairment in humans. Efficacy in such animal models is, thus, expected to be predictive of efficacy in humans.

Various animal models of age-related cognitive impairment are known in the art. For example, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Gallagher et al. *Behav. Neurosci.* 107:618-626, (1993); Rapp and Gallagher, *Proc. Natl. Acad. Sci.* 93: 9926-9930, (1996); Nicolle et al., *Neuroscience* 74: 741-756, (1996); Nicolle et al., *J. Neurosci.* 19: 9604-9610, (1999); International Patent Publication WO2007/019312 and International Patent Publication WO 2004/048551. Such an animal model of age-related cognitive impairment may be used to assay the effectiveness of the methods and compositions this invention in treating age-related cognitive impairment.

The efficacy of the methods and compositions of this invention in treating age-related cognitive impairment may be assessed using a variety of cognitive tests, including the Morris water maze and the radial arm maze, as discussed above.

(6) Dementia

This invention also provides methods and compositions for treating dementia using a α5-containing $GABA_A$ R agonist and analogs, derivatives, and pharmaceutically acceptable salts and solvates thereof. In certain embodiments, treatment comprises alleviation, amelioration, or slowing the progression of one or more symptoms associated with dementia. In certain embodiments, the symptom to be treated is cognitive impairment. In certain embodiments, the dementia is Alzheimer's disease (AD), vascular dementia, dementia with Lewy bodies, or frontotemporal dementia. The methods and compositions may be used for human patients in clinical applications in treating dementia. The dose of the composition and dosage interval for the method is, as described herein, one that is safe and efficacious in those applications.

Animal models serve as an important resource for developing and evaluating treatments for dementia. Features that characterize dementia in animal models typically extend to dementia in humans. Thus, efficacy in such animal models is expected to be predictive of efficacy in humans. Various animal models of dementia are known in the art, such as the PDAPP, Tg2576, APP23, TgCRND8, J20, hPS2 Tg, and APP+PS1 transgenic mice. Sankaranarayanan, *Curr. Top. Medicinal Chem.* 6: 609-627, 2006; Kobayashi et al. *Genes Brain Behav.* 4: 173-196. 2005; Ashe and Zahns, *Neuron.* 66: 631-45, 2010. Such animal models of dementia may be used to assay the effectiveness of the methods and compositions of this invention of the invention in treating dementia.

The efficacy of the methods and compositions of this invention in treating dementia, or cognitive impairment associated with dementia, may be assessed in animals models of dementia using a variety of cognitive tests known in the art, including the Morris water maze and the radial arm maze, as discussed above.

(7) Post Traumatic Stress Disorder

This invention also provides methods and compositions for treating post traumatic stress disorder (PTSD) using a α5-containing $GABA_A$ R agonist and analogs, derivatives, and pharmaceutically acceptable salts and solvates thereof. In certain embodiments, treatment comprises alleviation, amelioration, or slowing the progression of one or more symptoms associated with PTSD. In certain embodiments, the symptom to be treated is cognitive impairment. The methods and compositions may be used for human patients in clinical applications in treating PTSD. The dose of the composition and dosage interval for the method is, as described herein, one that is safe and efficacious in those applications.

Patients with PTSD (and, to a lesser degree trauma-exposed patients without PTSD) have smaller hippocampal volumes (Woon et al., *Prog. Neuro-Psychopharm.* & Biological Psych. 34, 1181-1188; Wang et al., *Arch. Gen. Psychiatry* 67:296-303, 2010). PTSD is also associated with impaired cognitive performance. Older individuals with PTSD have greater declines in cognitive performance relative to control patients (Yehuda et al., *Bio. Psych.* 60: 714-721, 2006) and have a greater likelihood of developing dementia (Yaffe et al., *Arch. Gen. Psych.* 678: 608-613, 2010).

Animal models serve as an important resource for developing and evaluating treatments for PTSD. Features that characterize PTSD in animal models typically extend to PTSD in humans. Thus, efficacy in such animal models is expected to be predictive of efficacy in humans. Various animal models of PTSD are known in the art.

One rat model of PTSD is Time-dependent sensitization (TDS). TDS involves exposure of the animal to a severely stressful event followed by a situational reminder of the prior stress. The following is an example of TDS. Rats are placed in a restrainer, then placed in a swim tank and made to swim for a period of time, e.g., 20 min. Following this, each rat is then immediately exposed to a gaseous anesthetic until loss of consciousness, and finally dried. The animals are left undisturbed for a number of days, e.g., one week. The rats are then exposed to a "restress" session consisting of an initial stressor, e.g., a swimming session in the swim tank (Liberzon et al., *Psychoneuroendocrinology* 22: 443-453, 1997; Harvery et al., *Psychopharmacology* 175:494-502, 2004). TDS results in an enhancement of the acoustic startle response (ASR) in the rat, which is comparable to the exaggerated acoustic startle that is a prominent symptom of PTSD (Khan and Liberzon, Psychopharmacology 172: 225-229, 2004). Such animal models of PTSD may be used to assay the effectiveness of the methods and compositions of this invention of the invention in treating PTSD.

The efficacy of the methods and compositions of this invention in treating PTSD, or cognitive impairment associated with PTSD, may also be assessed in animals models of PTSD using a variety of other cognitive tests known in the art, including the Morris water maze and the radial arm maze, as discussed above.

(8) Schizophrenia

This invention additionally provides methods and compositions for treating schizophrenia using a α5-containing $GABA_A$ R agonist and analogs, derivatives, and pharmaceutically acceptable salts and solvates thereof. In certain embodiments, treatment comprises alleviation, amelioration or slowing the progression, of one or more symptoms associated with schizophrenia. In certain embodiments, the symptom to be treated is cognitive impairment. The methods and compositions may be used for human patients in clinical applications in treating schizophrenia. The dose of the composition and dosage interval for the method is, as described herein, one that is safe and efficacious in those applications.

Animal and human studies demonstrate that GABA signaling is reduced in schizophrenia, for examples in various areas of the cerebral cortex and hippocampus. See, e.g., Akbarian et al., Arch. Gen. Psychiatry 52:258-266, 1995; Volk et al., Arch. Gen. Psychiatry 57:237-245, 2000; Hashimoto et al., J. Neurosci. 23:6315-6326, 2003; Hashimoto et al., Mol. Psychiatry. 13:147-161.2008; Lodge et al., J. Neurosci., 29:2344-2354, 2009; Yoon et al., J. Neurosci. 30: 3777-81, 2010. Cognitive impairments are also associated with schizophrenia. They precede the onset of psychosis and are present in non-affected relatives. The cognitive impairments associated with schizophrenia constitute a good predictor for functional outcome and are a core feature of the disorder. Cognitive features in schizophrenia reflect dysfunction in frontal cortical and hippocampal circuits. Patients with schizophrenia also present hippocampal pathologies such as reductions in hippocampal volume, reductions in neuronal size and dysfunctional hyperactivity. An imbalance in excitation and inhibition in these brain regions has also been documented in schizophrenic patients suggesting that drugs targeting inhibitory mechanisms could be therapeutic. See, e.g., Guidotti et al., Psychopharmacology 180: 191-205, 2005; Zierhut, Psych. Res. Neuroimag. 183:187-194, 2010; Wood et al., NeuroImage 52:62-63, 2010; Vinkers et al., Expert Opin. Investig. Drugs 19:1217-1233, 2009; Young et al., Pharmacol. Ther. 122:150-202, 2009. In particular, compounds that selectively and positively modulate the action of $GABA_A$ receptors comprising α5 subunits have been proposed as therapeutic agents that will contribute to the anxiolytic, antipanic and anticonvulsant actions without producing sedation, amnesia, or tolerance (Guidotti et al., Psychopharmacology 180: 191-205, 2005).

Animal models serve as an important resource for developing and evaluating treatments for schizophrenia. Features that characterize schizophrenia in animal models typically extend to schizophrenia in humans. Thus, efficacy in such animal models is expected to be predictive of efficacy in humans. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., PNAS, 99: 17095-17100, 2002). Another animal model of schizophrenia is methylaoxymethanol acetate (MAM)-treatment in rats. Pregnant female rats are administered MAM (20 mg/kg, intraperitoneal) on gestational day 17. MAM-treatment recapitulate a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning. (see Lodge et al., J. Neurosci., 29:2344-2354, 2009) Such animal models of schizophrenia may be used to assay the effectiveness of the methods and compositions of the invention in treating schizophrenia.

The efficacy of the methods and compositions of this invention in treating schizophrenia, or cognitive impairment associated with schizophrenia, may also be assessed in animal models of schizophrenia using a variety of other cognitive tests known in the art, including the Morris water maze and the radial arm maze, as discussed above.

(9) Cancer Therapy-Related Cognitive Impairment

This invention additionally provides methods and compositions for treating cancer therapy-related cognitive impairment using a α5-containing $GABA_A$ R agonist and analogs, derivatives, and pharmaceutically acceptable salts and solvates thereof. In certain embodiments, treatment comprises alleviation, amelioration or slowing the progression, of one or more symptoms associated with cancer therapy-related cognitive impairment. The methods and compositions may be used for human patients in clinical applications in treating cancer therapy-related cognitive impairment. The dose of the composition and dosage interval for the method is, as described herein, one that is safe and efficacious in those applications.

Therapies that are used in cancer treatment, including chemotherapy, radiation, or combinations thereof, can cause cognitive impairment in patients, in such functions as memory, learning, and attention. Cytotoxicity and other adverse side-effects on the brain of cancer therapies are the basis for this form of cognitive impairment, which can persist for decades. (Dietrich et al., Oncologist 13:1285-95, 2008; Soussain et al., Lancet 374:1639-51, 2009).

Cognitive impairment following cancer therapies reflects dysfunction in frontal cortical and hippocampal circuits that are essential for normal cognition. In animal models, exposure to either chemotherapy or radiation adversely affects performance on tests of cognition specifically dependent on these brain systems, especially the hippocampus (Kim et al., J. Radiat. Res. 49:517-526, 2008; Yang et al., Neurobiol. Learning and Mem. 93:487-494, 2010). Thus, drugs targeting these cortical and hippocampal systems could be neuroprotective in patients receiving cancer therapies and efficacious in treating symptoms of cognitive impairment that may last beyond the interventions used as cancer therapies.

Animal models serve as an important resource for developing and evaluating treatments for cancer therapy-related cognitive impairment. Features that characterize cancer therapy-related cognitive impairment in animal models typically extend to cancer therapy-related cognitive impairment in humans. Thus, efficacy in such animal models is expected to be predictive of efficacy in humans. Various animal models of cancer therapy-related cognitive impairment are known in the art.

Examples of animal models of cancer therapy-related cognitive impairment include treating animals with anti-neoplastic agents such as cyclophosphamide (CYP) or with radiation, e.g., $^{60}$Co gamma-rays. (Kim et al., J. Radiat. Res. 49:517-526, 2008; Yang et al., Neurobiol. Learning and Mem. 93:487-494, 2010). The cognitive function of animal models of cancer therapy-related cognitive impairment may be tested with cognitive tests to assay the effectiveness of the methods and compositions of the invention in treating cancer therapy-related cognitive impairment. The efficacy of the methods and compositions of this invention in treating cancer therapy-related cognitive impairment may also be assessed using a variety of cognitive tests known in the art, including the Morris water maze and the radial arm maze, as discussed above.

(10) Research Domain Criteria (RDoC)

This invention further provides methods and compositions for treating impairment in neurological disorders and neuropsychiatric conditions using a α5-containing $GABA_A$ R agonists and analogs, derivatives, and pharmaceutically acceptable salts and solvates thereof. In certain embodiments, treatment comprises alleviation, amelioration or slowing the progression, of one or more symptoms associated with such impairment.

Research Domain Criteria (RDoC) are expected to augment clinical criteria, such as DSM and ICD, for diagnosis of disease and disorders affecting the nervous system (see, e.g., Am. J. Psychiatry 167:7 (2010)). The RDoC is intended to provide classification based on discoveries in genomics and neuroscience as well as clinical observation. The high expression of α5-containing $GABA_A$ receptors in specific neural circuits in the nervous system could be therapeutic targets for neural circuit dysfunction identified under RDoC.

(11) Assays for $GABA_A$ α5 Subunit Binding and Receptor Agonist Activity

The affinity of test compounds for a $GABA_A$ receptor comprising the $GABA_A$ α5 subunit may be determined using receptor binding assays that are known in the art. See, e.g., U.S. Pat. Nos. 7,642,267 and 6,743,789, which are incorporated herein by reference.

The activity of the test compounds as a α5-containing $GABA_A$ R agonist may be tested by electrophysiological methods known in the art. See, e.g., U.S. Pat. No. 7,642,267 and Guidotti et al., Psychopharmacology 180: 191-205, 2005. Agonist activity may be tested, for examples, by assaying GABA-induced chloride ion conductance of $GABA_A$ receptors comprising the $GABA_A$ α5 subunit. Cells expressing such receptors may be exposed to an effective amount of a compound of the invention. Such cells may be contacted in vivo with compounds of the invention through contact with a body fluid containing the compound, for example through contact with cerebrospinal fluid. In vitro tests may be done by contacting cells with a compound of the invention in the presence of GABA. Increased GABA-induced chloride conductance in cells expressing $GABA_A$ receptors comprising the $GABA_A$ α5 subunit in the presence of the test compound would indicate agonist activity of said compound. Such changes in conductance may be detected by, e.g., using a voltage-clamp assay performed on Xenopus oocytes injected with $GABA_A$ receptor subunit mRNA (including $GABA_A$ α5 subunit RNA), HEK 293 cells transfected with plasmids encoding $GABA_A$ receptor subunits, or in vivo, ex vivo, or cultured neurons.

(12) Compositions and Modes of Administration

It will be appreciated that compounds and agents used in the compositions and methods of the present invention preferably should readily penetrate the blood-brain barrier when peripherally administered. Compounds which cannot penetrate the blood-brain barrier, however, can still be effectively administered directly into the central nervous system, e.g., by an intraventricular route.

In some embodiments of this invention, the α5-containing $GABA_A$ R agonist is Formulated with a pharmaceutically acceptable carrier. In other embodiments, no carrier is used. For example, the α5-containing $GABA_A$ R agonist can be administered alone or as a component of a pharmaceutical Formulation (therapeutic composition). The α5-containing $GABA_A$ R agonist may be formulated for administration in any convenient way for use in human medicine.

In some embodiments, the therapeutic methods of the invention include administering the composition of a compound or agent topically, systemically, or locally. For example, therapeutic compositions of compounds or agents of the invention may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds or agents described herein may be formulated as part of an implant or device, or formulated for slow or extended release. When administered parenterally, the therapeutic composition of compounds or agents for use in this invention is preferably in a pyrogen-free, physiologically acceptable form. Techniques and formulations generally may be found in Remington's Pharmaceutical Sciences, Meade Publishing Co., Easton, Pa.

In certain embodiments, pharmaceutical compositions suitable for parenteral administration may comprise the α5-containing $GABA_A$ R agonist in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a α5-containing $GABA_A$ R agonist may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the invention, compositions comprising a α5-containing $GABA_A$ R agonist can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the α5-containing $GABA_A$ R agonist as an active ingredient.

In solid dosage forms for oral administration (capsules, tablets, pills, dragees, powders, granules, and the like), one or more compositions comprising the α5-containing $GABA_A$ R agonist may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the α5-containing $GABA_A$ R agonist, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

As described above, the compounds, agents, and compositions thereof may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," or "slow release," as these terms are used in the pharmaceutical sciences. In some embodiments, the extended release dosage is administered in the form of a patch or a pump.

A person of ordinary skill in the art, such as a physician, is readily able to determine the required amount of α5-containing $GABA_A$ R agonist (s) to treat the subject using the compositions and methods of this invention. It is understood that the dosage regimen will be determined for an individual, taking into consideration, for example, various factors that modify the action of α5-containing $GABA_A$ R agonist, the severity or stage of the disease, route of administration, and characteristics unique to the individual, such as age, weight, size, and extent of cognitive impairment.

It is well-known in the art that normalization to body surface area is an appropriate method for extrapolating doses between species. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33}$ In certain embodiments of the invention, the dose of the α5-containing $GABA_A$ R agonist is between 0.0001 and 100 mg/kg/day (which, given a typical human subject of 70 kg, is between 0.007 and 7000 mg/day).

In certain embodiments of the invention, the interval of administration is 12 or 24 hours. Administration at less frequent intervals, such as once every 6 hours, may also be used.

If administered by an implant, a device or a slow or extended release formulation, the α5-containing $GABA_A$ R agonist can be administered one time, or one or more times periodically throughout the lifetime of the patient as necessary. Other administration intervals intermediate to or shorter than these dosage intervals for clinical applications may also be used and may be determined by one skilled in the art following the methods of this invention.

Desired time of administration can be determined by routine experimentation by one skilled in the art. For example, the α5-containing $GABA_A$ R agonist may be administered for a period of 1-4 weeks, 1-3 months, 3-6 months, 6-12 months, 1-2 years, or more, up to the lifetime of the patient.

In addition to α5-containing $GABA_A$ R agonist, the compositions and methods of this invention can also include other therapeutically useful agents. These other therapeutically useful agents may be administered in a single formulation, simultaneously or sequentially with the α5-containing $GABA_A$ R agonist according to the methods of the invention.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This invention will be better understood from the Experimental Details which follow. However, one skilled in the art will readily appreciate that the specific methods and results discussed are merely illustrative of the invention as described more fully in the embodiments which follow thereafter.

EXAMPLES

Example 1

Synthesis of Compound 1

Compound 1 was prepared according to synthetic Scheme 1. The syntheses of the intermediates and the final product are detailed as follows.

(A) 3-oxo-5-phenyl-2,3-dihydropyridazine-4-carbonitrile

To a solution of phenyl glyoxal (1 g, 7.46 mmol) in ethanol (50 mL), cyanoacetohydrazide (738 mg, 7.46 mmol) was added under nitrogen atmosphere and stirred at room temperature ("rt") for 24 h. After complete consumption of starting materials (by TLC), the reaction mixture was filtered and washed with EtOAc (25 mL×3). The solvent was evaporated under reduced pressure to obtain crude product as a brown solid which was taken forward for next step without further purification.

Sodium metal (342 mg, 14.86 mmol) was added to absolute ethanol (100 mL) at 0° C. under argon atmosphere. After complete consumption of sodium metal, a solution of product from the previous step (37.28 mmol) in ethanol (100 mL) was added drop wise to the alkoxide solution at 0° C. and then refluxed for 4 h. The reaction mixture was cooled and solvent was evaporated under reduced pressure. The residue was dissolved in 25 mL of water and pH was adjusted to 5 using 6N HCl (25 mL). The precipitated solid was isolated by filtration. The crude product was purified by column chromatography (100-200 mesh silica gel, 5% MeOH in $CH_2Cl_2$) to furnish 3-oxo-5-phenyl-2,3-dihydropyridazine-4-carbonitrile (380 mg, 26%) as an ash color solid.

TLC system: 50% EtOAc-hexane
Rf-value: 0.6
Visualization: UV
Mass $(M-H)^+$: 196
$^1$H-NMR ($\delta$, DMSO-$d_6$, 400 MHz): 7.6 (m, 3H), 7.75 (m, 2H), 8.25 (s, 1H), 13.9 (bs, 1H).

(B) Methyl 3-oxo-5-phenyl-2,3-dihydropyridazine-4-carboxylate

The solution of 3-oxo-5-phenyl-2,3-dihydropyridazine-4-carbonitrile (4.5 g, 22.84 mmol) in 60% aqueous $H_2SO_4$ (45 mL) was heated to 150° C. for 24 h. After the completion of the starting material, the reaction mixture was cooled to rt, quenched with ice cold water and extracted with $CH_2Cl_2$ (250 mL×5), washed with brine (50 mL×1) and dried over anhydrous $Na_2SO_4$. The combined organic extracts were evaporated under reduced pressure to furnish 3-oxo-5-phenyl-2,3-dihydropyridazine-4-carboxylic acid (2.5 g, 48%) as a pale yellow solid.

TLC system: 10% MeOH—$CH_2Cl_2$
Rf-value: 0.2
Visualization: UV
Mass $(M+H)^+$: 217

A solution of 3-oxo-5-phenyl-2,3-dihydropyridazine-4-carboxylic acid (500 mg, 2.31 mmol) in methanol (25 mL) at 0° C., thionyl chloride (5 mL, 40 mmol) was added drop wise and refluxed for 12 h at 80° C. After completion of starting material, the volatiles were removed under reduced pressure to obtain crude product which was extracted with ethyl acetate (100 mL×3), washed with brine (50 mL) and dried over anhydrous $Na_2SO_4$ to furnish 3-oxo-5-phenyl-2,3-dihydropyridazine-4-carboxylate (450 mg) as a light yellow solid which was carried to the next step without further purification.

TLC system: 5% MeOH-DCM
Rf-value: 0.7
Visualization: UV
Mass $(M+H)^+$: 231

(C) Methyl 3-chloro-5-phenylpyridazine-4-carboxylate

A solution of 3-oxo-5-phenyl-2,3-dihydropyridazine-4-carboxylate (450 mg, 1.95 mmol) in $POCl_3$ (5 mL, 60 mmol) was heated to 100° C. for 3 h. After the completion of starting material, the volatiles were removed under reduced pressure. The reaction mixture was quenched with ice cold water (10 mL), extracted with ethyl acetate (50 mL×3), washed with water (10 mL×1), $NaHCO_3$ (15 mL×1), brine solution (25 mL×1) and dried over anhydrous $Na_2SO_4$. The combined organic extracts were evaporated under reduced pressure to obtain the crude product which was purified by column chromatography (100-200 mesh silica gel, 15% EtOAc in hexane) to furnish methyl 3-chloro-5-phenylpyridazine-4-carboxylate (300 mg, 62%) as a pale yellow solid.

TLC system: 30% EtOAc-Hexane
Rf-value: 0.8
Visualization: UV
Mass $(M+H)^+$: 249
$^1$H-NMR ($\delta$, $CDCl_3$, 400 MHz): 3.82, (s, 3H), 7.45 (m, 2H), 7.55 (m, 3H), 9.25 (s, 1H).

(D) Methyl 3,5-diphenylpyridazine-4-carboxylate

A solution of methyl 3-chloro-5-phenylpyridazine-4-carboxylate (300 mg, 1.20 mmol) in 1,4-dioxane (15 mL), distilled water (5 mL), sodium carbonate (256 mg, 2.41 mmol) and phenyl boronic acid (1.91 g, 1.57 mmol) were added and the reaction mixture was degassed for 10 min, followed by addition of tetrakis(triphenylphosphine) palladium (139 mg, 0.12 mmol) and refluxed at 100° C. for 12 h under argon atmosphere. After the completion of starting materials, the reaction mixture was cooled to rt and filtered through a celite pad to remove the solid impurities. The filtrate was diluted with ethyl acetate (40 mL), washed with aq $NaHCO_3$ (5 mL×1), brine solution (5 mL×1) and dried over anhydrous $Na_2SO_4$. The organic extracts were evaporated under reduced pressure to obtain the crude product which was purified by column chromatography (100-200 mesh silica gel, 5% EtOAc in hexane) to furnish methyl 3,5-diphenylpyridazine-4-carboxylate (300 mg, 82%) as a white solid.

TLC system: 30% EtOAc-Hexane
Rf-value: 0.5
Visualization: UV
Mass $(M+H)^+$: 291
HPLC: 93.7%
$^1$H-NMR ($\delta$, $CDCl_3$, 400 MHz): 3.58, (s, 3H), 7.4-7.6 (m, 8H), 7.7 (m, 2H), 9.28 (s, 1H).

(E) Methyl 3,5-diphenylpyridazine-4-carboxylic acid (compound 6)

To a solution of methyl 3,5-diphenylpyridazine-4-carboxylate (300 mg, 1.03 mmol) in 1:1 MeOH:$H_2O$ (10 mL), KOH (576 mg, 10.28 mmol) was added and refluxed at 100° C. for 12 h. After the completion of starting material, the reaction mixture was diluted with water (5 mL×1) and washed with ethyl acetate (5 mL×1). The aqueous layer was acidified with 6N HCl (5 mL) solution, solid precipitated out. The solid was filtered and dried to furnish methyl 3, 5-diphenylpyridazine-4-carboxylic acid (compound 6) (275 mg, 96%) as a white solid.

TLC system: 5% MeOH-DCM
Rf-value: 0.2
Visualization: UV
Mass $(M+H)^+$: 277.2
HPLC: 98.09%

(F) N-methyl-3,5-diphenylpyridazine-4-carboxamide (compound 1)

To a solution of methyl 3,5-diphenylpyridazine-4-carboxylic acid (compound 6) (200 mg, 0.72 mmol) in CH$_2$Cl$_2$ (10 mL), oxalyl chloride (230 mg, 1.81 mmol), catalytical DMF were added and stirred at 0° C. for 1 h. After the complete consumption of the acid shown by TLC, the volatiles were removed under reduced pressure and the crude acid chloride obtained was taken up in dry CH$_2$Cl$_2$ (5 mL). A solution of methyl amino hydrochloride (238 mg, 3.62 mmol) in CH$_2$Cl$_2$ (5 mL) cooled to 0° C., triethylamine (219 mg, 2.17 mmol) and acid chloride were added dropwise at 5° C. After the completion of the starting material, the reaction mixture was diluted with CH$_2$Cl$_2$ (20 mL), washed with aq NaHCO$_3$ (5 mL×1), brine (5 mL×1) and dried over anhydrous Na$_2$SO$_4$. The combined organic extracts were evaporated under reduced pressure to obtain the crude product which was purified by column chromatography (100-200 mesh silica gel, 30% EtOAc in hexane) to furnish N-methyl-3,5-diphenylpyridazine-4-carboxamide (compound 1) (100 mg, 47%) as a light orange solid.

TLC system: 10% EtOAc-hexane,

Rf-value: 0.6,

Visualization: UV $^1$H NMR (δ, CDCl$_3$, 400 MHz): 9.24 (s, 1H), 7.83-7.80 (m, 2H), 7.56-7.49 (m, 7H), 5.43 (brs, 1H), 2.62 (d, J=4.4 Hz, 3H), 2.17 (s, 1H).

Mass spec. Mass calculated for C$_{18}$H$_{15}$N$_3$O: 289.12; Mass found 290.2 [M+H]$^+$ HPLC Purity Eluent a) 0.05% TFA in H$_2$O b) ACN (Gradient), ZORBAX Eclipse XDB C-18 150*4.6 mm, 5μ; Flow 1.0 mL/min: 97.24% (250 nm); RT=5.33 min LCMS Purity Symmetry C-18 75*4.6 mm, 3.5μ; 97.95% (250 nm); RT=4.19 min; Mass found 290.2 [M+H]$^+$ A variety of other compounds of Formula I-A have been prepared by methods substantially similar to those described in Example 1. The characterization data for these compounds is summarized in Table 1 below.

TABLE 1

Characterization Data for Selected Compounds of Formula I-A

| Compounds | Structure | Yield, % | Mass Found, M + H |
|---|---|---|---|
| 2 | (4,5-diphenylpyridazine-carboxamide with NH(i-Pr)) | 58 | 318.2 |
| 4 | (4,5-diphenylpyridazine-carboxamide with N(CH$_3$)$_2$) | 68 | 304.3 |
| 5 | (4,5-diphenylpyridazine-carboxamide with N(CH$_2$Ph)$_2$) | 28 | 456.2 |
| 7 | (4,5-diphenylpyridazine-carboxamide with N(Et)$_2$) | 64 | 332 |
| 8 | (4,5-diphenylpyridazine-carboxamide with pyrrolidinyl) | 72 | 330 |
| 9 | (4,5-diphenylpyridazine-carboxamide with NH-benzyl) | 73 | 366 |

TABLE 1-continued

Characterization Data for Selected Compounds of Formula I-A

| Compounds | Structure | Yield, % | Mass Found, M + H |
|---|---|---|---|
| 10 | 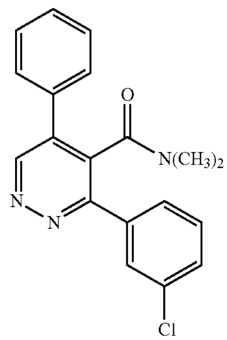 [SMILES: CN(C)C(=O)c1c(-c2ccccc2)cnnc1-c1cccc(Cl)c1] | 66 | 337.9 |
| 12 | 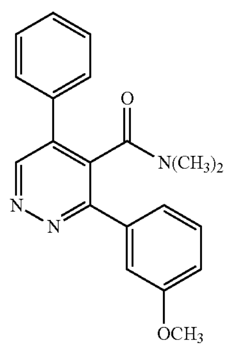 [SMILES: COc1cccc(-c2nncc(-c3ccccc3)c2C(=O)N(C)C)c1] | 62 | 339.9 |
| 14 | 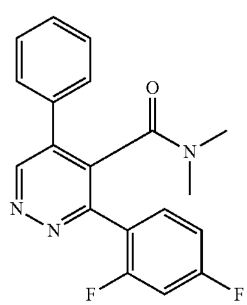 [SMILES: CN(C)C(=O)c1c(-c2ccccc2)cnnc1-c1ccc(F)cc1F] | 63 | 339.9 |
| 16 | 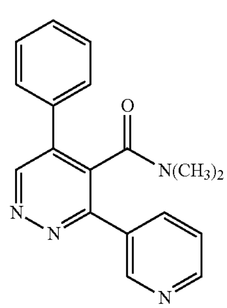 [SMILES: CN(C)C(=O)c1c(-c2ccccc2)cnnc1-c1cccnc1] | 80 | 304 |
| 18 | 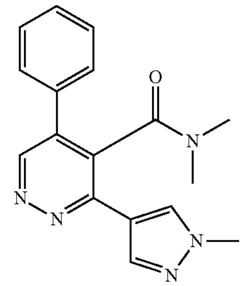 [SMILES: CN(C)C(=O)c1c(-c2ccccc2)cnnc1-c1cnn(C)c1] | 51 | 307.9 |
| 19 | 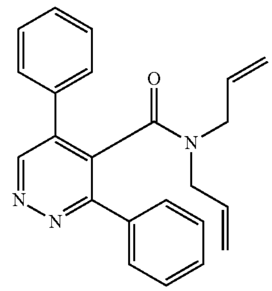 [SMILES: C=CCN(CC=C)C(=O)c1c(-c2ccccc2)cnnc1-c1ccccc1] | 48 | 356 |

Example 2

Synthesis of Compounds 25 and 26

Compounds 25 and 26 were prepared according to synthetic Scheme 5. The syntheses of the intermediates and the final products are detailed as follows.

(A) Methyl 2-(3,5-diphenylpyridazine-4-carboxamido)-3-hydroxypropanoate

The solution of compound 6 (50 mg, 1.81 mmol) in DMF (0.5 mL), DIPEA (93 mg, 0.72 mmol), HATU (138 mg, 0.36 mmol) were sequentially added and stirred for 10 min at rt. Then methyl 2-amino-3-hydroxypropanoate (84 mg, 0.54 mmol) was added and stirred overnight at rt. Reaction was quenched by addition of ice cold water. The precipitated solid was filtered, washed with hexane, dried over anhydrous $Na_2SO_4$ and azeotroped with toluene to furnish methyl 2-(3,5-diphenylpyridazine-4-carboxamido)-3-hydroxypropanoate (20 mg, 29%) as an off white solid.

TLC system: 50% EtOAc-Hexane

Rf-value: 0.2

Visualization: UV $^1$H NMR (δ, DMSO-D$_6$, 400 MHz): 9.33 (s, 1H), 9.18 (d, J=8.4 Hz, 1H) 7.75-7.73 (m, 2H), 7.63-7.61 (m, 2H), 7.51-7.48 (m, 6H), 4.90 (t, J=5.6 Hz, 1H), 4.31-4.26 (m, 1H), 3.52 (s, 3H), 3.41-3.35 (m, 1H), 3.18-3.14 (m, 1H)

Mass spec. Mass calculated for $C_{21}H_{19}N_3O_4$: 377.14; Mass found 378.0 [M+H]$^+$

(B) Methyl 2-(3,5-diphenylpyridazin-4-yl)-4,5-dihydrooxazole-4-carboxylate (compound 25)

To a solution of methyl 2-(3,5-diphenylpyridazine-4-carboxamido)-3-hydroxypropanoate (220 mg, 0.58 mmol) in DCM (15 mL), (diethylamino)sulfur trifluoride (188 mg, 1.16 mmol) was added at −76° C. and stirred at −76° C. for 2 h. Potassium carbonate (400 mg, 2.8 mmol) was added to the reaction mixture at −78° C. and the resulting reaction mixture was warmed to rt. Reaction was quenched by addition of saturated $Na_2CO_3$, extracted with DCM (2×25 mL), washed with brine (1×10 mL) and dried over anhy. $Na_2SO_4$. Evaporation of the solvent under reduced pressure gave crude product methyl 2-(3,5-diphenylpyridazin-4-yl)-4,5-dihydrooxazole-4-carboxylate (compound 25) (130 mg, 61%) as an off white solid.

TLC system: 60% EtOAc-Hexane, Rf-value: 0.6, Visualization: UV $^1$H NMR (δ, DMSO-d6, 400 MHz): 9.47 (s, 1H), 7.66-7.65 (m, 2H), 7.55-7.53 (m, 8H), 4.73 (t, J=7.6 Hz, 1H), 4.35-4.30 (m, 2H), 3.57 (s, 3H)

Mass spec. Mass calculated for $C_{21}H_{17}N_3O_3$: 359.13; Mass found 359.9 [M+H]+

HPLC Purity Eluent a) 0.05% HCOOH in $H_2O$ b) ACN (Gradient), ZORBAX XDB C-18 150*4.6 mm, 5µ; Flow 0.8 mL/min: 98.73% (249 nm); RT=4.49 min LCMS Purity ZORBAX XDB C-18 150*4.6 mm, 5µ; 98.69% (250 nm); RT=4.5 min; Mass found 359.9 [M+H]$^+$

(C) Methyl 2-(3,5-diphenylpyridazin-4-yl)oxazole-4-carboxylate (compound 26)

To a solution of methyl 2-(3-(3-methoxyphenyl)-5-phenylpyridazin-4-yl)-4,5-dihydrooxazole-4-carboxylate (compound 25) (60 mg, 0.16 mmol) in DCM (3 mL), DBU (76 mg, 0.5 mmol), bromotrichloromethane (83 mg, 0.41 mmol) was added at 0° C., stirred for 3 h and then warmed to rt. Reaction was quenched by addition of sat. sodium bicarbonate solution, extracted with DCM (2×25 mL), washed with brine (1×5 mL) and dried over anhydrous $Na_2SO_4$. Evaporation of solvent under reduced pressure gave the crude product that was purified by column chromatography (100-200 mesh silica gel, 35% EtOAc-Hexane) to furnish methyl 2-(3-(3-methoxyphenyl)-5-phenylpyridazin-4-yl)oxazole-4-carboxylate (compound 26) (35 mg, 59%) as an off white solid.

TLC system: 50% EtOAc-Hexane, Rf-value: 0.5, Visualization: UV $^1$H NMR (δ, DMSO-d6, 400 MHz): 9.37 (s, 1H), 8.10 (s, 1H), 7.48-7.46 (m, 2H), 7.41-7.37 (m, 6H), 7.28-7.26 (m, 2H), 3.85 (s, 3H)

Mass spec. Mass calculated for $C_{21}H_{15}N_3O_3$: 357.11; Mass found 357.9 [M+H]$^+$ HPLC Purity Eluent a) 0.05% HCOOH in $H_2O$ b) ACN (Gradient), ZORBAX XDB C-18 150*4.6 mm, 5µ; Flow 0.8 mL/min: 98.36% (253 nm); RT=5.47 min LCMS Purity ZORBAX XDB C-18 150*4.6 mm, 5µ; 98.69% (250 nm); RT=4.5 min; Mass found 359.9 [M+H]$^+$ A variety of other compounds of Formula I-B and Formula I-D have been prepared by methods substantially similar to those described in Example 2. The characterization data for these compounds is summarized in Table 2 below.

TABLE 2

Characterization Data for Selected Compounds of Formula I-B and Formula I-D

| Compound | Structure | Yield (%) | Formula | Mass Found |
|---|---|---|---|---|
| 27 | (5-phenyl-3-(3-chlorophenyl)pyridazin-4-yl oxazole-4-carboxylate, OMe) | 30 | $C_{21}H_{14}ClN_3O_3$ | 391.4 |
| 28 | (5-phenyl-3-(3-methoxyphenyl)pyridazin-4-yl 4,5-dihydrooxazole-4-carboxylate, OMe) | 43 | $C_{22}H_{19}N_3O_4$ | 389.5 |
| 29 | (5-phenyl-3-(3-methoxyphenyl)pyridazin-4-yl oxazole-4-carboxylate, OMe) | 61 | $C_{22}H_{17}N_3O_4$ | 387.9 |
| 30 | (5-phenyl-3-(pyridin-3-yl)pyridazin-4-yl oxazole-4-carboxylate, OMe) | 39 | $C_{20}H_{14}N_4O_3$ | 358.4 |

Example 3

Synthesis of Compound 21

Compound 21 was prepared according to synthetic Scheme 6. The syntheses of the intermediates and the final product are detailed as follows.

(A) N-(1-hydroxypropan-2-yl)-3,5-diphenylpyridazine-4-carboxamide

To a solution of methyl 3,5-diphenylpyrridazine-4-carboxylic acid (compound 6) (250 mg, 0.90 mmol) in DMF (3 mL), DIPEA (0.47 mL, 2.71 mmol), HATU (516 mg, 1.35 mmol) were sequentially added and stirred at rt. After 15 min. 2-amino-1-propanol (203 mg, 2.71 mmol) was added and the reaction mixture was stirred at rt for 12 h. The reaction mixture was diluted with water (20 mL) and extracted with ethyl acetate (3×30 mL). Combined organic extract was washed with water (2×10 mL), brine (1×10 mL) and dried over anhydrous $Na_2SO_4$ and evaporated under reduced pressure to obtain the crude product N-(1-hydroxy propan-2-yl)-3,5-diphenylpyridazine-4-carboxamide (160 mg) as an off white solid.

TLC system: 80% EtOAC-Hexane, Rf-value: 0.5, Visualization: UV

(B) 2-(3,5-diphenylpyridazin-4-yl)-4-methyl-4,5-dihydrooxazole (compound 21)

To a solution of N-(1-hydroxy propan-2-yl)-3,5-diphenylpyridazine-4-carboxamide (150 mg, 0.45 mmol) in DCM (8 mL), DAST (145 mg, 0.90 mmol) was added at −78° C. and stirred for 2 h. After completion of starting materials, solid $K_2CO_3$ (248 mg, 1.80 mmol) was added to the reaction mixture at −78° C. and stirred at rt for 4 h. The reaction mixture was diluted with DCM (20 mL), washed with water (2×8 mL), saturated $NaHCO_3$ (1×5 mL), water (1×5 mL), brine (1×2 mL) and dried over anhy. $Na_2SO_4$. Evaporation of the solvent under reduced pressure gave the crude product which was purified by column chromatography (100-200 mesh silica gel, 35% EtOAc-Hexane) to furnish 2-(3, 5-diphenylpyridazin-4-yl)-4-methyldihydrooxazole (compound 21) (90 mg, 63%) as pale yellow solid.

TLC system: 60% EtOAc-Hexane
Rf-value: 0.5
Visualization: UV
LNB No: COS-10-A004-170
$^1$H NMR ($CDCl_3$, 400 MHz): δ 9.27 (s, 1H), 7.78-7.76 (m, 2H), 7.54-7.47 (m, 8H), 4.19 (t, J=9.2 Hz, 1H), 4.09-4.08 (m, 1H), 3.65 (t, J=7.2 Hz, 1H), 1.02 (d, J=6.4 Hz, 3H)
Mass spec. Mass calculated for $C_{20}H_{17}N_3O$: 315.14; Mass found 315.9 $[M+H]^+$
HPLC Purity Eluent a) 0.1% HCOOH in $H_2O$ b) ACN (Gradient), ZORBAX XDB C-18 150*4.6 mm, 5μ; Flow 0.8 mL/min: 98.41% (250 nm); RT=5.03 min
LCMS Purity Eluent a) 0.1% HCOOH in $H_2O$ b) ACN (Gradient), ZORBAX XDB C-18 150*4.6 mm, 5μ; Flow 0.8 mL/min: 97.31% (250 nm); RT=5.01 min; Mass found 316.0 $[M+H]^+$

Example 4

Synthesis of Compound 20

Compound 20 was prepared according to synthetic Scheme 7. The syntheses of the intermediates and the final product are detailed as follows.

(A) (2-(3,5-diphenylpyridazin-4-yl)oxazol-4-yl)methanol

To a solution of compound 26 (20 mg, 0.056 mmol) in THF (3 mL), LAH (5.0 mg, 0.14 mmol) was added at −30° C. and stirred for 1 h. The reaction mixture was quenched with saturated ammonium chloride solution at −30° C. The reaction mixture was slowly warmed to rt and filtered through celite bed, washed with ethyl acetate. The organic layer was washed with brine, dried over anhy. $Na_2SO_4$ and concentrated under reduced pressure to obtain the crude product gave (2-(3,5-diphenylpyridazin-4-yl)oxazol-4-yl)methanol (16 mg, 88%) as an yellow solid.

TLC system: 50% EtOAc-Hexane, Rf-value: 0.2, Visualization: UV

(B) 4-(bromomethyl)-2-(3,5-diphenylpyridazin-4-yl)oxazole

To a solution of (2-(3,5-diphenylpyridazin-4-yl)oxazol-4-yl)methanol (220 mg, 0.66 mmol) in DCM (8 mL), $PBr_3$ (91 mg, 0.33 mmol) was added at 0° C. and the reaction mixture was warmed to rt and stirred for 12 h. After completion of starting material, reaction was quenched with saturated $NaHCO_3$ solution, extracted with ethyl acetate (2×25 mL), washed with brine (1×10 mL). Solvent was removed under reduced pressure to obtain the crude product 4-(bromomethyl)-2-(3,5-diphenylpyridazin-4-yl)oxazole (250 mg) which was carried to next step without further purification.

TLC system: 50% EtOAc-Hexane, Rf-value: 0.6, Visualization: UV

(C) 2-(3,5-diphenylpyridazin-4-yl)-4-methyloxazole (compound 20)

To a solution of 4-(bromomethyl)-2-(3,5-diphenylpyridazin-4-yl)oxazole (250 mg, 0.64 mmol) in methanol (8 mL), Pd/C (80 mg, wt/wt) was added and the resulting reaction mixture was stirred under hydrogen atmosphere for 1.5 h. The reaction mixture was filtered through a celite bed, washed with methanol and concentrated under reduced pressure to obtain the crude product which was purified by preparative TLC to furnish 2-(3,5-diphenylpyridazin-4-yl)-4-methyloxazole (compound 20) (13.6 mg, 6.8%) as pale yellow gummy liquid.

TLC system: 50% EtOAc-Hexane, Rf-value: 0.5, Visualization: UV
$^1$H NMR (δ, $CDCl_3$, 400 MHz): 9.33 (s, 1H), 7.47-7.37 (m, 9H), 7.26 (s, 2H), 2.05 (s, 3H).
Mass spec. Mass calculated for $C_{20}H_{15}N_3O$: 313.12; Mass found 313.5 $[M]^+$
LCMS Purity at ZORBAX XDB C-18 150*4.6 mm, 5μ; 93.61% (250 nm); RT=6.17 min; Mass found 314.0 $[M+H]^+$ Also prepared in similar fashion was compound 24:
TLC system: 40% EtOAc-Hexane, Rf-value: 0.4, Visualization: UV
$^1$H NMR (δ, $CDCl_3$, 400 MHz): 9.33 (s, 1H), 7.27-7.24 (m, 4H), 7.09 (s, 1H), 6.99-6.96 (m, 2H), 3.78 (m, 3H), 2.06 (s, 3H)
Mass spec. Mass calculated for $C_{21}H_{17}N_3O_2$: 343.13; Mass found 343.5 $[M]^+$
HPLC Purity Eluent a) 0.1% HCOOH in $H_2O$ b) ACN (Gradient), ZORBAX XDB C-18 150*4.6 mm, 5μ; Flow 0.8 mL/min: 92.16% (260 nm); RT=6.26 min

Example 5

Synthesis of Compound 22

Compound 22 was prepared according to synthetic Scheme 8. The syntheses of the intermediates and the final product are detailed as follows.

(A) 1-(2-(3,5-diphenylpyridazin-4-yl)oxazol-4-yl) ethanone

To a solution of compound 26 (50 mg, 0.14 mmol) in THF (4 mL), MeMgBr (0.7 mL, 0.70 mmol) was added at −40° C. and the reaction mixture was warmed to rt and stirred for 1 h. The reaction mixture was quenched by addition of saturated ammonium chloride solution, extracted with ethyl acetate (25 mL), washed with brine (1×10 mL) and dried over $Na_2SO_4$. Evaporation of the solvent under reduced pressure gave the crude product which was purified by column chromatography (100-200 mesh silica gel, 20% EtOAc-hexane) to furnish 1-(2-(3,5-diphenylpyridazin-4-yl)oxazol-4-yl)ethanone (20 mg, 42%) as an off white solid.

TLC system: 50% EtOAc-Hexane, Rf-value: 0.2, Visualization: UV $^1$H NMR (δ, $CDCl_3$, 400 MHz): 9.38 (s, 1H), 8.03 (s, 1H), 7.48-7.38 (m, 8H), 7.29-7.26 (m, 2H), 2.34 (s, 3H).

Mass spec. Mass calculated for $C_{21}H_{15}N_3O_2$: 341.12; Mass found 341.5 [M]$^+$

(B) 1-(2-(3,5-diphenylpyridazin-4-yl)oxazol-4-yl) ethanol

To a solution of 1-(2-(3,5-diphenylpyridazin-4-yl)oxazol-4-yl)ethanone (30 mg, 0.088 mmol) in methanol (4 mL), $NaBH_4$ (8.4 mg, 0.176 mmol) was added at 0° C. and the reaction mixture was warmed to rt and stirred for 2 h. The reaction mixture was quenched in ice cold water, extracted with ethyl acetate (25 mL). The organic layer was washed with brine (1×5 mL), dried over $Na_2SO_4$ and concentrated under reduced pressure to obtain the crude product which was carried further without any purification gave 1-(2-(3,5-diphenylpyridazin-4-yl)oxazol-4-yl)ethanol (30 mg)

TLC system: 50% EtOAc-Hexane, Rf-value: 0.2, Visualization: UV

Mass spec. Mass calculated for $C_{21}H_{17}N_3O_2$: 343.13; Mass found 343.5 [M]$^+$

(C) 2-(3,5-diphenylpyridazin-4-yl)-4-vinyloxazole

To a solution of 1-(2-(3,5-diphenylpyridazin-4-yl)oxazol-4-yl)ethanol (30 mg, 0.08 mmol) in toluene (4 mL), p-tolenesulfonic acid (10 mg) was added and the reaction mixture was refluxed for 2 h. After complete consumption of starting materials, reaction was quenched by solid $K_2CO_3$. Solvents were evaporated under reduced pressure to obtain the crude product that was purified by column chromatography (100-200 mesh silica gel, 20% EtOAc-Hexane) to furnish 2-(3,5-diphenylpyridazin-4-yl)-4-vinyloxazole (25 mg, 89%) as a gummy liquid.

TLC system: 50% EtOAc-Hexane, Rf-value: 0.6, Visualization: UV

Mass spec. Mass calculated for $C_{21}H_{15}N_3O$: 325.12; Mass found 325.4 [M]$^+$

(D) 2-(3,5-diphenylpyridazin-4-yl)-4-ethyloxazole (compound 22)

To a solution of 2-(3,5-diphenylpyridazin-4-yl)-4-vinyloxazole (25 mg, 0.07 mmol) in methanol (4 mL), 10% Pd/C (20 mg, wt/wt) was added and the reaction mixture was stirred under hydrogen atmosphere for 2 h. The reaction mixture was filtered through a celite bed and washed with methanol. Solvent was evaporated under reduced pressure to obtain the crude product that was purified by column chromatography (100-200 mesh silica gel 25% EtOAc-Hexane) to furnish 2-(3,5-diphenylpyridazin-4-yl)-4-ethyloxazole (compound 22) (5.7 mg, 22%) as a pale yellow gummy liquid.

TLC system: 50% EtOAc-Hexane, Rf-value: 0.6, Visualization: UV

LCMS Purity at XBridge C-18 150*4.6 mm, 5µ: 82.73% (258 nm); RT=5.96 min; Mass found 327.5 [M]$^+$

Example 5

Synthesis of Compound 23

Compound 23 was prepared according to synthetic Scheme 9. The syntheses of the intermediates and the final product are detailed as follows.

(A) 2-(2-(3,5-diphenylpyridazin-4-yl)oxazol-4-yl) propan-2-ol

The solution of compound 26 (50 mg, 0.14 mmol) in THF (4 mL), MeMgBr (0.7 mL, 0.7 mmol) was added at −40° C. The reaction mixture was warmed to rt and stirred for 1 hr. Saturated ammonium chloride solution was added, extracted with ethyl acetate (2×25 mL), washed with brine (1×5 mL), dried over anhydrous $Na_2SO_4$ and evaporation of solvent under reduced pressure gave the crude product which was purified by column chromatography (100-200 mesh silica gel, 20% EtOAc-Hexane) to furnish 2-(2-(3,5-diphenylpyridazin-4-yl)oxazol-4-yl)propan-2-ol (25 mg, 50%) as an off white solid.

TLC system: 50% EtOAc-Hexane, Rf-value: 0.2, Visualization: UV $^1$H NMR ($CDCl_3$, 400 MHz): δ 9.35 (s, 3H), 7.44-7.40 (m, 2H), 7.40-7.37 (m, 6H), 7.26-7.25 (m, 2H), 1.36 (s, 6H)

Mass spec. Mass calculated for $C_{22}H_{19}N_3O_2$: 357.15; Mass found 357.5 [M]$^+$

(B) 2-(3,5-diphenylpyridazin-4-yl)-4-(prop-1-en-2-yl)oxazole

To a solution of 2-(2-(3,5-diphenylpyridazin-4-yl)oxazol-4-yl)propan-2-ol (80 mg, 0.22 mmol) in toluene (4 mL), p-toluenesulfonic acid (20 mg) was added and the reaction mixture was refluxed for 2 h. After completion of starting material, reaction was quenched with solid $K_2CO_3$. Solvent was removed under reduced pressure to obtain the crude product that was purified by column chromatography (100-200 mesh silica gel, 20% EtOAc-Hexane) to furnish 2-(3,5-diphenylpyridazin-4-yl)-4-vinyloxazole (70 mg, 92%) as a gummy liquid.

TLC system: 70% EtOAc-Hexane, Rf-value: 0.8, Visualization: UV

Mass spec. Mass calculated for $C_{22}H_{17}N_3O$: 339.14; Mass found 339.5 [M]$^+$

(C) 2-(3,5-diphenylpyridazin-4-yl)-4-isopropyloxazole (compound 23)

To a solution of 2-(3,5-diphenylpyridazin-4-yl)-4-vinyloxazole (70 mg, 0.20 mmol) in methanol (5 mL), 10% Pd/C (35 mg, wt/wt) was added and the resulting reaction mixture was stirred at rt under hydrogen atmosphere for 2 h. The reaction mixture was filtered through celite bed, washed with methanol and evaporation of solvent under reduced pressure gave the crude product which was purified by column chromatography to furnish 2-(3,5-diphenylpyridazin-4-yl)-4-isopropyloxazole (compound 23) (25 mg, 95%) as pale yellow gummy liquid.

TLC system: 50% EtOAc-Hexane
Rf-value: 0.6
Visualization: UV
$^1$H NMR (δ, CDCl$_3$, 400 MHz): 9.31 (s, 1H), 7.45-7.35 (m, 9H), 7.26-7.20 (m, 2H), 2.74-2.70 (m, 1H), 1.06 (d, J=6.8 Hz, 6H)

Mass spec. Mass calculated for C$_{22}$H$_{19}$N$_3$O: 341.15; Mass found 341.5 [M]$^{30}$ HPLC Purity Eluent a) 0.1% HCOOH in H$_2$O b) ACN (Gradient), ZORBAX XDB C-18 150*4.6 mm, 5µ; Flow 1.0 mL/min: 95.71% (258 nm); RT=7.59 min LCMS Purity at XBridge C-18 150*4.6 mm, 5µ; 95.23% (258 nm); RT=7.11 min; Mass found 341.5 [M]$^+$

Example 6

Assessing α5-Containing GABA$_A$ Receptor (GABA$_A$R) Agonist Activity

Step 1: Establish Clones of GABA$_A$R Subunits (α5, β3, γ2, α1, α2 and α3) and Prepare the Corresponding cRNAs: Human clones of GABA$_A$-R α5, β3, γ2, α1, α2 and α3 subunits are obtained from commercial resources (e.g., Ori-Gene, http://www.origene.com and Genescript, http://www.genescript.com). These clones are engineered into pRC, pCDM, pcDNA, and pBluescript KSM vector (for oocyte expression) or other equivalent expression vectors. Conventional transfection agents (e.g., FuGene, Lipofectamine 2000, or others) are used to transiently transfect host cells.

Step 2—Functional GABA$_A$R Assay of α5β3γ2, α1β3γ2, α2β3γ2, and α3β3γ2 Subtypes in *Xenopus oocyte* Expression System: cRNAs encoding α5, β3, γ2, α1, α2 and α3 subunits are transcribed in vitro using T3 mMESSAGE mMACHINE Kit (Ambion) and injected (in a ratio of α:β:γ=2:2:1 or other optimized conditions) into oocytes freshly prepared from *Xenopus laevis*. After two days of culturing, GABA-gated Cl– currents from oocytes are performed using TEVC setups (Warner Instruments, Inc., Foster City, Calif.). GABA, benzodiazepine, and diazepam are used as reference compounds to validate the system.

Step 3—Evaluate Test Compounds for Agonist Activity on the α5β3γ2 Subtype and Test Off-Target Activity on the α1 to α3 Coupled β3γ2 Subtypes when the EC50=5 µM Selectivity Cut-Off is Reached: The GABA-gated Cl– current from oocytes are measured in the TEVC setup in the presence of the test compounds. The agonist activity of each the test compounds is tested in a 5-point dose-response assay. The test compounds include some reference compounds (literature EC50 values for the α5β3γ2subtype are in the range of 3-10 µM). EC50s in the α5β3γ2subtype are obtained for each compound. If the EC50 in α5β3γ2 is <5 µM, then the EC50 of the other three subtypes (α1β2γ2, α2β3γ2 and α3β3γ2) is further determined individually in order to test for selectivity of the compounds in the α5β3γ2subtype over other subtypes.

Step 4—Evaluate Further Test Compounds on the α5β3γ2 Subtype and Test Off-Target Activities when the EC50=0.5 µM Selectivity Cut-Off is reached: The second batch of test compounds are tested using the same strategy, but with a lower EC50 cutoff (0.5 µM). Again, the EC50s of the α5β3γ2 subtype for each of the compounds is determined. The α1 to α3 coupled β3γ2 subtypes are tested only if the EC50 for the α5-containing receptor is <0.5 µM.

Example 7

Evaluating Compounds for Agonist Activity on the GABA$_A$ α5 Receptors

The agonist activity of the compounds of this invention was determined by measuring their effect on GABA-gated Cl– current from *Xenopus oocytes* expressing GABA$_A$ α5β3γ2 subtype receptor in a two-electrode voltage clamp (TEVC) setup. Compounds demonstrating greater than 5% potentiation of the GABA EC$_{50}$ were indicative of compounds with positive allosteric modulation of the GABA$_A$ α5 receptor. That is, these compounds would enhance the effects of GABA at the GABA$_A$ α5 receptor.

Materials

Adult female *Xenopus laevis* frogs were purchased from Nasco (Fort Atkinson, Wis.). Gentamicin, 3-aminobenzoic acid ethyl ester, GABA, Diazepam, Flumazenil, and collagenase were purchased from Sigma (St. Louis, Mo.). All chemicals used were of reagent grade. GABA stocks were prepared in the extracellular solution, i.e., Modified Barth's Saline (MBS) containing NaCl (88 mM), KCl (2 mM), MgSO$_4$ (0.82 mM), Ca(NO$_3$)$_2$ (0.33 mM), CaCl$_2$ (0.41 mM), NaHCO$_3$ (2.4 mM) and HEPES (10 mM). Stock solutions of Diazepam, Flumazenil and compounds of the present invention were prepared in dimethyl sulfoxide (DMSO) and then diluted to an appropriate concentration with the extracellular solution just before use. To avoid adverse effects from DMSO exposure, the final concentration of DMSO was not higher than 0.3% (v/v).

Experimental Procedures (A) Expression of GABA$_A$-R α5β3γ2 or α1β2γ2 Subtype in *Xenopus Oocytes*

*Xenopus oocytes* were isolated according to previously published procedures (see, e.g., Goldin et al. *Methods Enzymol.* 207:266-279 (1992)). The isolated *Xenopus oocytes* were injected with GABA$_A$R cDNAs (1:1:1 ratio for a total volume of 1 ng of α1β2γ2 or α5β3γ2) cloned into mammalian expression vectors. In particular, α1, β2, γ2 were cloned into pcDNA3.1. and α5 and β3 were cloned into pcDNA3.1 myc-His. Vectors were verified by partial sequencing (DNA Core Facility, University of Southern California, USA). After injection, oocytes were stored in incubation medium (Modified Barth's Saline (MBS) supplemented with 2 mM sodium pyruvate, 0.5 mM theophylline and 50 mg/L gentamycin), in petri dishes (VWR, San Dimas, Calif.). All solutions were sterilized by passage through 0.22 µM filters. Oocytes, stored at 18° C., usually expressed GABA$_A$Rs (e.g., α5β3γ2 or α1β2γ2 subtype), 1-2 days after injections. Oocytes were used in experiments for up to 5 days after injection.

(B) GABA Dose-Response in *Xenopus oocyte* Expressing α1 and α5 GABA$_A$ Rs

A high-throughput two-electrode voltage clamp (TEVC) system (OpusXpress A6000; Molecular Devices, Union City, Calif.), which automates the impalement of oocytes, fluid delivery and current recording from 8 oocytes in parallel, was used to carry out all electrophysiological recordings.

*Xenopus Oocytes* expressing GABA$_A$-R α5β3γ2 or α1β2γ2 subtype, as prepared in section (A) above, were placed in 8 chambers of OpusXpress and perfused by MBS at 3 mL/min. Glass electrodes back-filled with 3 M KCl (0.5-3 megaohms) were used. Membrane potential of oocytes was voltage-clamped at −60 mV. Oocytes with holding current larger than 0.5 µA were discarded.

Different concentrations of GABA (3 µM-10 mM for α1-containing GABA$_A$Rs, or 0.3 µM-1 mM for α5-containing GABA$_A$Rs) were applied once for 30 sec, with 5-15 min washes between the applications. Longer wash periods were allowed after the applications of higher GABA concentrations. At the start of each week, a GABA dose-response experiment was conducted to determine an approximate GABA EC$_{50}$ concentration for the batch of oocytes. EC$_{50}$ ranged from 100-200 µM for α1-containing GABA$_A$Rs, and 10-20 µM α5-containing GABA$_A$Rs.

(C) Functional GABA$_A$-R Assay of α5β3γ2 or α1β2γ2 Subtype in *Xenopus Oocyte* Expression System Using Diazepam and Flumazenil as Reference Compounds Diazepam and Flumazenil were used as reference compounds. In this study the GABA-gated Cl$^-$ current from oocytes expressing α5β3γ2 GABA$_A$R was measured in the TEVC setup in the presence of Diazepam and Flumazenil. GABA EC$_{20}$ was applied for 30 sec 4-5 times to establish a stable response. 1 µM Diazepam was pre-applied for 60 sec, followed by co-application of 1 µM Diazepam and GABA at EC$_{20}$ concentration for 30 sec. After a 15-20 min wash, a combination of 1 µM Diazepam and 10 µM Flumazenil was applied for 60 sec followed by co-application of the same combination with GABA at EC$_{20}$ concentrations for 30 sec. After a 15-20 min wash, co-application of 1 µM Diazepam and EC$_{20}$ GABA was repeated to establish the recovery.

The effect of Diazepam was analyzed from the peak amplitude of Diazepam-(plus EC$_{20}$ GABA)-induced current (test 1) with the peak amplitude of GABA-induced current before the Diazepam application (reference). The effect of Flumazenil was determined from the peak amplitude of Diazepam-plus-Flumazenil-(plus EC$_{20}$ GABA)-induced current (test 2) normalized on the peak amplitude of Diazepam-induced current (control). Other compounds may also be used in this study as reference compounds. For example, methyl-6,7-dimethoxy-4-ethyl-beta-carboline-3-carboxylate (DMCM) and L655708 were tested at 1 µM, using the same protocol.

(C) Agonist Activity of Test Compounds on α5β3γ2 Subtype GABA$_A$R

Compounds of the present invention were initially screened at 1 µM for their ability to potentiate an EC$_{50}$ concentration of GABA in oocytes containing GABA$_A$ receptors (α5β3γ2) using a protocol essentially similar to the one presented above for Diazepam and Flumazenil (see section (B)). In this study, the GABA-gated current from oocytes expressing GABA$_A$-R α5β3γ2 subtype was measured in the TEVC setup in the presence of the test compounds. Specifically, GABA EC$_{50}$ was applied for 30 sec 4-5 times to establish stable response. Next, the test compounds (1 µM) were pre-applied for 60 sec, followed by co-administration of the test compounds (1 µM) and GABA at EC$_{50}$ concentration for 30 sec. After a 15-20 min wash, EC$_{50}$ GABA was tested once again. Upon conclusion of compound testing and successful washout, a 1.0 µM Diazepam was tested and used for comparative activity on the two GABA$_A$R subtypes.

The effect of each test compound was determined from the peak amplitude of Diazepam-plus-compound-(plus EC$_{50}$ GABA)-induced current normalized on the peak amplitude of Diazepam-(plus EC$_{50}$ GABA)-induced current (control). Other concentrations of the test compound may also be tested following the same protocol.

A compound which demonstrates greater than 5% potentiation of the GABA EC$_{50}$ is indicative that the compound has a positive allosteric modulatory effect on the GABA$_A$ α5 receptor. Such compound will enhance the effects of GABA at the GABA$_A$ α5 receptor. Exemplary compounds that demonstrated greater than 5% potentiation of the GABA EC$_{50}$ are shown in Table 3 below.

TABLE 3

Exemplary compounds with >5% Potentiation of GABA EC$_{50}$ Concentration in Oocytes containing GABA$_A$ receptors (α5β3γ2)

| Compound | Structure | GABA α5 EC50 % potentiation |
|---|---|---|
| 1 | [structure] | 8.5 |
| 2 | [structure] | 8.2 |
| 3 | [structure] | 11.1 |
| 4 | [structure] | 42 |
| 5 | [structure] | 4.6 |

TABLE 3-continued

Exemplary compounds with >5% Potentiation of GABA EC$_{50}$ Concentration in Oocytes containing GABA$_A$ receptors (α5β3γ2)

| Compound | Structure | GABA α5 EC50 % potentiation |
|---|---|---|
| 9 | 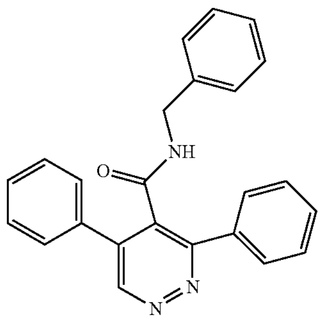 [SMILES: O=C(NCc1ccccc1)c1c(-c2ccccc2)cnnc1-c1ccccc1] | 10 |
| 11 | 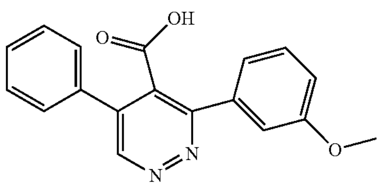 [SMILES: COc1cccc(-c2nncc(-c3ccccc3)c2C(=O)O)c1] | 19.2 |
| 21 | 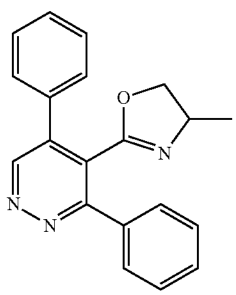 [SMILES: CC1COC(c2c(-c3ccccc3)cnnc2-c2ccccc2)=N1] | 5.3 |
| 22 | 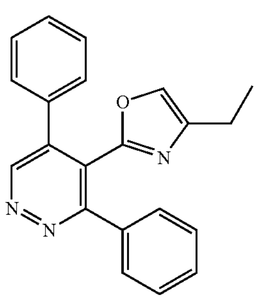 [SMILES: CCc1coc(-c2c(-c3ccccc3)cnnc2-c2ccccc2)n1] | 8.6 |
| 24 | 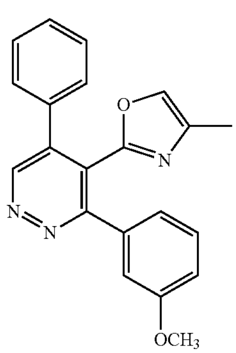 [SMILES: COc1cccc(-c2nncc(-c3ccccc3)c2-c2nc(C)co2)c1] | 6 |
| 25 | | 8.6 |
| 26 | | 15.8 |
| 27 | | 30.5 |
| 29 | | 12.3 |

(D) Evaluate Test Compounds for Off-Target Activity on the α1β2γ2 Subtype

Compounds having a positive allosteric modulatory effect on GABA$_A$ α5 receptors were next evaluated across a range of concentrations (i.e., at 0.01, 0.1, 1, and 100 μM) to determine the concentration response curve at GABA$_A$ α5 receptors (α5β3γ2) and selectivity vs. GABA$_A$ α1 receptors (α1β2γ2). The results are shown in FIGS. 1(A)-(D). Compounds 4, 26, 27 and 29 demonstrated strong positive allosteric modulation of GABA at GABA$_A$ α5 receptors with markedly reduced positive allosteric modulation at GABA$_A$ α1 receptors. Compound 26 demonstrated positive allosteric modulation of GABA at the GABA$_A$ α5 receptor with no evidence of activity at the GABA$_A$ α1 receptor, indicating that this compound is a GABA$_A$ α5 receptor specific agonist, consistent with specificity of this compound for the GABA$_A$ α5 receptor relative to the GABA$_A$ α1 receptor.

(E) Data Analysis

Data for each experimental point were obtained from 4 or more *Xenopus oocytes* and from at least two different frogs. The n refers to the number of *Xenopus* oocytes tested. Results are expressed as mean±SEM. Where no error bars are shown, they are smaller than the symbols. Prism (GraphPAD Software, San Diego, Calif.) and Excel were used to perform curve fitting and statistical analyses. GABA concentration response curves were generated using non-linear regression analysis: $[I=I_{max} [A]^{nH}/([A]^{nH}+EC_{50}^{nH})]$ where I is the peak current recorded following application of a range of agonist concentrations, [A]; $I_{max}$ is the estimated maximum current; $EC_{50}$ is the GABA concentration required for a half-maximal response and $n_H$ is the Hill slope.

Example 8

Effect of Methyl 3,5-diphenylpyridazine-4-carboxylate in Aged-Impaired (AI) Rats Methyl 3,5-diphenylpyridazine-4-carboxylate, corresponding to compound number 6 in van Niel et al. *J. Med. Chem.* 48:6004-6011 (2005), is a selective α5-containing GABA$_A$R agonist. It has an α5 in vitro efficacy of +27 ($EC_{20}$). The effect of methyl 3,5-diphenylpyridazine-4-carboxylate in aged-impaired rats was studied using a RAM task. Moreover, receptor occupancy by methyl 3,5-diphenylpyridazine-4-carboxylate in α5-containing GABA$_A$ receptor was also studied.

(A) Effect of Methyl 3,5-diphenylpyridazine-4-carboxylate in Aged-Impaired Rats Using a Radial Arm Maze (RAM) Behavioral Task The effects of methyl 3,5-diphenylpyridazine-4-carboxylate on the in vivo spatial memory retention of aged-impaired (AI) rats were assessed in a Radial Arm Maze (RAM) behavioral task using vehicle control and four different dosage levels of methyl 3,5-diphenylpyridazine-4-carboxylate (0.1 mg/kg, 0.3 mg/kg, 1 mg/kg and 3 mg/kg, ip). RAM behavioral tasks were performed on eight AI rats. All five treatment conditions (vehicle and four dosage levels) were tested on all eight rats.

The RAM apparatus used consisted of eight equidistantly-spaced arms. An elevated maze arm (7 cm width×75 cm length) projected from each facet of an octagonal center platform (30 cm diameter, 51.5 cm height). Clear side walls on the arms were 10 cm high and were angled at 65° to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided.

The AI rats were initially subjected to a pre-training test (Chappell et al. *Neuropharmacology* 37: 481-487, 1998). The pre-training test consisted of a habituation phase (4 days), a training phase on the standard win-shift task (18 days) and another training phase (14 days) in which a brief delay was imposed between presentation of a subset of arms designated by the experimenter (e.g., 5 arms available and 3 arms blocked) and completion of the eight-arm win-shift task (i.e., with all eight arms available).

In the habituation phase, rats were familiarized to the maze for an 8-minute session on four consecutive days. In each of these sessions, food rewards were scattered on the RAM, initially on the center platform and arms and then progressively confined to the arms. After this habituation phase, a standard training protocol was used, in which a food pellet was located at the end of each arm. Rats received one trial each day for 18 days. Each daily trial terminated when all eight food pellets had been obtained or when either 16 choices were made or 15 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial "information phase" of the trial. Rats were then removed from the maze for 60 seconds, during which time the barriers on the maze were removed, thus allowing access to all eight arms. Rats were then placed back onto the center platform and allowed to obtain the remaining food rewards during this "retention test" phase of the trial. The identity and configuration of the blocked arms varied across trials.

The number of "errors" the AI rats made during the retention test phase was tracked. An error occurred in the trial if the rats entered an arm from which food had already been retrieved in the pre-delay component of the trial, or if the rat re-visited an arm in the post-delay session that it had already visited.

After completion of the pre-training test, rats were subjected to trials with more extended delay intervals, i.e., a two-hour delay, between the information phase (presentation with some blocked arms) and the retention test (presentation of all arms). During the delay interval, rats remained off to the side of the maze in the testing room, on carts in their individual home cages. AI rats were pretreated 30-40 minutes before daily trials with a one-time shot of the following five conditions: 1) vehicle control—5% dimethyl sulfoxide, 25% polyethylene glycol 300 and 70% distilled water; 2) methyl 3,5-diphenylpyridazine-4-carboxylate at 0.1 mg/kg; 3) methyl 3,5-diphenylpyridazine-4-carboxylate at 0.3 mg/kg; 4) methyl 3,5-diphenylpyridazine-4-carboxylate at 1 mg/kg); and 5) methyl 3,5-diphenylpyridazine-4-carboxylate at 3 mg/kg; through intraperitoneal (i.p.) injection. Injections were given every other day with intervening washout days. Each AI rat was treated with all five conditions within the testing period. To counterbalance any potential bias, drug effect was assessed using ascending-descending dose series, i.e., the dose series was given first in an ascending order and then repeated in a descending order. Therefore, each dose had two determinations.

Parametric statistics (paired t-tests) was used to compare the retention test performance of the AI rats in the two-hour delay version of the RAM task in the context of different doses of methyl 3,5-diphenylpyridazine-4-carboxylate and vehicle control (see FIG. 2). The average numbers of errors that occurred in the trials were significantly fewer with methyl 3,5-diphenylpyridazine-4-carboxylate treatment of 3 mg/kg/(average no. of errors±standard error of the mean (SEM)=1.31±0.40) than using vehicle control (average no. of errors±SEM=3.13±0.62). Relative to vehicle control treatment, methyl 3,5-diphenylpyridazine-4-carboxylate significantly improved memory performance at 3 mg/kg (t(7)=4.233, p=0.004).

The therapeutic dose of 3 mg/kg became ineffective when the AI rats were concurrently treated with 0.3 mg/kg of TB21007, a α5-containing $GABA_A$ R inverse agonist. The average numbers of errors made by rats with the combined TB21007/methyl 3,5-diphenylpyridazine-4-carboxylate treatment (0.3 mg/kg TB21007 with 3 mg/kg methyl 3,5-diphenylpyridazine-4-carboxylate) was 2.88±1.32, and was no different from rats treated with vehicle control (3.13±1.17 average errors). Thus, the effect of methyl 3,5-diphenylpyridazine-4-carboxylate on spatial memory is a $GABA_A$ α5 receptor-dependent effect (see FIG. 2).

(B) Effect of Methyl 3,5-diphenylpyridazine-4-carboxylate on α5-Containing $GABA_A$ Receptor Occupancy Animals Adult male Long Evans rats (265-295 g, Charles River, Portage, Mich., n=4/group) were used for $GABA_A$ α5 receptor occupancy studies. Rats were individually housed in ventilated stainless-steel racks on a 12:12 light/dark cycle. Food and water were available ad libitum. In additional studies to evaluate compound exposures at behaviorally active doses, young or aged Long Evan rats (n=2-4/group) were used for these studies.

Compounds

Ro 15-4513 was used as a receptor occupancy (RO) tracer for $GABA_A$ α5 receptor sites in the hippocampus and cerebellum. Ro 15-4513 was chosen as the tracer based on its selectivity for $GABA_A$ α5 receptors relative to other alpha subunit containing $GABA_A$ receptors and because it has been successfully used for $GABA_A$ α5 RO studies in animals and humans (see, e.g., Lingford-Hughes et al., *J. Cereb. Blood Flow Metab.* 22:878-89 (2002); Pym et al, *Br. J. Pharmacol.* 146: 817-825 (2005); and Maeda et al., *Synapse* 47: 200-208 (2003)). Ro 15-4513 (1 μg/kg), was dissolved in 25% hydroxyl-propyl beta-cyclodextrin and administered i.v. 20' prior to the RO evaluations. Methyl 3,5-diphenylpyridazine-4-carboxylate (0.1-10 mg/kg) was synthesized by Nox Pharmaceuticals (India) and was dissolved in 25% hydroxyl-propyl beta-cyclodextrin and administered i.v. 15' prior to tracer injection. Compounds were administered in a volume of 0.5 ml/kg except for the highest dose of methyl 3,5-diphenylpyridazine-4-carboxylate (10 mg/kg) which was administered in a volume of 1 ml/kg due to solubility limitations.

Tissue Preparation and Analysis

The rats were sacrificed by cervical dislocation 20' post tracer injection. The whole brain was rapidly removed, and lightly rinsed with sterile water. Trunk blood was collected in EDTA coated eppendorf tubes and stored on wet ice until study completion. Hippocampus and cerebellum were dissected and stored in 1.5 ml eppendorf tubes, and placed on wet ice until tissue extraction. In a drug naïve rat, six cortical brain tissues samples were collected for use in generating blank and standard curve samples.

Acetonitrile containing 0.1% formic acid was added to each sample at a volume of four times the weight of the tissue sample. For the standard curve (0.1-30 ng/g) samples, a calculated volume of standard reduced the volume of acetonitrile. The sample was homogenized (FastPrep-24, Lysing Matrix D; 5.5 m/s, for 60 seconds or 7-8 watts power using sonic probe dismembrator; Fisher Scientific) and centrifuged for 16-minutes at 14,000 rpm. The (100 μl) supernatant solution was diluted by 300 μl of sterile water (pH 6.5). This solution was then mixed thoroughly and analyzed via LC/MS/MS for R δ 15-4513 (tracer) and methyl 3,5-diphenylpyridazine-4-carboxylate.

For plasma exposures, blood samples were centrifuged at 14000 rpm for 16 minutes. After centrifuging, 50 ul of supernatant (plasma) from each sample was added to 200 μl of acetonitrile plus 0.1% formic acid. For standard curve (1-1000 ng/ml) samples, a calculated volume of standard reduced the volume of acetonitrile. Samples were sonicated for 5 minutes in an ultrasonic water bath, followed by centrifugation for 30 minutes, at 16000 RPM. 100 ul of supernatant was removed from each sample vial and placed in a new glass auto sample vial, followed by the addition of 300 μl of sterile water (pH 6.5). This solution was then mixed thoroughly and analyzed via LC/MS/MS for methyl 3,5-diphenylpyridazine-4-carboxylate.

Receptor occupancy was determined by the ratio method which compared occupancy in the hippocampus (a region of high $GABA_A$ α5 receptor density) with occupancy in the cerebellum (a region with low $GABA_A$ α5 receptor density) and additionally by a high dose of the $GABA_A$ α5 negative allosteric modulator L-655,708 (10 mg/kg, i.v.) to define full occupancy.

Vehicle administration followed by tracer administration of 1 μg/kg, i.v., of Ro 15-4513 resulted in >5-fold higher levels of Ro 15-4513 in hippocampus (1.93±0.05 ng/g) compared with cerebellum (0.36±0.02 ng/g). Methyl 3,5-diphenylpyridazine-4-carboxylate (0.01-10 mg/kg, i.v.) dose-dependently reduced Ro 15-4513 binding in hippocampus, without affecting cerebellum levels of Ro 15-4513 (FIG. 3) with a dose of 10 mg/kg, i.v., demonstrating >90% occupancy (FIG. 4). Both methods of calculating RO yielding very similar results with ED50 values for methyl 3,5-diphenylpyridazine-4-carboxylate as 1.8 mg/kg or 1.1 mg/kg based on the ratio method or using L-755,608 to define occupancy.

Methyl 3,5-diphenylpyridazine-4-carboxylate exposure was below the quantification limits (BQL) at 0.01 mg/kg, i.v., in both plasma and hippocampus and but was detectable at low levels in hippocampus at 0.1 mg/kg, i.v. (see Table 4). Hippocampal exposure was linear as a 10-fold increase in dose from 0.1 to 1 mg/kg, i.v., resulted in a 12-fold increase in exposure. Increasing the dose from 1 to 10 mg/kg, i.v., only increased the exposure by ~5-fold. Plasma exposure increased 12-fold as the dose increased from 1 to 10 mg/kg, i.v.

TABLE 4

% $GABA_A$ α5 Receptor Occupancy by methyl 3,5-diphenyl-pyridazine-4-carboxylate (0.01-10 mg/kg, i.v.). Hippocampus and Plasma Exposure of methyl 3,5-diphenylpyridazine-4-carboxylate by Treatment Group in young Long Evans rats.

| Dose (mg/kg, i.v.) | % RO (L-655,708 Method) (SEM) | % RO (Ratio Method) (SEM) | Plasma ng/mL (SEM) | Hippocampus ng/g (SEM) |
| --- | --- | --- | --- | --- |
| 0.01 | 19.2 (11.1) | 15.7 (9.1) | BQL | BQL |
| 0.1 | 16.4 (4.9) | 13.4 (4.0) | BQL | 14.6 (3.5) |
| 1 | 38.5 (11.2) | 31.5 (9.1) | 62.8 (6.1) | 180.0 (10.3) |
| 10 | 110.0 (6.6) | 90.2 (5.4) | 763.5 (85.7) | 947.2 (51.3) |

Additional studies were conducted in aged Long-Evans rats in order to determine the exposures at the behaviorally relevant doses in the cognition studies. Exposure in young Long-Evans rats was also determined to bridge with the receptor occupancy studies that were conducted in young Long-Evans rats. Exposures in young and aged Long-Evans rats were relatively similar (Table 5, FIG. 5). Increasing the dose 3-fold from 1 to 3 mg/kg, ip resulted in a greater than dose-proportional increase in exposure in young and aged rats in both hippocampus and plasma with increases ranging from 4.5 to 6.6-fold.

TABLE 5

Hippocampus and Plasma Exposure of methyl 3,5-diphenyl-
pyridazine-4-carboxylate in Young Long Evans Rats
by Treatment Group

| Dose (mg/kg, ip) | Young Hippocampus ng/g (SEM) | Young Plasma ng/mL (SEM) | Aged Hippocampus ng/g (SEM) | Aged Plasma ng/mL (SEM) |
|---|---|---|---|---|
| 1 | 25.9 (1.7) | 20.0 (1.4) | 38.8 (21.7) | 45.2 (29.6) |
| 3 | 129.1 (22.4) | 132.9 (19.5) | 177.5 (19.5) | 196 (18.2) |

In the RO studies, an exposure of 180 ng/g in hippocampus (1 mg/kg, i.v.) represented 32-39% receptor occupancy depending on method used to determine RO. This exposure is comparable to that observed in aged rats at 3 mg/kg, i.p., suggesting that 30-40% RO is required for cognitive efficacy in this model.

These studies demonstrated that methyl 3,5-diphenylpyridazine-4-carboxylate produced dose-dependent increase in $GABA_A$ α5 receptor occupancy. Methyl 3,5-diphenylpyridazine-4-carboxylate also demonstrated good brain exposure with brain/plasma ratios>1. The studies further demonstrated that methyl 3,5-diphenylpyridazine-4-carboxylate was producing its cognitive enhancing effects by positive allosteric modulation at the $GABA_A$ α5 subtype receptor.

Example 9

Effect of Ethyl 3-methoxy-7-methyl-9H-benzo[f] imidazo[1,5-a][1,2,4]triazolo[4,3-d][1,4]diazepine-10-carboxylate in Aged-Impaired (AI) Rats Ethyl 3-methoxy-7-methyl-9H-benzo[f]imidazo[1,5-a][1,2,4]triazolo[4,3-d][1,4]diazepine-10-carboxylate, corresponding to compound number 49 in Achermann et al. *Bioorg. Med. Chem. Lett.*, 19:5746-5752 (2009), is a selective α5-containing $GABA_A$ R agonist.

The effect of ethyl 3-methoxy-7-methyl-9H-benzo[f]imidazo[1,5-a][1,2,4]triazolo[4,3-d][1,4]diazepine-10-carboxylate on the in vivo spatial memory retention of aged-impaired (AI) rats was assessed in a Radial Arm Maze (RAM) behavioral task that is essentially similar to the task as described in Example 3 (A), using vehicle control (25% cyclodextrin, which was tested 3 times: at the beginning, middle and end of ascending/descending series) and six different doses levels (0.1 mg/kg, 0.3 mg/kg, 1 mg/kg, 3 mg/kg, 10 mg/kg and 30 mg/kg, each dose was tested twice) of ethyl 3-methoxy-7-methyl-9H-benzo[f]imidazo[1,5-a][1,2,4]triazolo[4,3-d][1,4]diazepine-10-carboxylate. The same experiment was repeated using the same vehicle control and doses of ethyl 3-methoxy-7-methyl-9H-benzo[f]imidazo[1,5-a][1,2,4]triazolo[4,3-d][1,4]diazepine-10-carboxylate, where the vehicle control was tested 5 times, the 3 mg/kg dose of ethyl 3-methoxy-7-methyl-9H-benzo[f]imidazo[1,5-a][1,2,4]triazolo[4,3-d][1,4]diazepine-10-carboxylate was tested 4 times, and the other doses of ethyl 3-methoxy-7-methyl-9H-benzo[f]imidazo[1,5-a][1,2,4]triazolo[4,3-d][1,4]diazepine-10-carboxylate were tested twice.

Parametric statistics (paired t-tests) was used to compare the retention test performance of the AI rats in the four-hour delay version of the RAM task in the context of different doses of ethyl 3-methoxy-7-methyl-9H-benzo[f]imidazo[1,5-a][1,2,4]triazolo[4,3-d][1,4]diazepine-10-carboxylate and vehicle control (see FIGS. 6(A) and 6(B)). Relative to vehicle control treatment, ethyl 3-methoxy-7-methyl-9H-benzo[f] imidazo[1,5-a][1,2,4]triazolo[4,3-d][1,4]diazepine-10-carboxylate significantly improved memory performance at 3 mg/kg (t(7)=4.13, p=0.004, or t(7)=3.08, p=0.018) and at 10 mg/kg (t(7)=2.82, p=0.026).

The effect of ethyl 3-methoxy-7-methyl-9H-benzo[f]imidazo[1,5-a][1,2,4]triazolo[4,3-d][1,4]diazepine-10-carboxylate on α5-containing $GABA_A$ receptor occupancy was also studied following a procedure that is essentially similar to the one as described in Example 8(B) (see above). This study demonstrated that ethyl 3-methoxy-7-methyl-9H-benzo[f]imidazo[1,5-a][1,2,4]triazolo[4,3-d][1,4]diazepine-10-carboxylate (0.01-10 mg/kg, i.v.) reduced Ro 15-4513 binding in hippocampus, without affecting cerebellum levels of Ro 15-4513 (FIG. 7) with a dose of 10 mg/kg, i.v., demonstrating >90% occupancy (FIG. 8).

Example 10

Effect of 6,6 dimethyl-3-(3-hydroxypropyl)thio-1-(thiazol-2-yl)-6,7-dihydro-2-benzothiophen-4(5H)-one in Aged-Impaired Rats Using a Morris Water Maze Behavioral Task 6,6 dimethyl-3-(3-hydroxypropyl)thio-1-(thiazol-2-yl)-6,7-dihydro-2-benzothiophen-4(5H)-one, corresponding to compound 44 in Chambers et al. *J. Med. Chem.* 46:2227-2240 (2003) is a selective α5-containing $GABA_A$ R agonist.

The effects of 6,6 dimethyl-3-(3-hydroxypropyl)thio-1-(thiazol-2-yl)-6,7-dihydro-2-benzothiophen-4(5H)-one on the in vivo spatial memory retention of aged-impaired (AI) rats were assessed in a Morris water maze behavioral task. A water maze is a pool surrounded with a novel set of patterns relative to the maze. The training protocol for the water maze may be based on a modified water maze task that has been shown to be hippocampal-dependent (de Hoz et al., *Eur. J. Neurosci.*, 22:745-54, 2005; Steele and Morris, *Hippocampus* 9:118-36, 1999).

Cognitively impaired aged rats were implanted unilaterally with a cannula into the lateral ventricle. Stereotaxic coordinates were 1.0 mm posterior to bregma, 1.5 mm lateral to midline, and 3.5 mm ventral to the skull surface. After about a week of recovery, the rats were pre-trained in a water maze for 2 days (6 trials per day) to locate a submerged escape platform hidden underneath the surface of the pool, in which the escape platform location varied from day to day. No intracerebroventricular (ICV) infusion was given during pre-training After pre-training, rats received ICV infusion of either 100 μg 6,6 dimethyl-3-(3-hydroxypropyl)thio-1-(thiazol-2-yl)-6,7-dihydro-2-benzothiophen-4(5H)-one (n=6) in 5 μl DMSO or vehicle DMSO (n=5) 40 min prior to water maze training and testing. Training consisted of 8 trials per day for 2 days where the hidden escape platform remained in the same location. Rats were given 60 seconds to locate the platform with a 60 seconds inter-trial interval. The rats were given a probe test (120 seconds) 24 hr after the end of training where the escape platform was removed. During the training, there were 4 blocks, where each block had 4 training trials.

Rats treated with vehicle and 6,6 dimethyl-3-(3-hydroxypropyl)thio-1-(thiazol-2-yl)-6,7-dihydro-2-benzothiophen-4(5H)-one found the escape platform about the same time at the beginning of training (block 1). In this block of training, rats treated with vehicle and 6,6 dimethyl-3-(3-hydroxypropyl)thio-1-(thiazol-2-yl)-6,7-dihydro-2-benzothiophen-4(5H)-one both spent about 24 seconds to find the escape platform. However, rats treated with 6,6 dimethyl-3-(3-hydroxypropyl)thio-1-(thiazol-2-yl)-6,7-dihydro-2-benzothiophen-4(5H)-one were able to find the platform more proficiently (i.e., quicker) at the end of training (block 4) than those treated with vehicle alone. In block 4, rats treated with 6,6 dimethyl-3-(3-hydroxypropyl)thio-1-(thiazol-2-yl)-6,7-dihydro-2-benzothiophen-4(5H)-one spent about 9.6 seconds to find the escape platform, while rats treated with vehicle spent about 19.69 seconds. These results suggest that 6,6 dimethyl-3-(3-hydroxypropyl)thio-1-(thiazol-2-yl)-6,7-dihydro-2-benzothiophen-4(5H)-one improved the learning of the water maze task in rats (see FIG. 9(A)).

During a test trial 24 hr after training, the escape platform was removed. The search/swim pattern of the rats was used to measure whether the rats remember where the escape platform was located during pre-trial training in order to test for the long-term memory of the rats. In this trial, "target annulus" is a designated area 1.5 times the size of the escape platform around the area where the platform was located during pre-trial training "Opposite annulus" is a control area of the same size as the size of the target annulus, which is located opposite to the target annulus in the pool. If the rats had good long term memory, they would tend to search in the area surrounding the location where the platform was during the pre-trial training (i.e., the "target" annulus; and not the "opposite" annulus). "Time in annulus" is the amount of time in seconds that the rat spent in the target or opposite annulus area. "Number (#) of crossings" in annulus is the number of times the rat swam across the target or opposite annulus area.

Rats received vehicle spent the same amount of time in the target annulus and opposite annulus, indicating that these rats did not seem to remember where the platform was during the pre-trial training. By contrast, rats treated with 6,6 dimethyl-3-(3-hydroxypropyl)thio-1-(thiazol-2-yl)-6,7-dihydro-2-benzothiophen-4(5H)-one spent significantly more time in the target annulus, and crossed the "target annulus" more often, as compared to the time they spent in, or the number of times they crossed the "opposite annulus". These results suggest that 6,6 dimethyl-3-(3-hydroxypropyl)thio-1-(thiazol-2-yl)-6,7-dihydro-2-benzothiophen-4(5H)-one improved the long-term memory of rats in the water maze task (see, FIGS. 9(B) and 9(C)).

Compounds of the present invention demonstrated positive allosteric modulatory effect on the $GABA_A$ $\alpha 5$ receptor (See, e.g., Example 7). These compounds will enhance the effects of GABA at the $GABA_A$ $\alpha 5$ receptor.

Therefore, compounds of the present invention should produce cognitive enhancing effects in aged-impaired animals (such as rats), similar to the effects produced by other $GABA_A$ $\alpha 5$ receptor selective agonists, such as methyl 3,5-diphenylpyridazine-4-carboxylate, ethyl 3-methoxy-7-methyl-9H-benzo[f]imidazo[1,5-a][1,2,4]triazolo[4,3-d][1,4]diazepine-10-carboxylate, and 6,6 dimethyl-3-(3-hydroxypropyl)thio-1-(thiazol-2-yl)-6,7-dihydro-2-benzothiophen-4(5H)-one (See, e.g., Examples 8-10).

The invention claimed is:
1. A compound of formula I:

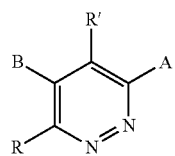

I or a pharmaceutically acceptable salt thereof, wherein:
R' is —C(O)NR$^1$R$^2$ or a 5-membered heterocyclic or heteroaryl ring having 1-3 heteroatoms selected from N, NH, O, SO, and SO$_2$; wherein the 5-membered heterocyclic or heteroaryl ring has 0-3 substituents selected independently from J;

R$^1$ and R$^2$ are independently selected from:
H—,
(C1-C12)-aliphatic-,
(C3-C10)-cycloalkyl-,
(C3-C10)-cycloalkenyl-,
(C6-C10)-aryl-,
(C5-C10)-heteroaryl-, and (C3-C10)-heterocyclo-;
or R$^1$ and R$^2$ may be taken together with the nitrogen atom to which they are attached to form a 3- to 10-membered aromatic or non-aromatic ring having 0-3 substituents independently selected from J, and having 0-3 additional heteroatoms independently selected from N, O, S, SO, or SO$_2$;
wherein each of R$^1$ and R$^2$ is independently substituted at each substitutable position with 0-3 substituents independently selected from J;

R is H, halogen or (C1-C12)-aliphatic-, wherein said (C1-C12)-aliphatic group is substituted with 0-3 substituents independently selected from J;

A is (C6-C10)-aryl- or (C5-C10)-heteroaryl;
B is (C6-C10)-aryl-;
wherein A and B are each independently substituted with 0-5 substituents independently selected from J;

each J is independently selected from:
halogen, —OR$^3$, —NO$_2$, —CN, —CF$^3$, —OCF$_3$, —R$^3$, oxo, thioxo, 1,2-methylenedioxy, 1,2-ethylenedioxy, =N(R$^3$), =N(OR$^3$), —N(R$^3$)$_2$, —SR$^3$, —SOR$^3$, —SO$_2$R$^3$, —SO$_2$N(R$^3$)$_2$, —SO$_3$R$^3$, —C(O)R$^3$, —C(O)C(O)R$^3$, —C(O)CH$_2$C(O)R$^3$, —C(S)R$^3$, —C(S)OR$^3$, —C(O)OR$^3$, —C(O)C(O)OR$^3$, —C(O)C(O)N(R$^3$)$_2$, —OC(O)R$^3$, —C(O)N(R$^3$)$_2$, —OC(O)N(R$^3$)$_2$, —C(S)N(R$^3$)$_2$, —(CH$_2$)$_{0-2}$NHC(O)R$^3$, —N(R$^3$)N(R$^3$)COR$^3$, —N(R$^3$)N(R$^3$)C(O)OR$^3$, —N(R$^3$)N(R$^3$)CON(R$^3$)$_2$, —N(R$^3$)SO$_2$R$^3$, —N(R$^3$)SO$_2$N(R$^3$)$_2$, —N(R$^3$)C(O)OR$^3$, —N(R$^3$)C(O)R$^3$, —N(R$^3$)C(S)R$^3$, —N(R$^3$)C(O)N(R$^3$)$_2$, —N(R$^3$)C(S)N(R$^3$)$_2$, —N(COR$^3$)COR$^3$, —N(OR$^3$)R$^3$, —C(=NH)N(R$^3$)$_2$, —C(O)N(OR$^3$)R$^3$, —C(=NOR$^3$)R$^3$, —OP(O)(OR$^3$)$_2$, —P(O)(R$^3$)$_2$, —P(O)(OR$^3$)$_2$, and —P(O)(H)(OR$^3$);

each R$^3$ is independently selected from:
H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
or two R$^3$ groups bound to the same atom may be taken together with the atom to which they are bound to form a 3- to 10-membered aromatic or non-aromatic ring having 1-3 heteroatoms independently selected from N, O, S, SO, and SO$_2$, wherein said ring is optionally fused to a (C6-C10)aryl, (C5-C10)heteroaryl, (C3-C10)cycloalkyl, or a (C3-C10)heterocyclyl;

provided that said compound of formula I is not:

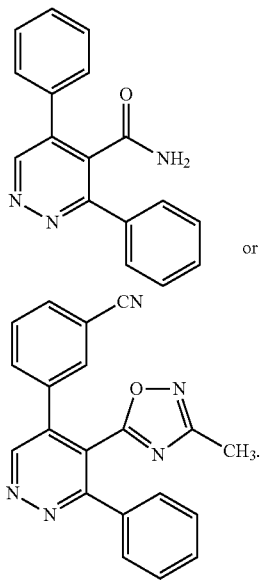

or

2. A compound of formula I:

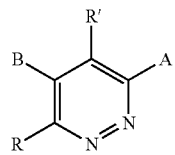

or a pharmaceutically acceptable salt thereof,
wherein:
R' is —C(O)NR$^1$R$^2$ wherein
  R$^1$ and R$^2$ are each independently selected from:
  H—,
  (C1-C12)-aliphatic-,
  (C3-C10)-cycloalkyl-,
  (C3-C10)-cycloalkenyl-,
  (C6-C10)-aryl-,
  (C5-C10)-heteroaryl-, and (C3-C10)-hetero-;
  or R$^1$ and R$^2$ may be taken together with the nitrogen atom to which they are attached form a 3- to 10-membered aromatic or non-aromatic ring having 0-3 additional heteroatoms independently selected from N, O, S, SO, or SO$_2$;
  wherein each of R$^1$ and R$^2$ is independently substituted at each substitutable position with 0-3 substituents independently selected from J;
or R' is a 5-membered heteroaryl ring having 1-3 heteroatoms selected from N, NH, O, SO, and SO$_2$; wherein the 5-membered heteroaryl ring has 0-2 substituents selected independently from J;
R is H, halogen or (C1-C12)-aliphatic-, wherein said (C1-C12)-aliphatic group is substituted with 0-3 substituents independently selected from J;
A is (C6-C10)-aryl- or (C5-C10)-heteroaryl;
B is (C6-C10)-aryl-;
wherein A and B are each independently substituted with 0-5 substituents independently selected from J;

each J is independently selected from:
  halogen, —OR$^3$, —NO$_2$, —CN, —CF$^3$, —OCF$_3$, —R$^3$, oxo, thioxo, 1,2-methylenedioxy, 1,2-ethylenedioxy, =N(R$^3$), =N(OR$^3$), —N(R$^3$)$_2$, —SR$^3$, —SOR$^3$, —SO$_2$R$^3$, —SO$_2$N(R$^3$)$_2$, —SO$_3$R$^3$, —C(O)R$^3$, —C(O)C(O)R$^3$, —C(O)CH$_2$C(O)R$^3$, —C(S)R$^3$, —C(S)OR$^3$, —C(O)OR$^3$, —C(O)C(O)OR$^3$, —C(O)C(O)N(R$^3$)$_2$, —OC(O)R$^3$, —C(O)N(R$^3$)$_2$, —OC(O)N(R$^3$)$_2$, —C(S)N(R$^3$)$_2$, —(CH$_2$)$_{0-2}$NHC(O)R$^3$, —N(R$^3$)N(R$^3$)COR$^3$, —N(R$^3$)N(R$^3$)C(O)OR$^3$, —N(R$^3$)N(R$^3$)CON(R$^3$)$_2$, —N(R$^3$)SO$_2$R$^3$, —N(R$^3$)SO$_2$N(R$^3$)$_2$, —N(R$^3$)C(O)OR$^3$, —N(R$^3$)C(O)R$^3$, —N(R$^3$)C(S)R$^3$, —N(R$^3$)C(O)N(R$^3$)$_2$, —N(R$^3$)C(S)N(R$^3$)$_2$, —N(COR$^3$)COR$^3$, —N(OR$^3$)R$^3$, —C(=NH)N(R$^3$)$_2$, —C(O)N(OR$^3$)R$^3$, —C(=NOR$^3$)R$^3$, —OP(O)(OR$^3$)$_2$, —P(O)(R$^3$)$_2$, —P(O)(OR$^3$)$_2$, and —P(O)(H)(OR$^3$);
each R$^3$ is independently selected from:
  H—,
  (C1-C12)-aliphatic-,
  (C3-C10)-cycloalkyl-,
  (C3-C10)-cycloalkenyl-,
  [(C3-C10)-cycloalkyl]-(C1-C12)-aliphatic-,
  [(C3-C10)-cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, and
  (C5-C10)-heteroaryl-(C1-C12)-aliphatic-;
  or two R$^3$ groups bound to the same atom may be taken together with the atom to which they are bound to form a 3- to 10-membered aromatic or non-aromatic ring having 1-3 heteroatoms independently selected from N, O, S, SO, and SO$_2$, wherein said ring is optionally fused to a (C6-C10)aryl, (C5-C10)heteroaryl, (C3-C10)cycloalkyl, or a (C3-C10)heterocyclyl;
provided that said compound of formula I is not:

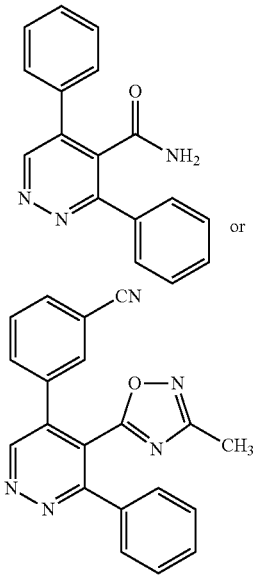

3. The compound according to claim 1 or 2, wherein the compound has the Formula I-A:

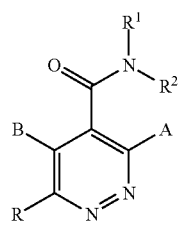

I-A or a pharmaceutically acceptable salt thereof, wherein $R^1$, $R^2$, R, A and B are as defined in claim 1 or 2.

4. The compound according to claim 3, wherein at least one of $R^1$ and $R^2$ is hydrogen.

5. The compound according to claim 4, wherein $R^1$ and $R^2$ are each independently hydrogen.

6. The compound according to claim 3, wherein at least one of $R^1$ and $R^2$ is (C1-C12)-aliphatic- substituted at each substitutable position with 0-3 substituents independently selected from J.

7. The compound according to claim 6, wherein $R^1$ and $R^2$ are each independently (C1-C12)-aliphatic- substituted at each substitutable position with 0-3 substituents independently selected from J.

8. The compound according to claim 7, wherein $R^1$ and $R^2$ are each independently unsubstituted (C1-C4)-aliphatic.

9. The compound according to claim 8, wherein $R^1$ and $R^2$ are each independently methyl, ethyl or allyl.

10. The compound according to claim 7, wherein $R^1$ and $R^2$ are each independently (C1-C4)-alkyl, and wherein at least one of $R^1$ and $R^2$ is substituted with at least one (C6-C10)-aryl.

11. The compound according to claim 10, wherein $R^1$ and $R^2$ are each independently substituted with at least one (C6-C10)-aryl.

12. The compound according to claim 10 or 11, wherein the at least one (C6-C10)-aryl is phenyl.

13. The compound according to claim 6, wherein $R^1$ is H— and $R^2$ is (C1-C12)-aliphatic-substituted at each substitutable position with 0-3 substituents independently selected from J.

14. The compound according to claim 13, wherein $R^2$ is unsubstituted (C1-C4)-alkyl.

15. The compound according to claim 14, wherein $R^2$ is methyl or isopropyl.

16. The compound according to claim 13, wherein $R^2$ is substituted with at least one (C6-C10)-aryl.

17. The compound according to claim 16, wherein the at least one (C6-C10)-aryl is phenyl.

18. The compound according to claim 3, wherein $R^1$ and $R^2$ taken together with the atom to which they are attached form a C5-C10 aromatic or non-aromatic ring.

19. The compound according to claim 18, wherein $R^1$ and $R^2$ taken together with the atom to which they are attached form a pyrrolidine ring.

20. The compound according to claim 1 or 2, wherein the compound has the Formula I-B:

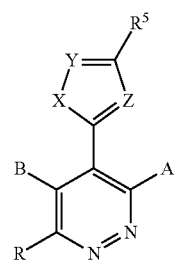

I-B or a pharmaceutically acceptable salt thereof, and wherein:

X is selected from —N($R^4$)—, —O—, and —S—;

Y is —$CR^4$— or —N=;

Z is —$CR^4$— or —N=; and $R^4$ and $R^5$ are each independently selected from:

halogen, —$OR^3$, —$NO_2$, —CN, —$CF_3$, —$OCF_3$, —$R^3$, oxo, thioxo, 1,2-methylenedioxy, 1,2-ethylenedioxy, =N($R^3$), =N(O$R^3$), —N($R^3$)$_2$, —S$R^3$, —SO$R^3$, —SO$_2R^3$, —SO$_2$N($R^3$)$_2$, —SO$_3R^3$, —C(O)$R^3$, —C(O)C(O)$R^3$, —C(O)CH$_2$C(O)$R^3$, —C(S)$R^3$, —C(S)O$R^3$, —C(O)O$R^3$, —C(O)C(O)O$R^3$, —C(O)C(O)N($R^3$)$_2$, —OC(O)$R^3$, —C(O)N($R^3$)$_2$, —OC(O)N($R^3$)$_2$, —C(S)N($R^3$)$_2$, —(CH$_2$)$_{0-2}$NHC(O)$R^3$, —N($R^3$)N($R^3$)COR$^3$, —N($R^3$)N($R^3$)C(O)O$R^3$, —N($R^3$)N($R^3$)CON($R^3$)$_2$, —N($R^3$)SO$_2R^3$, —N($R^3$)SO$_2$N($R^3$)$_2$, —N($R^3$)C(O)O$R^3$, —N($R^3$)C(O)$R^3$, —N($R^3$)C(S)$R^3$, —N($R^3$)C(O)N($R^3$)$_2$, —N($R^3$)C(S)N($R^3$)$_2$, —N(COR$^3$)COR$^3$, —N(O$R^3$)$R^3$, —C(=NH)N($R^3$)$_2$, —C(O)N(O$R^3$)$R^3$, —C(=NO$R^3$)$R^3$, —OP(O)(O$R^3$)$_2$, —P(O)($R^3$)$_2$, —P(O)(O$R^3$)$_2$, and —P(O)(H)(O$R^3$).

21. The compound according to claim 20, wherein X is —O—.

22. The compound according to claim 20, wherein Z is —N=.

23. The compound according to claim 20, wherein X is —O— and Z is —N=.

24. The compound according to claim 20, wherein Y is —$CR^4$— and $R^4$ is H or (C1-C12)-aliphatic.

25. The compound according to claim 24, wherein $R^4$ is H.

26. The compound according to claim 24, wherein $R^4$ is (C1-C4)-alkyl-.

27. The compound according to claim 20, wherein $R^5$ is (C1-C12)-aliphatic- or —C(O)O$R^3$.

28. The compound according to claim 27, wherein $R^5$ is (C1-C4)-alkyl-.

29. The compound according to claim 28, wherein $R^5$ is methyl or ethyl.

30. The compound according to claim 27, wherein $R^5$ is —C(O)O$R^3$, wherein $R^3$ is (C1-C12)-aliphatic-.

31. The compound according to claim 30, wherein $R^3$ is (C1-C4)-alkyl-.

32. The compound according to claim 31, wherein $R^3$ is methyl.

33. The compound according to claim 20, wherein X is —O—, Z is —N=, Y is —$CR^4$— or —N=, and $R^5$ is (C1-C12)-aliphatic- or —C(O)O$R^3$.

34. The compound according to claim 1, wherein the compound has the Formula I-D:

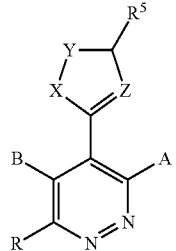

or a pharmaceutically acceptable salt thereof;
wherein:
X, and Y are independently selected from —C(R⁴)₂—, —N(R⁴)—, —O—, and —S—;
Z is —N═; and
each of R⁴ and R⁵ are independently selected from:
halogen, —OR³, —NO₂, —CN, —CF³, —OCF₃, —R³, oxo, thioxo, 1,2-methylenedioxy, 1,2-ethylenedioxy, ═N(R³), ═N(OR³), —N(R³)₂, —SR³, —SOR³, —SO₂R³, —SO₂N(R³)₂, —SO₃R³, —C(O)R³, —C(O)C(O)R³, —C(O)CH₂C(O)R³, —C(S)R³, —C(S)OR³, —C(O)OR³, —C(O)C(O)OR³, —C(O)C(O)N(R³)₂, —OC(O)R³, —C(O)N(R³)₂, —OC(O)N(R³)₂, —C(S)N(R³)₂, —(CH₂)₀₋₂NHC(O)R³, —N(R³)N(R³)COR³, —N(R³)N(R³)C(O)OR³, —N(R³)N(R³)CON(R³)₂, —N(R³)SO₂R³, —N(R³)SO₂N(R³)₂, —N(R³)C(O)OR³, —N(R³)C(O)R³, —N(R³)C(S)R³, —N(R³)C(O)N(R³)₂, —N(R³)C(S)N(R³)₂, —N(COR³)COR³, —N(OR³)R³, —C(═NH)N(R³)₂, —C(O)N(OR³)R³, —C(═NOR³)R³, —OP(O)(OR³)₂, —P(O)(R³)₂, —P(O)(OR³)₂, and —P(O)(H)(OR³);
and A, B and R are as defined in claim 1.

35. The compound according to claim 34, wherein X is —O—.

36. The compound according to claim 34, wherein Y is —C(R⁴)₂—.

37. The compound according to claim 36, wherein at least one R⁴ is H or (C1-C12)-aliphatic.

38. The compound according to claim 37, wherein each is independently R⁴ are H.

39. The compound according to claim 37, wherein at least one R⁴ is (C1-C4)-alkyl-.

40. The compound according to claim 34, wherein R⁵ is (C1-C12)-aliphatic- or —C(O)OR³.

41. The compound according to claim 40, wherein R⁵ is (C1-C4)-alkyl-.

42. The compound according to claim 41, wherein R⁵ is methyl or ethyl.

43. The compound according to claim 40, wherein R⁵ is —C(O)OR³ and R³ is (C1-C12)-aliphatic-.

44. The compound according to claim 43, wherein R³ is (C1-C4)-alkyl-.

45. The compound according to claim 44, wherein R³ is methyl.

46. The compound according to claim 34, wherein X is —O—, Z is —N═, Y is —C(R⁴)₂—, and R⁵ is (C1-C12)-aliphatic- or —C(O)OR³.

47. The compound according to claim 1 or 2, wherein A is (C6-C10)-aryl- or (C5-C10)-heteroaryl-, each of said aryl or heteroaryl being optionally and independently substituted with 1 to 5 substituents independently selected from J.

48. The compound according to claim 47, wherein A is phenyl, optionally substituted with 1 to 5 substituents independently selected from J.

49. The compound according to claim 48, wherein the phenyl is unsubstituted or substituted with at least one halogen or —OR³.

50. The compound according to claim 49, wherein the phenyl is substituted with at least one F, Cl, or —OCH₃.

51. The compound according to claim 47, wherein A is a 5-membered or 6-membered heteroaryl optionally substituted with 1 to 5 substituents independently selected from J.

52. The compound according to claim 51, wherein the heteroaryl is pyrazolyl or pyridyl.

53. The compound according to claim 52, wherein the heteroaryl is unsubstituted or substituted with at least one (C1-C12)-aliphatic group.

54. The compound according to claim 53, wherein the heteroaryl is substituted with at least one —CH₃.

55. The compound according to claim 1 or 2, wherein B is (C6-C10)-aryl-, optionally substituted with 1 to 5 substituents independently selected from J.

56. The compound according to claim 55, wherein B is phenyl optionally substituted with 1 to 5 substituents independently selected from J.

57. The compound according to claim 56, wherein A is phenyl, pyrazolyl or pyridyl, optionally substituted with 1 to 3 substituents independently selected from J.

58. The compound according to claim 1 or 2, wherein:
B is phenyl;
A is phenyl, pyrazolyl or pyridyl, substituted with 0-2 substituents independently selected from —OR³ wherein R³ is (C1-C4)alkyl-, halogen and (C1-C4) alkyl-;
R is hydrogen;
R' is selected from the group consisting of:
(1) —C(O)NR¹R², wherein
R¹ and R² are each independently unsubstituted (C1-C4)-aliphatic-,
or R¹ and R² are each independently (C1-C4)-alkyl, wherein at least one of R¹ and R² is substituted with at least one phenyl,
or R¹ is H, and R² is unsubstituted (C1-C4)-alkyl,
or R¹ and R² taken together with the nitrogen atom to which they are bound form a 5-membered non-aromatic ring; and
(2) a 5-membered heterocyclic or heteroaryl ring having one nitrogen atom and one oxygen atom, wherein the 5-membered heterocyclic or heteroaryl ring has 0-2 substituents selected independently from (C1-C4)-alkyl- and —C(O)OR³ wherein R³ is (C1-C4)alkyl-.

59. The compound according to claim 1 or 2, wherein:
B is phenyl;
A is phenyl substituted with 0 or 1 substituent selected from —OR³ wherein R³ is (C1-C4)alkyl-, and halogen;
R is hydrogen;
R' is selected from the group consisting of:
(1) —C(O)NR¹R², wherein
R¹ and R² are each independently (C1-C4)-alkyl-,
or R¹ and R² are each independently (C1-C4)-alkyl, wherein at least one of R¹ and R² is substituted with one phenyl,
or R¹ is H, and R² is (C1-C4)-alkyl; and
(2) a 5-membered heterocyclic or heteroaryl ring having one nitrogen atom and one oxygen atom, wherein the 5-membered heterocyclic or heteroaryl ring has 1 substituent selected from (C1-C4)-alkyl- and —C(O)OR³ wherein R³(C1-C4)alkyl-.

60. The compound according to claim 1 or 2, wherein the compound is selected from:

| Compound | Structure |
|---|---|
| 1 | 4,5-diphenyl-N-methylpyridazine-4-carboxamide |
| 2 | 4,5-diphenyl-N-isopropylpyridazine-4-carboxamide |
| 4 | 4,5-diphenyl-N,N-dimethylpyridazine-4-carboxamide |
| 5 | N,N-dibenzyl-4,5-diphenylpyridazine-4-carboxamide |
| 7 | N-ethyl-4,5-diphenylpyridazine-4-carboxamide |
| 8 | 4,5-diphenyl-4-(pyrrolidine-1-carbonyl)pyridazine |
| 9 | N-benzyl-4,5-diphenylpyridazine-4-carboxamide |
| 10 | 3-(3-chlorophenyl)-N,N-dimethyl-5-phenylpyridazine-4-carboxamide |
| 12 | 3-(3-methoxyphenyl)-N,N-dimethyl-5-phenylpyridazine-4-carboxamide |
| 14 | 3-(2,4-difluorophenyl)-N,N-dimethyl-5-phenylpyridazine-4-carboxamide |

79
-continued

| Compound | Structure |
|---|---|
| 16 | 4-(dimethylcarbamoyl)-5-phenyl-3-(pyridin-3-yl)pyridazine |
| 18 | N,N-dimethyl-3-(1-methyl-1H-pyrazol-4-yl)-5-phenylpyridazine-4-carboxamide |
| 19 | N-allyl-3,5-diphenyl-N-(prop-2-yn-1-yl)pyridazine-4-carboxamide |
| 20 | 4-(4-methyloxazol-2-yl)-3,5-diphenylpyridazine |
| 21 | 4-((S)-4-methyl-4,5-dihydrooxazol-2-yl)-3,5-diphenylpyridazine |

80
-continued

| Compound | Structure |
|---|---|
| 22 | 4-(4-ethyloxazol-2-yl)-3,5-diphenylpyridazine |
| 23 | 4-(4-isopropyloxazol-2-yl)-3,5-diphenylpyridazine |
| 24 | 3-(3-methoxyphenyl)-4-(4-methyloxazol-2-yl)-5-phenylpyridazine |
| 25 | 1-((S)-2-(3,5-diphenylpyridazin-4-yl)-4,5-dihydrooxazol-4-yl)ethanone |
| 26 | methyl 2-(3,5-diphenylpyridazin-4-yl)oxazole-4-carboxylate |

| Compound | Structure |
|---|---|
| 27 | 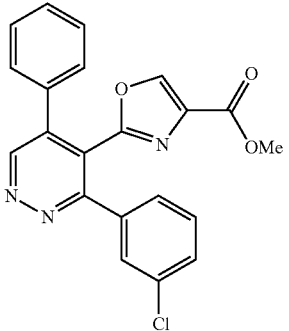 [SMILES: COC(=O)c1coc(-c2c(-c3ccccc3)cnnc2-c2cccc(Cl)c2)n1] |
| 28 | 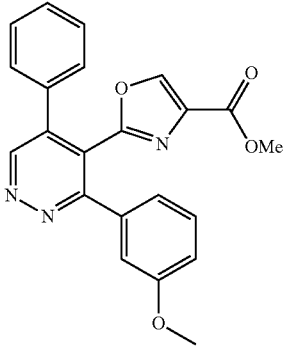 [SMILES: COC(=O)c1coc(-c2c(-c3ccccc3)cnnc2-c2cccc(OC)c2)n1] |
| Compound | Structure |
|---|---|
| 29 | 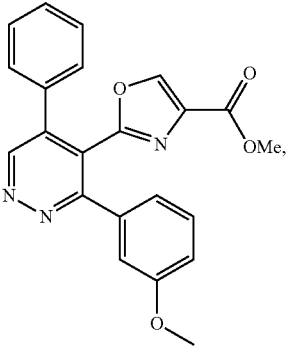 and |
| 30 | 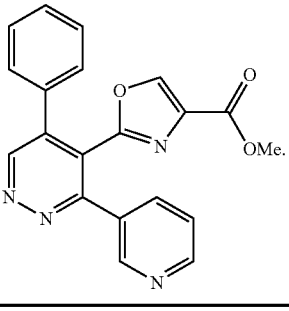 |
61. A pharmaceutical composition comprising a compound according to any one of claims 1-60 or a pharmaceutically acceptable salt thereof, in a therapeutically effective amount; and an acceptable carrier, adjuvant or vehicle.
* * * * *